United States Patent
Ratajczak et al.

(10) Patent No.: US 11,312,940 B2
(45) Date of Patent: Apr. 26, 2022

(54) PROGENITOR CELLS AND METHODS FOR PREPARING AND USING THE SAME

(71) Applicant: University of Louisville Research Foundation, Inc., Louisville, KY (US)

(72) Inventors: Mariusz Z. Ratajczak, Louisville, KY (US); Janina Ratajczak, Louisville, KY (US); Magdalena Kucia, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 443 days.

(21) Appl. No.: 15/253,239

(22) Filed: Aug. 31, 2016

(65) Prior Publication Data

US 2017/0108499 A1    Apr. 20, 2017

Related U.S. Application Data

(60) Provisional application No. 62/212,157, filed on Aug. 31, 2015.

(51) Int. Cl.
| | | |
|---|---|---|
| *G01N 31/00* | (2006.01) | |
| *G01N 33/53* | (2006.01) | |
| *C12N 5/0775* | (2010.01) | |
| *G01N 33/569* | (2006.01) | |

(52) U.S. Cl.
CPC ......... *C12N 5/0663* (2013.01); *C12N 5/0665* (2013.01); *G01N 33/56966* (2013.01); *C12N 2501/31* (2013.01); *C12N 2501/315* (2013.01); *C12N 2501/392* (2013.01)

(58) Field of Classification Search
None
See application file for complete search history.

(56) References Cited

U.S. PATENT DOCUMENTS

| | | | |
|---|---|---|---|
| 5,736,396 | A | 4/1998 | Bruder et al. |
| 5,750,397 | A | 5/1998 | Tsukamoto et al. |
| 5,843,780 | A | 12/1998 | Thomson |
| 6,090,622 | A | 7/2000 | Gearhart et al. |
| 6,458,589 | B1 | 10/2002 | Rambhatla et al. |
| 7,169,750 | B2 | 1/2007 | Bridger et al. |
| 7,422,736 | B2 | 9/2008 | Hwang |
| 7,575,921 | B2 | 8/2009 | Vacanti et al. |
| 7,816,140 | B2 | 10/2010 | Lau et al. |
| 8,252,587 | B2 | 8/2012 | Fong et al. |
| 8,859,282 | B2 | 10/2014 | Kale et al. |
| 9,079,965 | B2 * | 7/2015 | Zhou ............... C07K 16/32 |
| 9,155,762 | B2 | 10/2015 | Ratajczak et al. |
| 11,072,777 | B2 | 7/2021 | Ratajczak et al. |
| 2004/0018617 | A1 | 1/2004 | Hwang |
| 2004/0265281 | A1 | 12/2004 | Rodgerson et al. |
| 2005/0181502 | A1 | 8/2005 | Furcht et al. |
| 2005/0255588 | A1 | 11/2005 | Young et al. |
| 2006/0134783 | A1 | 6/2006 | Fong et al. |
| 2006/0233768 | A1 | 10/2006 | Hirose et al. |
| 2007/0243172 | A1 | 10/2007 | Ra et al. |
| 2008/0038231 | A1 | 2/2008 | Rodgerson et al. |
| 2008/0206343 | A1 | 8/2008 | Edinger et al. |
| 2008/0241171 | A1 | 10/2008 | Gentry et al. |
| 2009/0155225 | A1 | 6/2009 | Ratajczak et al. |
| 2009/0162329 | A1 | 6/2009 | Anversa et al. |
| 2009/0220466 | A1 | 9/2009 | Ratajczak et al. |
| 2010/0267107 | A1 | 10/2010 | Zuba-Surma et al. |
| 2012/0114614 | A1 | 5/2012 | Ratajczak |
| 2014/0154219 | A1 | 6/2014 | Ratajczak et al. |
| 2015/0174173 | A1 | 6/2015 | Ratajczak et al. |
| 2016/0151421 | A1 | 6/2016 | Ratajczak et al. |
| 2019/0093075 | A1 | 3/2019 | Ratajczak et al. |

FOREIGN PATENT DOCUMENTS

| | | |
|---|---|---|
| EP | 2535403 | 6/2019 |
| WO | WO 01/11011 A2 | 2/2001 |
| WO | WO 04043990 A2 | 5/2004 |
| WO | WO 04089439 A2 | 10/2004 |
| WO | WO 05042723 A2 | 5/2005 |

(Continued)

OTHER PUBLICATIONS

Mierzejewska et al., Stem Cells Dev., Apr. 15, 2015; 24(8): 927-937, Published online Jan. 21, 2015.*
Zuo et al. (Protein Engineering, vol. 13, No. 5, pp. 361-367, 2000) (Year: 2000).*
Luo et al. (Luo et al. Moleuclar Pharmaceutics, 2014, vol. 11, pp. 1750-1761) (Year: 2014).*
Costa etal. (European Journal of Pharmaceutics and Biopharmaceutics 74 (2010) 127-138). (Year: 2010).*
Mierzejewska et al. (Stem Cells and Development, Vo.24, No. 8, 2015, pp. 927-937, published online Jan. 21, 2015) (Year: 2015).*
Sriraman et al. (Reproductive Sciences, 2015, vol. 22, No. 7, 2015, pp. 884-903, published Jun. 23, 2015) (Year: 2015).*
Okuno et al. (PNAS, Apr. 30, 2002, vol. 99, No. 9, pp. 6246-6251) (Year: 2002).*

(Continued)

*Primary Examiner* — Lisa V Cook
(74) *Attorney, Agent, or Firm* — Jenkins, Wilson, Taylor & Hunt, P.A.

(57) ABSTRACT

Provided are methods for isolating subpopulations of stem cells. In some embodiments, the presently disclosed methods include selecting subsets of cells that are positive for CD34 or Sca-1, are further positive for one or more of FSHR, LHCGR, PRLR, AR, ESRα, ESRβ, and PGR; and are negative for each of CD45R/B220, Gr-1, TCRαβ, TCRγδ, CD11b, and Ter-119. In some embodiments, the subpopulations are further fractioning into CD45⁻ and CD45⁺ fractions. Also provided are populations of stem cells isolated by the presently disclosed methods, compositions that include the presently disclosed subpopulations in pharmaceutically acceptable carriers, methods for expanding stem cells, methods for stimulating proliferation of MSCs, methods for treating subjects suffering from exposure to radiation, and methods for producing gametes in vitro.

3 Claims, 17 Drawing Sheets
(6 of 17 Drawing Sheet(s) Filed in Color)
Specification includes a Sequence Listing.

(56) References Cited

FOREIGN PATENT DOCUMENTS

| | | | |
|---|---|---|---|
| WO | WO 2007/067280 | 6/2007 | |
| WO | WO 2007/146432 A2 | 12/2007 | |
| WO | WO 2008/087256 A1 | 7/2008 | |
| WO | WO-2009059032 A2 * | 5/2009 | ........... A61K 38/193 |
| WO | WO 2010/039241 | 4/2010 | |
| WO | WO 2010/057110 A1 | 5/2010 | |
| WO | WO 2011/069117 A1 | 6/2011 | |
| WO | WO 2015/054315 A1 | 4/2015 | |

OTHER PUBLICATIONS

Cornetta et al. (1998) Rapid engraftment after allogeneic transplantation using CD34-enriched marrow cells. Bone Marrow Transplantation 21:65-71.

Hirschi and Goodell (2002) Hematopoietic, vascular and cardiac fates of bone marrow-derived stem cells. Gene Therapy 9:648-652.

Office Action corresponding to U.S. Appl. No. 14/844,980 dated Dec. 1, 2017.

Guerin et al. (2015) Bone-marrow-derived very small embryonic-like stem cells in patients with critical leg ischaemia: evidence of vasculogenic potential. Thromb Haemost 113:1084-1094.

Haynesworth et al. (1992) Characterization of cells with osteogenic potential from human marrow. Bone 13:81-88.

Jiang et al. (2002b) Pluripotency of mesenchymal stem cells derived from adult marrow. Nature 418(6893):41-49.

Kim et al. (2010) Bone morphogenetic protein 4 stimulates attachment of neurospheres and astrogenesis of neural stem cells in neurospheres via phosphatidylinositol 3 kinase-mediated upregulation of N-cadherin. Neuroscience 170:8-15 (XP055031897).

Kucia et al. (2005a) Are bone marrow stem cells plastic or heterogenous—That is the question. Experimental Hematology 33(6):613-623.

Paczkowska et al. (2005) Human hematopoietic stem/progenitor-enriched CD34(+) cells are mobilized into peripheral blood during stress related to ischemic stroke or acute myoyardial infarction. European Journal of Heamatology 75(6):461-467.

Pittenger et al. (2000) Human mesenchymal stem cells: progenitor cells for cartilage, bone, fat and stroma. CurrTop Microbiol Immunol 251:1-10.

Ratajczak et al. (2012a) A novel perspective on stem cell homing and mobilization: review on bioactive lipids as potent chemoattractants and cationic peptides as underappreciated modulators of responsiveness to SDF-1 gradients. Leukemia 26:63-72.

Saitoh et al. (1999) Comparison of erythropoietic response to androgen in young and old senescence accelerated mice. Mech Ageing Dev 109:125-139.

Sovalat et al. (2011) Identification and isolation from either adult human bone marrow or G-CSF-mobilized peripheral blood of CD34(+)/CD133(+)/CXCR4(+)/ Lin(−)CD45(−) cells, featuring morphological, molecular, and phenotypic characteristics of very small embryonic-like (VSEL) stem cells. Exp Hematology 39:495-505.

Stimpfel et al. (2013) Isolation, characterization and differentiation of cells expressing pluripotent/multipotent markers from adult human ovaries. Cell Tissue Res 354:593-607.

Tanaka et al. (2002) Effect of Continuous Subcutaneous Administration of a Low Dose of G-CSF on Stem Cell Mobilization in Healthy Donors: A Feasibility Study. International Journal of Hematology, 75(5):489-492.

Yu et al. (1987) Importance of FSH-releasing protein and inhibin in erythrodifferentiation. Nature 330:765-767.

Zuba-Surma et al. (2008a) CD45-/ALDH (low)/SSEA-4(+)/Oct-4(+)/CD133(+)/CXCR4(+)/Lin(−) Very Small Embryonic-Like (VSEL) Stem Cells Isolated from Umbilical Cord Blood as Potential Long Term Repopulating Hematopoietic Stem Cells. Blood 112(11):1-2. (Abstract).

Zuba-Surma & Ratajczak (2010a) Overview of very small embryonic-like stem cells (VSELs) and methodology of their identification and isolation by flow cytometric methods. Curr Protoc Cytom Unit 9.25:1-15.

Ratajczak (2008a) Phenotypic and functional characterization of hematopoietic stem cells. Curr Opin Hematol 15:293-300.

Basiji et al. (2007) Cellular Image Analysis and Imaging by Flow Cytometry. Clin Lab Med 27:653-670.

Brunt et al. (2012) Stem Cells and Regenerative Medicine—Future Perspectives. Can. J. Physiol. Pharmacol. 90:327-335.

Burger et al. (2002) Fibroblast Growth Factor Receptor-1 Is Expressed by Endothelial Progenitor Cells. Blood 100:3527-3535.

Carrion et al. (2003) A randomised study of 10 ug/kg/day (single dose) vs 2 x 5 f.JQ/kg/day (split dose) G-CSF as stem cell mobilisation regimen in high-risk breast cancer patients., Bone Marrow Transplantation 32(6):563-567.

Chen et al., (2001) Therapeutic Benefit of Intravenous Administration of Bone Marrow Stromal Cells After Cerebral Ischemia in Rats, Stoke 32:1005-1011.

Cottier-Fox et al. (2003) Stem Cell Mobilization. Hematology 419-437.

Crosby et al. (2001) Human Hepatic Stem-like Cells Isolated Using c-kit or CD34 Can Differentiate Into Biliary Epithelium. Gastroenterology 120:534-544.

D'Ippolito et al. (2004) Marrow-isolated adult multilineage inducible (MIAMI) cells, a unique population of postnatal young and old human cells with extensive and differentiation potential. Journal of Cell Science 117(14): 2971-2981.

Danova-Alt et al. (2012) Very Small Embryonic-Like Stem Cells Purified from Umbilical Cord Blood Lack Stem Cell Characteristics. PLoS One 7(4):e34899.

Dawn et al. (2008) Transplantation of bone marrow-derived very small embryonic-like stem cells attenuates left ventricular dysfunction and remodeling after myocardial infarction. Stem Cells, ALP Hamed Press, 26(6): 1646-1655.

European Search Report corresponding to European Application No. 11831724.7 dated Mar. 17, 2014.

European Search Report corresponding to European Application No. 12763497.0-1402/2694651 dated Oct. 29, 2014.

European Search Report corresponding to European Patent Application No. 09826922.8, dated Jun. 18, 2012.

European Search Report Report corresponding to European Application No. 12166007.0-2401 dated Nov. 16, 2012.

Fiegel et al. (2003) Characterization of Cell Types During Rat Liver Development. Hepatology 37:148-154.

Gallacher et al. (2000) Isolation and characterization of human CD34-Lin- and CD34+Lin-hematopoietic stem cells using cell surface markers AC133 and CD7. Blood 95:2813-2820.

Grymula et al. (2014) Evidence that the population of quiescent bone marrow-residing very small embryonic/epiblast-like stem cells (VSELs) expands in response to neurotoxic treatment. J Cell Mol Med 18:1797-1806.

Halasa et al. (2008) An efficient two-step method to purify very small embryonic-like (VSEL) stem cells from umbilical cord blood (UCB). Folia Histochemica et Cytobiologica, 46(2):239-243.

Havens et al. (2013) Human very small embryonic-like cells generate skeletal structures, in vivo. Stem Cells Dev 22:622-630.

Havens et al. (2014) Human and murine very small embryonic-like cells represent multipotent tissue progenitors, in vitro and in vivo. Stem Cells Dev 23:689-701.

Hess et al. (2004) Functional characterization of highly purified human hematopoietic repopulating cells isolated according to aldehyde dehydrogenase activity. Blood 104:1648-1655.

Hess et al. (2006) Selection based on CD133 and high aldehyde dehydrogenase activity isolates long-term reconstituting human hematopoietic stem cells. Blood 107:2162-2169.

Hess et al. (2008) Widespread Nonhematopoietic Tissue Distribution by Transplanted Human Progenitor Cells With High Aldehyde Dehydrogenase Activity., Stem Cells, Dayton, Ohio, 26(3):611-620.

Houssaint (1980) Differentiation of the Mouse Hepatic Primordium. I. An Analysis of Tissue Interactions in Hepatocyte Differentiation. Cell Differ 9:269-279.

International Preliminary Report on Patentability corresponding to Patent Application No. PCT/US07/014108 dated Dec. 16, 2008.

International Preliminary Report on Patentability Corresponding to Patent Application No. PCT/US2008/081832 dated Mar. 25, 2009.

(56) References Cited

OTHER PUBLICATIONS

International Preliminary Report on Patentability and Written Opinion of the International Searching Authority corresponding to International Patent Application No. PCT/US06/042780 dated Apr. 24, 2009.
International Preliminary Report on Patentability Corresponding to Patent Application No. PCT/US2009/005414 dated Mar. 2, 2010.
International Preliminary Report on Patentability corresponding to International Patent Application No. PCT/US2009/064614 dated May 26, 2011.
International Preliminary Report on Patentability corresponding to International Patent Application No. PCT/US2011/055473 dated Apr. 9, 2013.
International Search Report corresponding to European Application No. PCT/EP2009/064614 dated Feb. 22, 2010.
International Search Report and Written Opinion of International Patent Application No. PCT/US08/81832 dated Mar. 25, 2009.
International Search Report corresponding to U.S. Patent Application No. PCT/US06/042780 dated Jun. 30, 2009.
International Search Report corresponding to International Application No. PCT/US2009/064614, dated Apr. 2, 2010.
International Search Report corresponding to International Patent Application No. PCT/US09/05414 dated Mar. 2, 2010.
International Search Report corresponding to International Application No. PCT/EP2009/064612 dated Jul. 29, 2010.
International Search Report and Written Opinion of the International Searching Authority Corresponding to Application No. PCT/US 12/31869 dated Jul. 27, 2012.
Interview Summary corresponding to U.S. Appl. No. 13/877,963 dated Jan. 23, 2015.
Interview Summary corresponding to U.S. Appl. No. 13/129,359 dated Jul. 15, 2015.
Ito et al. (2010) The ACC133+CD38-, but not the rhodamine-low, phenotype tracks LTC-IC and SRC function in human cord blood ex vivo expansion cultures. Blood 115:257-260.
Jiang et al. (2002a) Multipotent progenitor cells can be isolated from postnatal murine bone marrow, muscle and brain. Exp Hematol 30:896-904.
Jung et al. (1999) Initiation of Mammalian Liver Development from Endoderm by Fibroblast Growth Factors. Science 284:1998-2003.
Kassmer et al. (2013) Very small embryonic-like stem cells from the murine bone marrow differentiate into epithelial cells of the lung. Stem Cells 31:2759-2766.
Kiel et al. (2005) SLAM Family Receptors Distinguish Resource Hematopoietic Stem and Progenitor Cells and Reveal Endothelial Niches for Stem Cells. Cell 121:1109-1121.
Kogler et al. (2004) A new human somatic stem cell from placetal cord blood with intrinsic pluripotent differentiation potential. Journal of Experimental Medicine 200(2):123-135.
Krause (2008) Bone Marrow-derived Cells and Stem Cells in Lung Repair. Proc Am Thorac Soc 5:323-327.
Krupnick et al. (2004) Fetal Liver as a Source of Autologous Progenitor Cells for Perinatal Tissue Engineering. Tissue Eng 10:723-735.
Kucia et al. (2004) Cells expressing early cardiac markers reside in the bone marrow and are mobilized into the peripheral blood after myocardial infarction. Circulation Research 95:1191-1199.
Kucia et al. (2005b) Bone marrow as a home of heterogeneous populations of nonhematopoietic stem cells., Leukemia (BASINGSTOKE) 19(7):1118-1127.
Kucia et al. (2005c) Bone marrow as a source of circulating CXCR4(+) tissue-committed stem cells. Biology of the Cell 97(2):133-146.
Kucia et al. (2006a) A population of very small embryonic-like (VSEL) CXCR4+SSEA-1+Oct-4+ stem cells identified in adult bone marrow. Leukemia 20:857-869.
Kucia et al. (2006b) A population of very small embryonic-like (VSEL) CXCR4+SSEA-1+Oct4+ stem cells identified in adult bone marrow. Leukemia 20 pp. 857-869.
Kucia et al. (2006c) Cells enriched in markers of neural tissue-committed stem cells reside in the bone marrow and are mobilized into the peripheral blood following stroke. Leukemia 20(18-28).
Kucia et al. (2006d) Physiological and pathological consequences of identification of very small embryonic like (VSEL) stem cells in adult bone marrow., Journal of Physiology and Pharmacology 57(Supp 5):5-18.
Kucia et al. (2006e) The migration of bone marrow-derived non-hematopoietic tissue-committed stem cells is regulated in an SDF-1, HGF-, and LIF-dependent manner., Archivum Immunologiae et Therapiae Experimentalis, Birkhaeuser Verlag AG. 54:121-135.
Kucia et al. (2007) Morphological and molecular characterization of novel population of CXCR4+ SSEA-4+ Oct-4+ very small embryonic-like cells purified from human cord blood—preliminary report. Leukemia 21:297-303.
Kucia et al. (2008a) Evidence that very small embryonic-like cells are mobilized into peripheral blood. Stem Cells 26:2083-2092.
Kucia et al. (2008b) Identification of very small embryonic like (VSEL) stem cells in bone marrow. Cell and Tissue Research 331:125-134.
Larochelle et al. (1996) Identification of primitive human hematopoietic cells capable of repopulating NOD/SCID mouse bone marrow: Implications for gene therapy. Nat Med 2(12):1329-1337.
Lee et al. (2010) Placenta as a newly identified source of hematopoietic stem cells. Curr Opin Hematol 17:313-318.
Lee et al. (2011) Progesterone promotes differentiation of human cord blood fetal T cells into T regulatory cells but suppresses their differentiation into Th17 cells. J Immunol 187:1778-1787.
Lemmer et al. (1998) Isolation from human fetal liver of cells co-expressing CD34 haematopoietic stem cell and CAM 5.2 pancytokeratin markers. J Hepatol 29:450-454.
Leor et al. (2005) Human umbilical cord blood-derived CD133+ cells enhance function and repair of the infarcted myocardium. Stem Cells 24(3) 772-780.
Luo et al. (2013) Upregulated H19 contributes to bladder cancer cell proliferation by regulating ID2 expression. FEBS J 280:1709-1716.
Mason et al. (2001) CD Antigens 2001. European Journal of Immunology 31 (10): 2841-2847.
McGuckin et al. (2005) Production of stem cells with embryonic characteristics from human umbilical cord blood. Cell Prolif 38:245-255.
McGuckin et al. (2008) Culture of embryonic-like stem cells from human umbilical cord blood and onward differentiation to neural cells in vitro. Nature Protocols 3(6):1046-1055.
McKinney-Freeman et al. (2002) Muscle-derived hematopoietic stem cells are hematopoietic in origin. Proc Natl Acad Sci USA 99:1341-1346.
Medicetty et al. (2009) Evidence That Human Very Small Embryonic-Like Stem Cells (VSELs) Are Mobilized by G-CSF Into Peripherial Blood: A Novel Strategy to Obtain Human Pluripotent Stem Cells for Regenerative Medicine. Blood 114:1474.
Mierzejewska et al. (2015) Hematopoietic stem/progenitor cells express several functional sex hormone receptors—novel evidence for a potential developmental link between hematopoiesis and primordial germ cells. Stem Cells Dev 24:927-937.
Miki et al. (2005) Stem Cell Characteristics of Amniotic Epithelial Cells. Stem Cells 23:1549-1559.
Mimura et al. (2005) Treatment of Rabbit Bullous Keratopathy with Precursors Derived from Cultured Human Corneal Endothilium, Investigative Ophthalmology and Visual Science 46:3637-3644.
Minguet et al. (2003) A population of c-Kitlow(CD45/TER119)— hepatic cell progenitors of 11-day postcoitus mouse embryo liver reconstitutes cell-depleted liver organoids. J Clin Invest 112:1152-1163.
Nakada et al. (2014) Oestrogen increases haematopoietic stem-cell self-renewal in females and during pregnancy. Nature. 505:555-558.
Naldini. (2011) Ex vivo gene transfer and correction for cell-based therapies. Nature Reviews: Genetics 12:301-315.
Nava et al. (2005) Characterization of cells in the developing human liver. Differentiation 73:249-260.
Nguyen et al. (2010) Methods to Assess Stem Cell Lineage, Fate and Function. Advanced Drug Delivery Reviews. 62:1175-1186.

(56) References Cited

OTHER PUBLICATIONS

Nierhoff et al. (2005) Purification and characterization of mouse fetal liver epithelial cells with high in vivo repopulation capacity. Hepatology 42:130-139.
Notice of Allowance and Fee(s) Due and Examiner Initiated Interview Summary for U.S. Appl. No. 12/740,718 dated May 29, 2015.
Notification Concerning Transmittal of International Preliminary Report on Patentability (Chapter I of the Patent Cooperation Treaty), corresponding to International application PCT/US2013/047435 dated Jan. 8, 2015.
Notification of Transmittal of the International Search Report and the Written Opinion of the International Searching Authority, or the Declaration, corresponding to International application PCT/US2013/047435 dated Nov. 29, 2013.
Notification of Transmittal of the International Search Report and the Written Opinion of the International Searching Authority corresponding to International Patent Application No. PCT/US2011/55473 dated Feb. 23, 2012.
Notification of Transmittal of the International Search Report and the Written Opinion of the International Searching Authority, or the Declaration for International Application No. PCT/US09/64612 dated Apr. 9, 2010.
Nowak et al. (2005) Identification of expandable human hepatic progenitors which differentiate into mature hepatic cells in vivo. Gut 54:972-979.
Office Action corresponding to European Patent Application No. EP 078 09 600.5 dated May 11, 2009.
Office Action corresponding to Australian Patent Application No. 2011312128 dated Oct. 10, 2014.
Office Action corresponding to European Patent Application No. 09826922.8 dated Aug. 26, 2014.
Office Action corresponding to European Patent Application No. 11 831 724.7-1408 dated Dec. 8, 2014.
Office Action corresponding to U.S. Appl. No. 13/129,359 dated Oct. 30, 2014.
Office Action corresponding to U.S. Appl. No. 13/129,359 dated Jun. 20, 2013.
Office Action corresponding to U.S. Appl. No. 13/129,359 dated Oct. 12, 2012.
Office Action corresponding to U.S. Appl. No. 13/129,359 dated Jun. 3, 2015.
Office Action corresponding to U.S. Appl. No. 13/129,352 dated May 2, 2014.
Office Action corresponding to U.S. Appl. No. 13/877,963 dated Mar. 6, 2015.
Office Action corresponding to U.S. Appl. No. 14/136,436 dated Mar. 26, 2015.
Office Action corresponding to U.S. Appl. No. 12/096,754 dated Nov. 22, 2011.
Office Action corresponding to U.S. Appl. No. 13/121,913 dated Dec. 13, 2011.
Office Action corresponding to U.S. Appl. No. 12/096,754 dated Jul. 30, 2012.
Office Action corresponding to U.S. Appl. No. 14/008,796 dated May 4, 2015.
Office Action corresponding to U.S. Appl. No. 14/008,796 dated Nov. 2, 2015.
Office Action corresponding to U.S. Appl. No. 14/958,409 dated Feb. 3, 2017.
Office Action corresponding to U.S. Appl. No. 14/844,980 dated Aug. 22, 2016.
Office Action corresponding to U.S. Appl. No. 12/740,718 dated Oct. 4, 2012.
Office Action corresponding to Chinese Patent Application No. 200980154497.X dated Dec. 6, 2012.
Office Action corresponding to U.S. Appl. No. 12/740,718 dated May 31, 2013.
Office Action corresponding to Chinese Patent Application No. 200980154497.X dated Sep. 30, 2013.
Office Action corresponding to U.S. Appl. No. 12/740,718 dated Sep. 30, 2014.
Office Action corresponding to U.S. Appl. No. 14/409,507 dated Aug. 10, 2016.
Office Action corresponding to U.S. Appl. No. 14/844,980 dated Apr. 21, 2017.
Paczkowska et al. (2009) Clinical evidence that very small embryonic-like stem cells are mobilized into peripheral blood in patients after stroke. Stroke 40:1237-1244.
Patel et al. (2013) Follicle Stimulating Hormone Modulated Ovarian Stem Cells through alternately spliced receptor variant FSH-R3. J. of Ova. Res 6:1-15.
Pelacho et al. (2007) Multipotent adult progenitor cell transplantation increases vascularity and improves left ventricular function after myocardial infarction., Journal of Tissue Engineering and Regeneratice Medicine 1:51-59.
Peterson et al. (1998) Hepatic Oval Cells Express the Hematopoietic Stem Cell Marker Thy-1 in the Rat. Hepatology 27:433-445.
Petit et al. (2002) G-CSF induces stem cell mobilization by decreasing bond marrow SDF-1 and up-regulating CXCR4., Nature Immunology 3(7):687-694.
Prockop (1997) Marrow Stromal Cells as Stem Cells for Nonhematopoietic Tissues., Science, 276(5309):71-74.
Ratajczak et al. (1994) A reappraisal of the role of insulin-like growth factor I in the regulation of human hematopoiesis. J Clin Invest 94:320-327.
Ratajczak et al. (2003) Expression of functional CXCR4 by muscle satellite cells and secretion of SDF-1 by muscle-derived fibroblasts is associated with the presence of both muscle progenitors in bone marrow and hematopoietic stem/progenitor cells in muscles. Stem Cells 21:363-371.
Ratajczak et al. (2004) Stem cell plasticity revisited: CXCR4-positive cells expressing mRNA for early muscle, liver and neural cells 'hide out' in the bone marrow, Leukemia 18:29-40.
Ratajczak et al. (2006) The pleiotropic effects of the SDF-1-CXCR4 axis in organigenesis, regeneration and tumorigenesis. Leukemia 20:1915-1924.
Ratajczak et al. (2007) A hypothesis for an embryonic origin of pluripotent Oct-4+ stem cells in adult bone marrow and other tissues. Leukemia 21:860-867.
Ratajczak et al. (2008b) Very Small Embryonic-Like (VSEL) Stem Cells: Purification from Adult Organs, Characterization, and Biological Significance. Stem Cell Research 4:89-99.
Ratajczak et al. (2008c) Very Small Embryonic Like (VSEL) Stem Cells—Characterization, Developmental Origin and Biological Significance. Exp Hematol 36:742-751.
Ratajczak et al. (2008d) Very small embryonic-like (VSEL) stem cells in adult organs and their potential role in rejuvenation of tissues and longevity. Experimental Geronotology 43:1009-1017.
Ratajczak et al. (2008e) Very Small Embryonic-Like (VSEL) Stem Cells: Purification from Adult Organs, Characterization, and Biological Significance. J Autoimmun 30:151-162.
Ratajczak et al. (2008f) Very Small Embryonic-Like (VSEL) Stem Cells: Purification from Adult Organs, Characterization, and Biological Significance. Stem Cell Rev 4:89-99.
Ratajczak et al. (2011a) Adult murine bone marrow-derived very small embryonic-like stem cells differentiate into the hematopoietic lineage after coculture over OP9 stromal cells. Experimental Hematology 39(2):225-237.
Ratajczak et al. (2011b) Hematopoietic differentiation of umbilical cord blood-derived very small embryonic/epiblast-like stem cells. Leukemia 25:1278-1285.
Ratajczak et al. (2011c) Stem cells for neural regeneration—a potential application of very small embryonic-like stem cells. J Physiol Pharmacol 62(1):3-12.
Reynolds & Weiss (2005) Clonal and population analyses demonstrate that an EGF-responsive mammalian embryonic CNS precursor is a stem cell. Developmental Biology 175:1-13.
Rich (1995) Primordial germ cells are capable of producing cells of the hematopoietic system in vitro. Blood 86:463-472.

(56) References Cited

OTHER PUBLICATIONS

Rossi et al. (2001) Distinct mesodermal signals, including BMPs from the septum transversum mesenchyme, are required in combination for hepatogenesis from the endoderm. Genes Dev 15:1998-2009.
Sanchez-Aguilera et al. (2014) Estrogen signaling selectively induces apoptosis of hematopoietic progenitors and myeloid neoplasms without harming steady-state hematopoiesis. Cell Stem Cell 15:791-804.
Shin et al. (2009) Novel epigenetic mechanisms that control pluripotency and quiescence of adult bone marrow-derived Oct4(+) very small embryonic like stem cells. Leukemia 23(11):2042-2051.
Stilley et al. (2014) Signaling through FSH receptors on human umbilical vein endothelial cells promotes angiogenesis. J Clin Endocrinol Metab 99:E813-E820.
Supplementary Search Report corresponding to European Patent Application No. 06827358.0 dated Dec. 30, 2009.
Suszynska et al. (2014a) The proper criteria for identification and sorting of very small embryonic-like stem cells, and some nomenclature issues. Stem Cells and Development 23(7):702-713.
Suszynska et al. (2014b) Expression of the erythropoietin receptor by germline-derived cells—further support for a potential developmental link between the germline and hematopoiesis. J Ovarian Res 7:66.
Suzuki et al. (2000) Flow-Cytometric Separation and Enrichment of Hepatic Progenitor Cells in the Developing Mouse Liver. Hepatology 32:1230-1239.
Suzuki & Nakauchi (2002a) Identification and propagation of liver stem cells. Semin Cell Dev Biol 13:455-461.
Suzuki et al. (2002b) Clonal identification and characterization of self-renewing pluripotent stem cells in the developing liver. J Cell Biol 156:173-184.
Sylvester et al. (2004) Stem cells: review and update. Arch Surg 139:93-99.
Tada et al. (2006) Morphological Study of the Transition of Haematopoietic Sites in the Developing Mouse During the Perinatal Period. Anat Histol Embryol 35:235-240.
Taichman et al. (2010) Prospective Identification and Skeletal Localization of Cells Capable of Multilineage Differentiation in Vivo. Stem Cells Dev 19:1557-1570.
Takamaru et al. (2012) Aberrant methylation of RASGRF1 is associated with an epigenetic field defect and increased risk of gastric cancer. Cancer Prev Res 5(10):1203-1212.
Tamamura et al. (1998) A Low-Molecular Weight Inhibitor Against the Chemokine Receptor CXCR4: A Strong Anti-HIV Peptide T140. Biochem BIophys Res Commun 253:877-882.
Tavian & Peault (2005) Embryonic development of the human hematopoietic system. Int J Dev Biol 49:243-250.
Wang et al. (2003) SCID-repopulating cell activity of human cord blood—derived CD34 cells assured by intra-bone marrow injection. Blood 101:2924-2931.
Wiktor-Jedrzejczak et al. (1979) Different marrow cell number requirements for the haemopoietic colony formation and the curve of the W/Wv anemia. Experientia 35:546-547.
Zaret (2000) Liver specification and early morphogenesis. Mech Dev 92:83-88.
Zaret (2001) Hepatocyte differentiation: from the endoderm and beyond. Curr Opin Genet Dev 11:568-574.
Zaret (2002) Regulatory Phases of Early Liver Development: Paradigms of Organogenesis. Nat Rev Genet 3:499-512.
Zuba-Surma et al. (2007a) Abstract 1276: Pluripotent Bone Marrow (BM)—Derived Very Small Embryonic-Like (VSEL) Stem Cells are Mobilized after Acute Myocardial Infarction in Mice. Circulation 116(II):260.
Zuba-Surma et al. (2007b) The ImageStream System: a key step to a new era in imaging. Folia Histochem Cytobiol 45(4):279-290.
Zuba-Surma et al. (2008b) Very Small Embryonic-Like Stem Cells Are Present in Adult Murine Organs: ImageStream-Based Morphological Analysis and Distribution Studies. Cytometry Part A 73A:1116-1127.
Zuba-Surma et al. (2008c) Morphological characterization of very small embryonic-like stem cells (VSELs) by ImageStream system analysis. J Cell Mol Med 12(1):292-303.
Zuba-Surma et al. (2009a) CD45-/Lin-/CD133+/ALDH-low VSEL stem cells isolated from cord blood—as potential long term repopulating hematopoietic stem cells (LT-HSC). Human Gene Therapy 20(11):1469-1470.
Zuba-Surma et al. (2009c) In Vitro and in Vivo Evidence That Umbilical Cord Blood (UCB)—DerivedCD45-/SSEA-4+/OCT-4+/CD133+/ CXCR4+/Lin—Very Small Embryonic/Epiblast Like Stem Cells (VSELs) Do Not Contain Clonogenic Hematopoietic Progenitors but Are Highly Enriched in More Primitive Stem Cells. 51st Ash Annual Meeting and Exposition, Abstract No. 35:1-2.
Zuba-Surma et al. (2010) Optimization of isolation and further characterization of umbilical cord blood-derived very small embryonic/epiblast-like stem cells (VSELs). Eur J Haematol 84:34-46.
Office Action corresponding to U.S. Appl. No. 14/844,980 dated Aug. 8, 2018.
Decision to Grant corresponding to European Patent Application No. 12166007.0 dated May 23, 2019.
International Preliminary Report on Patentability corresponding to International Patent Application No. PCT/US17/20696 dated Sep. 13, 2018.
Notice of Intent to Grant corresponding to European Patent Application No. 12166007.0 dated Jan. 9, 2019.
Office Action corresponding to U.S. Appl. No. 16/081,665 dated Mar. 10, 2020.
Notice of Allowance and Fee(s) Due and Examiner Initiated Interview Summary for U.S. Appl. No. 16/081,665 dated Mar. 22, 2021.
Office Action corresponding to U.S. Appl. No. 16/081,665 dated Sep. 24, 2020.
Chaurasia et al., "Epigenetic reprogramming induces the expansion of cord blood stem cells," Journal of Clinical Investigation, vol. 124, No. 6, pp. 2378-2395 (2014).
European Search Report corresponding to European Application No. 17760911.2-1120 dated Oct. 10, 2019.
Office Action (Restriction Requirement) corresponding to U.S. Appl. No. 16/081,665 dated Oct. 16, 2019.

\* cited by examiner

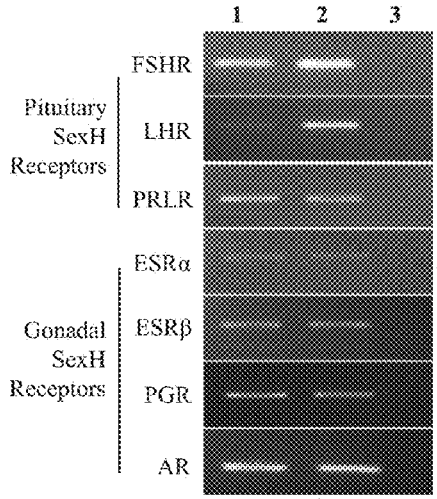
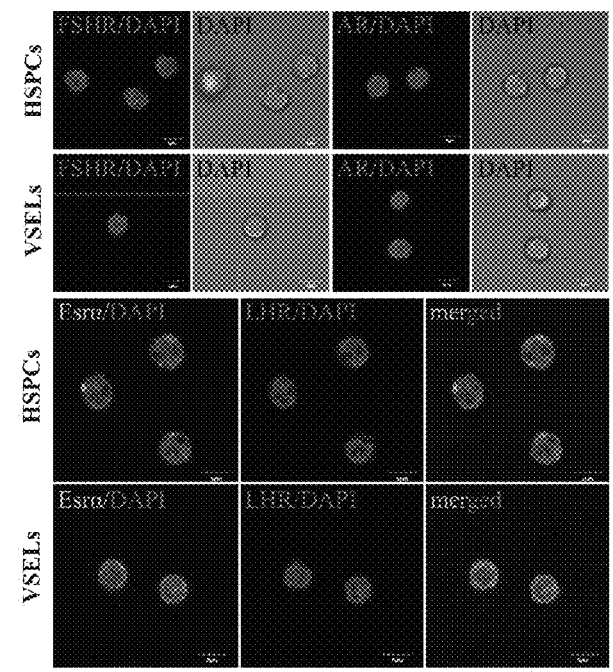
FIG. 1A
FIG. 1B
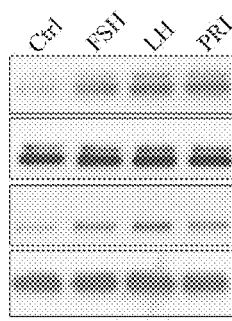
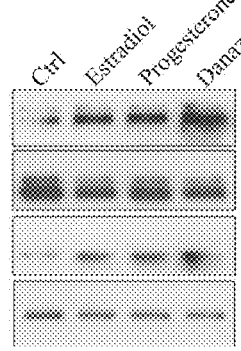
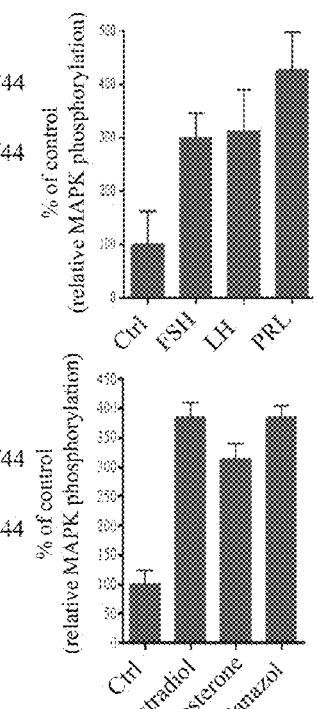
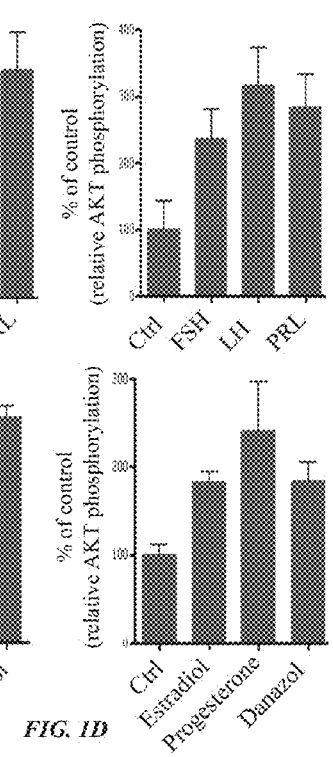
FIG. 1C
FIG. 1D

SEQUENCE LISTING

<160> NUMBER OF SEQ ID NOS: 32

<210> SEQ ID NO 1
<211> LENGTH: 22
<212> TYPE: DNA
<213> ORGANISM: Homo sapiens

<400> SEQUENCE: 1
gcttctgaga tctgtggagg tt                                            22

<210> SEQ ID NO 2
<211> LENGTH: 22
<212> TYPE: DNA
<213> ORGANISM: Homo sapiens

<400> SEQUENCE: 2
ggacaaacct cagttcaatg gc                                            22

<210> SEQ ID NO 3
<211> LENGTH: 19
<212> TYPE: DNA
<213> ORGANISM: Homo sapiens

<400> SEQUENCE: 3
cagaggccgt ccaagacac                                                19

<210> SEQ ID NO 4
<211> LENGTH: 20
<212> TYPE: DNA
<213> ORGANISM: Homo sapiens

<400> SEQUENCE: 4
atgctccggg ctcaatgtat                                               20

<210> SEQ ID NO 5
<211> LENGTH: 21
<212> TYPE: DNA
<213> ORGANISM: Homo sapiens

<400> SEQUENCE: 5
gagcttcttc tcacagagcc a                                             21

<210> SEQ ID NO 6
<211> LENGTH: 24
<212> TYPE: DNA
<213> ORGANISM: Homo sapiens

<400> SEQUENCE: 6
aagttcactt cagggttcat gtgg                                          24

<210> SEQ ID NO 7
<211> LENGTH: 20
<212> TYPE: DNA
<213> ORGANISM: Homo sapiens

<400> SEQUENCE: 7
cgacttcacc gcacctgatg                                               20

<210> SEQ ID NO 8
<211> LENGTH: 21
<212> TYPE: DNA
<213> ORGANISM: Homo sapiens

<400> SEQUENCE: 8
acttctgttt cccttcagcg g                                              21

<210> SEQ ID NO 9
<211> LENGTH: 20
<212> TYPE: DNA
<213> ORGANISM: Homo sapiens

<400> SEQUENCE: 9
aggtgcccta ctacctggag                                                20

<210> SEQ ID NO 10
<211> LENGTH: 21
<212> TYPE: DNA
<213> ORGANISM: Homo sapiens

<400> SEQUENCE: 10
cggtcttttc gtatcccacc t                                              21

<210> SEQ ID NO 11
<211> LENGTH: 20
<212> TYPE: DNA
<213> ORGANISM: Homo sapiens

<400> SEQUENCE: 11
aatggtgaag tgtggctccc                                                20

<210> SEQ ID NO 12
<211> LENGTH: 20
<212> TYPE: DNA
<213> ORGANISM: Homo sapiens

<400> SEQUENCE: 12
acttggtcga acaggctgag                                                20

<210> SEQ ID NO 13
<211> LENGTH: 20
<212> TYPE: DNA
<213> ORGANISM: Homo sapiens

<400> SEQUENCE: 13
tcaactacct gaggccggat                                                20

<210> SEQ ID NO 14
<211> LENGTH: 20
<212> TYPE: DNA
<213> ORGANISM: Homo sapiens

<400> SEQUENCE: 14
cagcatccag tgctctcaca                                                20

<210> SEQ ID NO 15
<211> LENGTH: 22
<212> TYPE: DNA
<213> ORGANISM: Homo sapiens

<400> SEQUENCE: 15
ggtctcgatt ggatggcagt ag                                             22

<210> SEQ ID NO 16
<211> LENGTH: 20
<212> TYPE: DNA
<213> ORGANISM: Homo sapiens

```
<400> SEQUENCE: 16
cacccatggc agaaggagga                                               20

<210> SEQ ID NO 17
<211> LENGTH: 20
<212> TYPE: DNA
<213> ORGANISM: Homo sapiens

<400> SEQUENCE: 17
aatgcggcat cttcaaacct                                               20

<210> SEQ ID NO 18
<211> LENGTH: 23
<212> TYPE: DNA
<213> ORGANISM: Homo sapiens

<400> SEQUENCE: 18
tgactttgtc acagcccaag ata                                           23

<210> SEQ ID NO 19
<211> LENGTH: 21
<212> TYPE: DNA
<213> ORGANISM: Mus musculus

<400> SEQUENCE: 19
tcaacggaac ccagctagat g                                             21

<210> SEQ ID NO 20
<211> LENGTH: 22
<212> TYPE: DNA
<213> ORGANISM: Mus musculus

<400> SEQUENCE: 20
gtctaaaacg actggcccag ag                                            22

<210> SEQ ID NO 21
<211> LENGTH: 21
<212> TYPE: DNA
<213> ORGANISM: Mus musculus

<400> SEQUENCE: 21
atctgtaaca caggcatccg g                                             21

<210> SEQ ID NO 22
<211> LENGTH: 22
<212> TYPE: DNA
<213> ORGANISM: Mus musculus

<400> SEQUENCE: 22
cgttccctgg tatggtggtt at                                            22

<210> SEQ ID NO 23
<211> LENGTH: 19
<212> TYPE: DNA
<213> ORGANISM: Mus musculus

<400> SEQUENCE: 23
tgcttgctgg gaagtacgg                                                19

<210> SEQ ID NO 24
<211> LENGTH: 20
<212> TYPE: DNA
<213> ORGANISM: Mus musculus
```

<400> SEQUENCE: 24
ggtgacggag atagttgggg                                                20

<210> SEQ ID NO 25
<211> LENGTH: 19
<212> TYPE: DNA
<213> ORGANISM: Mus musculus

<400> SEQUENCE: 25
gactgcatgt acgcgtcgc                                                 19

<210> SEQ ID NO 26
<211> LENGTH: 22
<212> TYPE: DNA
<213> ORGANISM: Mus musculus

<400> SEQUENCE: 26
ggcgtaacct cccttgaaag ag                                             22

<210> SEQ ID NO 27
<211> LENGTH: 22
<212> TYPE: DNA
<213> ORGANISM: Mus musculus

<400> SEQUENCE: 27
gccaaggaga ctcgctactg tg                                             22

<210> SEQ ID NO 28
<211> LENGTH: 22
<212> TYPE: DNA
<213> ORGANISM: Mus musculus

<400> SEQUENCE: 28
tgtcaatggt gcattggttt gt                                             22

<210> SEQ ID NO 29
<211> LENGTH: 19
<212> TYPE: DNA
<213> ORGANISM: Mus musculus

<400> SEQUENCE: 29
taccccttgg ctaccgcaa                                                 19

<210> SEQ ID NO 30
<211> LENGTH: 19
<212> TYPE: DNA
<213> ORGANISM: Mus musculus

<400> SEQUENCE: 30
gcatcaggag gttggccag                                                 19

<210> SEQ ID NO 31
<211> LENGTH: 20
<212> TYPE: DNA
<213> ORGANISM: Mus musculus

<400> SEQUENCE: 31
aatggaaggg cagcacaact                                                20

<210> SEQ ID NO 32
<211> LENGTH: 21
<212> TYPE: DNA

```
<213> ORGANISM: Mus musculus

<400> SEQUENCE: 32
gcggatttta tcaacgatgc a                                              21
```

PROGENITOR CELLS AND METHODS FOR PREPARING AND USING THE SAME

CROSS REFERENCE TO RELATED APPLICATION

The presently disclosed subject matter claims the benefit of U.S. Provisional Patent Application Ser. No. 62/212,157, filed Aug. 31, 2015; the disclosure of which is incorporated herein by reference in its entirety.

GOVERNMENT INTEREST

This invention was made with government support under grants 2R01 DK074720 and R01HL112788 awarded by the United States National Institutes of Health. The government has certain rights in the invention.

TECHNICAL FIELD

The presently disclosed subject matter relates, in general, to the use of receptors for pituitary and gonadal sex hormones (SexHs) as markers for isolating subpopulations of mammalian stem cells. More particularly, the presently disclosed subject matter relates to isolating said stem cells using reagents that binds to the receptors and employing the same, optionally after in vitro manipulation, to treat tissue and/or organ damage in a subject in need thereof and/or for in vitro gametogenesis.

BACKGROUND

Development, migration, proliferation, and differentiation of hematopoietic stem/progenitor cells (HSPCs) is regulated in bone marrow (BM) by several well-defined growth factors, cytokines, chemokines, and bioactive lipids (Majka et al., 2001; Ratajczak et al., 2012a; Wu et al., 2012; Ratajczak, 2015). Evidence has accumulated that murine HSPCs share several markers with the germline, a connection supported recently by reports that pituitary and gonadal sex hormones (SexHs) regulate the development of murine HSPCs (Carreras et al., 2008; Maggio et al., 2013; Nakada et al, 2014). While the biological effects of SexHs on in vivo and in vitro murine hematopoiesis have recently been carefully evaluated by several groups (Jepson & Lowenstein, 1964; Saitoh et al., 1999; Olsen & Kovacs, 2001; Sanchez-Aguilera et al, 2014; Mierzejewska et al., 2015; Thangamani et al., 2015), the effects of these hormones, particularly pituitary SexHs, on human hematopoiesis requires further study.

For example, it is known that androgens can be successfully employed to treat aplastic anemia in patients (Selleri et al, 1991). On the other hand, it has been proposed that estrogens and progesterone indirectly regulate human erythropoiesis by involving monocytes (De Feo et al., 1991). By contrast, based on recent murine studies, it has been hypothesized that estrogens play a role during pregnancy in which HSPCs respond to increased oxygen consumption and produce increasing numbers of erythrocytes (Nakada et al, 2014). This latter hypothesis, however, still needs to be proven in humans. On the other hand, prolactin (PRL) compensates for erythropoietin deficiency in patients on dialysis because of chronic kidney failure, and both in vitro and in vivo studies suggest that PRL can accelerate lymphoid and myeloid reconstitution and promote hematopoiesis (Richards & Murphy, 2000; Dugan et al, 2002; Carreno et al, 2005). This multi-lineage effect of human PRL makes it an attractive candidate in several clinical settings presenting with myelosuppression or immune deficiency (Richards & Murphy, 2000). Moreover, estrogens have been shown to regulate the final stages of megakaryopoiesis by facilitating proplatelet formation (Matsumura & Sasaki, 1986; Nagata et al, 2003), while progesterone promotes differentiation of T cells into T regulatory cells (Lee et al., 2011; Thangamani et al, 2015).

In addition, the existence of developmentally early stem cells with broader specification in bone marrow (BM) and umbilical cord blood (UCB) that generated a recent heated debate has challenged the established hierarchy within the stem cell compartment (Ratajczak et al., 2014; Suszynska et al., 2014b). As reported recently, murine HSPCs express functional pituitary FSH and LH receptors in addition to gonadal SexH receptors (Mierzejewska et al., 2015). Furthermore, following observations that at least some murine BM-derived, $CD45^-$ very small embryonic-like stem cells (VSELs) become specified into $CD45^+$ HSPCs (Ratajczak et al, 2011a; Ratajczak et al., 2011b), it was found that VSELs, like HSPCs, do express functional SexH receptors (Mierzejewska et al., 2015). Since at least some VSELs share several markers characteristic of migrating primordial germ cells (PGCs; see Shin et al, 2010), this observation sheds new light on the BM stem cell hierarchy and the potential link between murine VSELs, HSPCs, and PGCs. Specifically, HSPCs might be specified at the time of embryogenesis from a population of migrating PGCs (Rich, 1995; Shin et al, 2010; Suszynska et al, 2014b), later on from VSELs residing in fetal liver (Zuba-Surma et al, 2009; Ratajczak et al, 2012b), and in adults from VSELs in BM (Ratajczak et al, 2011a).

Ideally, it would be beneficial to be able to isolate and purify stem and/or precursor cells from a subject that could be purified and/or manipulated in vitro before being reintroduced into the subject for treatment purposes. The use of a subject's own cells would obviate the need to employ adjunct immunosuppressive therapy, thereby maintaining the competency of the subject's immune system.

Thus, the search for other stem cell types from adult animals continues. For example, mesenchymal stem cells (MSCs) are one such cell type. MSCs have been shown to have the potential to differentiate into several lineages including bone (Haynesworth et al., 1992), cartilage (Mackay et al., 1998; Yoo et al, 1998), adipose tissue (Pittenger et al., 2000), tendon (Young et al, 1998), muscle, and stroma (Caplan et al., 2001. Another stem cell type is referred to as very small embryonic-like stem cells (VSELs), which are $CD45^-$ cells that are described in PCT International Patent Application Publication No. WO 2007/067280 (see also Kucia et al., 2006; U.S. Patent Application Publication No. 2009/0220466). A further stem cell type is referred to as hematopoietic stem/progenitor cells (HSPCs), which are found in muscle tissue and that originate in the bone marrow (see Kawada & Ogawa, 2001; Geiger et al, 2002; McKinney-Freeman et al, 2002; U.S. Pat. No. 8,859,282). These and other stem cells types can be used for various purposes, including but not limited to treatment of diseases and disorders that affect hematopoiesis and/or can be employed to generate cell types, tissues, and organs of interest by in vitro and/or in vivo differentiation.

SUMMARY

This Summary lists several embodiments of the presently disclosed subject matter, and in many cases lists variations and permutations of these embodiments of the presently disclosed subject matter. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

In some embodiments, the presently disclosed subject matter relates to methods for isolating subpopulations of stem cells from population of cells suspected of comprising the stem cells. In some embodiments, the methods comprise providing a population of $CD34^+$ human cells or $Sca-1^+$ murine cells suspected of stem cells; and selecting from the population of cells a subset of cells that are positive for a gene product selected from the group consisting of follicle-stimulating hormone receptor (FSHR), luteinizing hormone/choriogonadotropin receptor (LHCGR), prolactin receptor (PRLR), androgen receptor (AR), estrogen receptor α (ESRα), estrogen receptor β (ESRβ), and progesterone receptor (PGR); and are negative for each of CD45R/B220, Gr-1, TCRαβ, TCRγδ, CD11b, and Ter-119. In some embodiments, the methods optionally comprise fractioning the subset of cells into a $CD45^-$ fraction and a $CD45^+$ fraction, whereby a subpopulation of $CD45^-$ stem cells and/or a subpopulation of $CD45^+$ stem cells is isolated. In some embodiments, the selecting comprises contacting the cells of the population of cells with a plurality of antibodies, each antibody of the plurality binding to a gene product selected from the group consisting of CD34/Sca-1, FSHR, LHCGR, PRLR, AR, ESRα, ESRβ, PGR, CD45R/B220, Gr-1, TCRαβ, TCRγδ, CD11b, and Ter-119, and optionally also CD45. In some embodiments, one or more of the antibodies comprise a detectable label, are immobilized on a substrate, or any combination thereof. In some embodiments, the detectable label comprises a fluorescent label or a moiety that can be detected by a reagent comprising a fluorescent label. In some embodiments, the selecting comprises FACS sorting. In some embodiments, the methods further comprise isolating those cells that are $CD45^-$, $c-met^+$, $c-kit^+$, and/or $LIF-R^+$. In some embodiments, the methods further comprise isolating those $CD45^-$ cells that express one or more genes selected from the group consisting of SSEA-1, Oct-4, Rev-1, and Nanog. In some embodiments, the population of cells comprises a bone marrow sample, an umbilical cord blood sample, or a peripheral blood sample. In some embodiments, the population of cells is isolated from peripheral blood of a subject subsequent to treating the subject with an amount of a mobilizing agent sufficient to mobilize the $CD45^-$ and/or $CD45^+$ stem cells from bone marrow into the peripheral blood of the subject. In some embodiments, the mobilizing agent comprises at least one of granulocyte-colony stimulating factor (G-CSF) and a CXCR4 antagonist. In some embodiments, the CXCR4 antagonist is a T140 peptide. In some embodiments, the subject is a human. In some embodiments, the methods further comprise contacting the subpopulation of stem cells with an antibody that binds to CXCR4 and isolating from the subpopulation of stem cells those cells that are $CXCR4^+$. In some embodiments, the methods further comprise isolating those cells that are $CXCR4^+$ and/or $AC133^+$.

The presently disclosed subject matter also relates in some embodiments to populations of stem cells isolated by the presently disclosed methods.

The presently disclosed subject matter also relates in some embodiments to compositions comprising the populations of stem cells disclosed herein in pharmaceutically acceptable carriers. In some embodiments, the pharmaceutically acceptable carriers are pharmaceutically acceptable for use in humans.

The presently disclosed subject matter also relates in some embodiments to methods for expanding stem cells. In some embodiments, the presently disclosed methods comprise providing a purified population of $CD45^-$ or $CD45^+$ stem cells isolated by the presently disclosed methods; and growing the purified population of $CD45^-$ or $CD45^+$ stem cells in culture in the presence of one or more pituitary or gonadal sex hormones; and a suboptimal dose of hematopoietic cytokines and growth factors under conditions and for a time sufficient to expand the $CD45^-$ or $CD45^+$ stem cells. In some embodiments, the purified population of $CD45^-$ or $CD45^+$ stem cells is a population of $CD45^+$ hematopoietic stem/progenitor cells (HSPCs), $CD45^+$ mesenchymal stromal cells (MSCs), or a combination thereof, and/or is a population of $CD45^-$ very small embryonic-like stem cells (VSELs), and further wherein the HSPCs and/or the MSCs and/or the VSELs are human HSPCs and/or MSCs and/or VSELs. In some embodiments, the one or more pituitary or gonadal sex hormones are selected from the group consisting of FSHR, LHCGR, PRLR, AR, ESRα, ESRβ, and PGR.

The presently disclosed subject matter also relates in some embodiments to methods for stimulating proliferation of mesenchymal stromal cells (MSCs). In some embodiments, the methods comprise growing a population of MSCs in culture in the presence of one or more pituitary or gonadal sex hormones and suboptimal doses of hematopoietic cytokines and growth factors under conditions and for a time sufficient to stimulate proliferation of the MSCs. In some embodiments, the one or more pituitary or gonadal sex hormones are pituitary or gonadal sex hormones that bind to FSHR, LHCGR, PRLR, AR, ESRα, ESRβ, or PGR. In some embodiments, a pituitary or gonadal sex hormone that binds to FSHR, LHCGR, PRLR, AR, ESRα, ESRβ, or PGR is a follicle-stimulating hormone (FSH), a luteinizing hormone (LH), a prolactin hormone (PRL), an androgen, an estrogen, or a progesterone (PG), and/or is a precursor or metabolite thereof.

The presently disclosed subject matter also relates in some embodiments to methods for treating a subject suffering from exposure to radiation. In some embodiments, the methods comprise administering to the subject an amount of a population of stem cells as disclosed herein sufficient to ameliorate at least symptom or consequence of the exposure to the radiation. In some embodiments, the methods comprise administering to a subject an amount of FSH and/or LH sufficient to ameliorate at least symptom or consequence of the exposure to the radiation.

The presently disclosed subject matter also relates in some embodiments to methods for producing gametes in vitro. In some embodiments, the methods comprise providing a population of VSELs isolated from bone marrow; and contacting the VSELs in vitro with an amount of FSH and/or LH sufficient to induce differentiation of the VSELs and/or their progeny cells to gametes.

An object of the presently disclosed subject matter having been stated hereinabove, and which is achieved in whole or in part by the presently disclosed subject matter, other objects will become evident as the description proceeds when taken in connection with the accompanying drawings as best described herein below.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 1A-1D depict the results of experiments showing that human HSPCs and VSELs purified from umbilical blood (UCB) expressed functional SexH receptors. FIG. 1A shows the results of reverse transcription polymerase chain reaction (RT-PCR; n=2) for SexH (pituitary and gonadal) receptor expression in purified mRNA samples from sorted HSPCs (CD34$^+$Lin$^-$CD45$^+$, Lane 1) and VSELs (CD34$^+$Lin$^-$CD45$^-$, Lane 2) isolated from human UCB. Samples with water only instead of cDNA were used as negative controls (Lane 3). A representative agarose gel of the RT-PCR amplicons is shown. FIG. 1B shows that expression of the pituitary SexH receptors FSHR (top two panels) and LHR (bottom two panels) and the gonadal SexH receptors AR (top to panels) and ESRα (bottom two panels) was detected on both human CD133$^+$ VSELs and corresponding CD133$^+$ cells enriched for HSPCs by immunofluorescence staining (n=2), as described below in Materials and Methods of the EXAMPLES. FIG. 1C shows the effect of pituitary and gonadal SexHs on phosphorylation of p42/44 MAPK and AKT (Ser473) in CD34$^+$ HSPCs. These cells were enriched from UCB by immunomagnetic microbeads and starved for 5 hours in RPMI medium containing 0.5% BSA in an incubator and afterwards stimulated by SexHs for 5 minutes before collecting protein lysates. One set of representative blots out of two is shown. FIG. 1D is series of plots of densitometric analysis of blots shown in FIG. 1C. The experiment was repeated twice on isolated cells with similar results, and representative images are shown. An example of control staining is shown in FIG. 5B. Abbreviations: FSHR, follicle-stimulating hormone receptor; LHR, luteinizing hormone/choriogonadotropin receptor; AR, androgen receptor; ESR, estrogen receptor; PGR, progesterone receptor; SexHs, sex hormones; MNCs, mononuclear cells; VSELs, very small embryonic-like stem cells; HSPCs, hematopoietic stem/progenitor cells.

FIG. 4A shows the results of reverse transcription polymerase chain reaction (RT-PCR; n=2) for SexH (pituitary and gonadal) receptor expression in purified mRNA samples from cultured UCB-derived MSCs (Lane 1) and human ovarian cancer cell line cells (hOCCs) employed as positive control (Lane 2). Samples with water only instead of cDNA template were used as negative controls (Lane 3). A representative agarose gel of the RT-PCR amplicons is shown. Expression of these SexH receptors was also confirmed on human MSCs by immunofluorescence staining (see FIG. 5A) (n=2). FIG. 4B shows the effect of pituitary and gonadal SexHs on the phosphorylation of p42/44 MAPK and AKT (Ser473) in human UCB-derived MSCs, which were starved for 16 hours in DMEM medium containing 0.5% BSA in an incubator and afterwards stimulated by SexHs (FSH [10 IU/mL], LH [10 IU/mL], PRL [2 µg/mL], estradiol [0.1 µM], or danazol [4 mg/mL]) for 5 minutes before collecting protein lysates. One set of representative blots out of two is shown. FIG. 4C is a series of bar graphs showing the results of densitometric analysis of blots shown in FIG. 4B. The experiment was repeated twice on isolated cells with similar results, and representative images are shown.

FIG. 6A is a bar graph showing changes in the number of fibroblasts colony-forming units (CFU-F) in vitro from human UCB-derived MSCs plated at limiting dilution conditions in the presence of the indicated SexHs for 10 days. MSCs were seeded into six-well culture plates in DMEM medium supplied with 20% FBS, alone or with SexHs (FSH [10 IU/mL], LH [10 IU/mL], PRL [2 µg/mL], estradiol [0.1 µM], or danazol [4 mg/mL]). After 10 days, the cells were washed with PBS twice, stained using a FISHER HEALTHCARE™ PROTOCOL™ HEMA 3™ brand staining kit, and the colonies were counted. Experiments were repeated thrice with similar results. The data are normalized to CFU-F of non-stimulated cells, which was assumed to be 100%. Data from two separate experiments (each in duplicate) is presented as means±SD, and *p<0.05 and **p<0.05 are significant. FIG. 6B is a series of representative images of stained CFU-F colonies. FIG. 6C is a bar graph showing the effect of pituitary and gonadal hormones on the migration of human MSCs. The data are normalized to chemotaxis in response to medium alone, which was assumed to be 100%. Data from two separate experiments (each in triplicate) are combined together and shown as means±SD. *p<0.05 versus the control. FIG. 6D is a bar graph showing the effect of pituitary and gonadal hormones on the adhesion of human MSCs to fibronectin. The data are normalized to adhesion of non-stimulated cells, which was assumed to be 100%. Data from two separate experiments (each in triplicate) are combined together and shown as means±SD.

FIG. 7A is a bar graph showing an increase in expression of hVEGF2 at mRNA level in human MSCs stimulated by FSH (10 IU/mL) for 12 and 24 hours in vitro compared with unstimulated control cells. FIG. 7B is a series of photomicrographs showing capillary-like structure formation in 3D-Matrigel cultures in vitro (tube-formation assay). The assay was done on HUVECs seeded on Matrigel cultures in the presence of either conditioned medium (CM) from unstimulated MSCs, FSH (10 IU/mL)

alone, or CM from MSCs stimulated with the same concentration of FSH. As a positive control, human recombinant FGF2 (100 ng/mL) was used. FIG. 7C is a bar graph showing the results relative to tube formation by HUVECs stimulated with 0.5% BSA only, which was assumed to be 100%. The experiment was repeated twice independently with the same results, and the combined data are shown. For statistical comparisons, a one-way analysis of variance was carried out and means±SD are shown. Significance level: *p<0.05 versus control.

FIG. 8A is a series of bar graphs showing real time polymerase chain reaction (RQ-PCR) results for SexHs receptor expression in purified murine HSPCs and VSELs isolated from female (black bars) and male (gray bars) mice. The relative expression level is represented as the fold difference to the value of MNCs and shown as the mean±SD from at least three independent experiments on different samples of sorted VSELs, HSPCs, and MNCs. *p<0.05. FIG. 8B show the effect of pituitary SexHs on phosphorylation of p42/44 MAPK (Panels a and b) and AKT (Panel c) in murine BM-purified Sca-1$^+$ cells. Cells were stimulated by SexHs for 5 minutes (Panel a) or 10 minutes (Panels b and c). One representative blot out of two is shown. FIG. 8C show the effects of gonadal SexHs on phosphorylation of p42/44 MAPK and AKT in murine BM-purified Sca-1$^+$ cells from ovariectomized females (left) and normal males (right). One set of representative blots out of two is shown. FIG. 8D is a series of fluorescent images showing expression of pituitary SexHs receptors—FSH-R (Panel a) and LH-R (Panel b) and gonadal SexHs receptors Androgen-R (Panel c) and Estrogen-R (Panel d) detected on purified by FACS from BM murine HSPCs and VSELs by immunohistochemical staining. Experiment has been repeated twice on sorted cells with similar results, and representative pictures are shown. An example of control staining is provided in FIG. 13 for comparison. BM, bone marrow; FSH-R, follicle-stimulating hormone receptors; HSPCs, hematopoietic stem progenitor cells; LH-R, luteinizing hormone/choriogonadotropin receptor; SexHs, sex hormones; VSELs, very small embryonic-like stem cells.

FIG. 9A depicts the results of incorporation of BrdU into HSPCs and VSELs in murine BM (shown in gray) in response to 10-day administration of SexHs in vivo. The percentage of cells that showed proliferative activity and incorporated BrdU is shown in light gray. The percentage of cells that did not proliferate (BrdU-negative) is shown in black. *p<0.01; **p<0.001 compared with control group. FIG. 9B show the results of the experiment of FIG. 9A repeated with ovariectomized females. The percentage of cells that showed proliferative activity and incorporated BrdU is shown in light gray. The percentage of cells that did not proliferate (BrdU-negative) is shown in black. *p<0.05 compared with control group. FIG. 9C depicts changes in the total number of BM VSELs and HSPCs after prolonged administration of SexHs for 10 days. Experiments were repeated thrice with similar results. *p<0.05 compared with control. BrdU, bromodeoxyuridine.

BRIEF DESCRIPTION OF THE SEQUENCE LISTING

Figure 2:
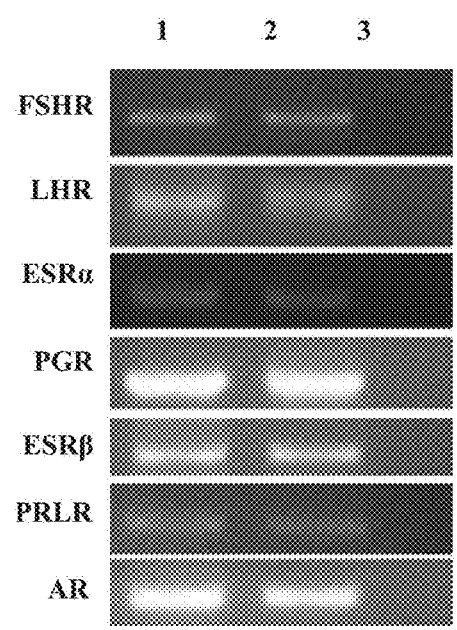
FIG. 2 shows that human CD34$^+$ cells purified from peripheral blood (PB) expressed functional SexH receptors. Reverse transcription polymerase chain reaction (n=2) for the expression of pituitary and gonadal SexH receptors after mRNA purification from PB CD34$^+$ cells from a normal donor (Lane 1) and a mobilized donor (Lane 2). Samples containing water only instead of cDNA were used as negative controls (Lane 3). Representative agarose gel of RT-PCR amplicons is shown.

SEQ ID NOs: 1 and 2 are exemplary sense and antisense oligonucleotides, respectively, that can be employed for amplifying and/or detecting nucleic acids derived from the human follicle-stimulating hormone receptor (FSHR) locus (e.g., Accession No. NM_000145 of the GENBANK® biosequence database).

SEQ ID NOs: 3 and 4 are exemplary sense and antisense oligonucleotides, respectively, that can be employed for amplifying and/or detecting nucleic acids derived from the human luteinizing hormone/choriogonadotropin receptor (LHCGR) locus (e.g., Accession No. NM_000233 of the GENBANK® biosequence database).

SEQ ID NOs: 5 and 6 are exemplary sense and antisense oligonucleotides, respectively, that can be employed for amplifying and/or detecting nucleic acids derived from the human prolactin receptor (PRLR) locus (e.g., Accession No. NM_000949 of the GENBANK® biosequence database).

SEQ ID NOs: 7 and 8 are exemplary sense and antisense oligonucleotides, respectively, that can be employed for amplifying and/or detecting nucleic acids derived from the human androgen receptor (AR) locus (e.g., Accession No. NM_000044 of the GENBANK® biosequence database).

SEQ ID NOs: 9 and 10 are exemplary sense and antisense oligonucleotides, respectively, that can be employed for amplifying and/or detecting nucleic acids derived from the human estrogen receptor α (ERSα) locus (e.g., Accession No. NM_000125 of the GENBANK® biosequence database).

SEQ ID NOs: 11 and 12 are exemplary sense and antisense oligonucleotides, respectively, that can be employed for amplifying and/or detecting nucleic acids derived from the human estrogen receptor β (ESRβ) locus (e.g., Accession No. NM_001291723 of the GENBANK® biosequence database).

SEQ ID NOs: 13 and 14 are exemplary sense and antisense oligonucleotides, respectively, that can be employed for amplifying and/or detecting nucleic acids derived from the human progesterone receptor (PGR) locus (e.g., Accession No. NM_001202474 of the GENBANK® biosequence database).

SEQ ID NOs: 15 and 16 are exemplary sense and antisense oligonucleotides, respectively, that can be employed for amplifying and/or detecting nucleic acids derived from the human vascular endothelial growth factor A (VEGFA/VEGF2) locus (e.g., Accession No. NM_001025366 of the GENBANK® biosequence database).

SEQ ID NOs: 17 and 18 are exemplary sense and antisense oligonucleotides, respectively, that can be employed for amplifying and/or detecting nucleic acids derived from the human beta-2-microglobulin (B2M) locus (e.g., Accession No. NM_004048 of the GENBANK® biosequence database).

SEQ ID NOs: 19 and 20 are exemplary sense and antisense oligonucleotides, respectively, that can be employed for amplifying and/or detecting nucleic acids derived from the murine follicle-stimulating hormone receptor (FSHR) locus (e.g., Accession No. NM_013523 of the GENBANK® biosequence database).

SEQ ID NOs: 21 and 22 are exemplary sense and antisense oligonucleotides, respectively, that can be employed for amplifying and/or detecting nucleic acids derived from the murine luteinizing hormone receptor (LHR) locus (e.g., Accession No. NM_013582 of the GENBANK® biosequence database).

SEQ ID NOs: 23 and 24 are exemplary sense and antisense oligonucleotides, respectively, that can be employed for amplifying and/or detecting nucleic acids derived from the murine prolactin receptor (PRLR) locus (e.g., Accession No. NM_011169 of the GENBANK® biosequence database).

SEQ ID NOs: 25 and 26 are exemplary sense and antisense oligonucleotides, respectively, that can be employed for amplifying and/or detecting nucleic acids derived from the murine androgen receptor (AR) locus (e.g., Accession No. NM_013476 of the GENBANK® biosequence database).

SEQ ID NOs: 27 and 28 are exemplary sense and antisense oligonucleotides, respectively, that can be employed for amplifying and/or detecting nucleic acids derived from the murine estrogen receptor 1 (ESR1) locus (e.g., Accession No. NM_007956 of the GENBANK® biosequence database).

SEQ ID NOs: 29 and 30 are exemplary sense and antisense oligonucleotides, respectively, that can be employed for amplifying and/or detecting nucleic acids derived from the murine estrogen receptor 2 (ESR2) locus (e.g., Accession No. NM_207707 of the GENBANK® biosequence database).

SEQ ID NOs: 31 and 32 are exemplary sense and antisense oligonucleotides, respectively, that can be employed for amplifying and/or detecting nucleic acids derived from the murine progesterone receptor (PGR) locus (e.g., Accession No. NM_008829 of the GENBANK® biosequence database).

TABLE 1

Summary of Exemplary RT-PCR Primers for Human Gene Products

| GENE NAME | PRIMER | SEQUENCES* | PRODUCT (bp) |
|---|---|---|---|
| FSHR | Fwd | 5'-gcttctgagatctgtggaggtt-3' (SEQ ID NO: 1) | 231 |
|  | Rev | 5'-ggacaaacctcagttcaatggc-3' (SEQ ID NO: 2) |  |
| LHCGR | Fwd | 5'-cagaggccgtccaagacac-3' (SEQ ID NO: 3) | 330 |
|  | Rev | 5'-atgctccgggctcaatgtat-3' (SEQ ID NO: 4) |  |
| PRLR | Fwd | 5'-gagatcttctcacagagcca-3' (SEQ ID NO: 5) | 291 |
|  | Rev | 5'-aagttcacttcagggttcatgtgg-3' (SEQ ID NO: 6) |  |
| AR | Fwd | 5'-cgacttcaccgcacctgatg-3' (SEQ ID NO: 7) | 296 |
|  | Rev | 5'-acttctgtttccatcagcgg-3' (SEQ ID NO: 8) |  |
| ESR1 | Fwd | 5'-aggtgccctactacctggag-3' (SEQ ID NO: 9) | 397 |
|  | Rev | 5'-cggtcttttcgtatcccacct-3' (SEQ ID NO: 10) |  |
| ER beta | Fwd | 5'-aatggtgaagtgtggctccc-3' (SEQ ID NO: 11) | 345 |
|  | Rev | 5'-acttggtcgaacaggctgag-3' (SEQ ID NO: 12) |  |
| PGR | Fwd | 5'-tcaactacctgaggccggat-3' (SEQ ID NO: 13) | 336 |
|  | Rev | 5'-cagcatccagtgctctcaca-3' (SEQ ID NO: 14) |  |
| VEGFA/ VEGF2 | Fwd | 5'-ggtctcgattggatggcagtag-3' (SEQ ID NO: 15) | 91 |
|  | Rev | 5'-cacccatggcagaaggagga-3' (SEQ ID NO: 16) |  |
| B2M | Fwd | 5'-aatgcggcatcttcaaacct-3' (SEQ ID NO: 17) | 59 |
|  | Rev | 5' tgactttgtcacagcccaagata-3' (SEQ ID NO: 18) |  |

*Sequences are presented in the 5' to 3' direction.

TABLE 2

Summary of Exemplary RT-PCR Primers for Murine Gene Products

| GENE NAME | | PRIMER SEQUENCES* | PRODUCT (bp) |
|---|---|---|---|
| FSHR | Fwd | 5'-tcaacggaacccagctagatg-3' (SEQ ID NO: 19) | 104 |
| | Rev | 5'-gtctaaaacgactggcccagag-3' (SEQ ID NO: 20) | |
| LHR | Fwd | 5'-atctgtaacacaggcatccgg-3' (SEQ ID NO: 21) | 115 |
| | Rev | 5'-cgttccctggtatggtggttat-3' (SEQ ID NO: 22) | |
| PRLR | Fwd | 5'-tgcttgctgggaagtacgg-3' (SEQ ID NO: 23) | 237 |
| | Rev | 5'-ggtgacggagatagttgggg-3' (SEQ ID NO: 24) | |
| AR | Fwd | 5'-gactgcatgtacgcgtcgc-3' (SEQ ID NO: 25) | 156 |
| | Rev | 5'-ggcgtaacctccatgaaagag-3' (SEQ ID NO: 26) | |
| ESR1 | Fwd | 5'-gccaaggagactcgctactgtg-3' (SEQ ID NO: 27) | 157 |
| | Rev | 5'-tgtcaatggtgcattggtttgt-3' (SEQ ID NO: 28) | |
| ER2 | Fwd | 5'-taccccttggctaccgcaa-3' (SEQ ID NO: 29) | 151 |
| | Rev | 5'-gcatcaggaggttggccag-3' (SEQ ID NO: 30) | |
| PGR | Fwd | 5'-aatggaagggcagcacaact-3' (SEQ ID NO: 31) | 60 |
| | Rev | 5'-gcggattttatcaacgatgca-3' (SEQ ID NO: 32) | |

*Sequences are presented in the 5' to 3' direction.

DETAILED DESCRIPTION

Evidence has accumulated that murine hematopoietic stem/progenitor cells (HSPCs) share several markers with the germline, a connection supported by recent reports that pituitary and gonadal sex hormones (SexHs) regulate development of murine HSPCs. It has also been reported that human HSPCs, like their murine counterparts, respond to certain SexHs (e.g., androgens). However, to better address the effects of SexHs, particularly pituitary SexHs, on human hematopoiesis, expression of receptors for pituitary SexHs, including follicle-stimulating hormone (FSH), luteinizing hormone (LH), and prolactin (PRL), as well as the receptors for gonadal SexHs, including progesterone, estrogens, and androgen, was investigated on HSPCs purified from human umbilical cord blood (UCB) and peripheral blood (PB). The functionality of these receptors in ex vivo signal transduction studies and in vitro clonogenic assays was then tested. In parallel, the effects of SexHs on human mesenchymal stromal cells (MSCs) was tested. And finally, based on the observation that at least some of the UCB-derived, CD45⁻ very small embryonic-like stem cells (VSELs) become specified into CD45⁺ HSPCs, the expression of pituitary and gonadal SexH receptors on these cells was also evaluated. As such, disclosed herein for the first time is the observation that human HSPCs and VSELs, like their murine counterparts, express pituitary and gonadal SexH receptors at the mRNA and protein levels. Most importantly, if added to suboptimal doses of hematopoietic cytokines and growth factors, SexH enhance clonogenic growth of human HSPCs as well as directly stimulate proliferation of MSCs.

Thus, to shed more light on the role of SexHs in human hematopoiesis, the expression of receptors for pituitary- and gonad-derived SexHs on human umbilical cord blood (UCB)- and peripheral blood (PB)-purified HSPCs and the functionality of these receptors in ex vivo signal transduction studies and clonogenic assays were tested. In parallel, the effect of SexHs on the proliferation of human mesenchymal stromal cells (MSCs) was tested, and the expression of SexH receptors on human UCB-derived CD133⁺/Lin⁻/CD45⁻ cell populations highly enriched in VSELs was evaluated.

As set forth herein, human CD45⁺ HSPCs and CD45⁻ VSELs, like their murine counterparts, express pituitary and gonadal SexH receptors at the mRNA and protein levels. Most importantly, SexH co-stimulate clonogenic growth of human HSPCs if added to suboptimal doses of hematopoietic cytokines and growth factors as well as directly stimulate proliferation of MSCs.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Furthermore, the terms first, second, third, and the like as used herein are employed for distinguishing between similar elements and not necessarily for describing a sequential or chronological order. It is to be understood that the terms so used are interchangeable under appropriate circumstances and that the subject matter described herein is capable of operation in other sequences than described or illustrated herein.

Following long-standing patent law convention, the articles "a", "an", and "the" refer to "one or more" when used in this application, including in the claims. For example, the phrase "a cell" refers to one or more cells. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the phrase "biological sample" refers to a sample isolated from a subject (e.g., a biopsy, blood, serum, etc.) or from a cell or tissue from a subject (e.g., RNA and/or DNA and/or a protein or polypeptide isolated therefrom). Biological samples can be of any biological tissue or fluid or cells from any organism as well as cells cultured in vitro, such as cell lines and tissue culture cells. Frequently the sample will be a "clinical sample" which is a sample derived from a subject (i.e., a subject undergoing a diagnostic procedure and/or a treatment). Typical clinical samples include, but are not limited to cerebrospinal fluid, serum, plasma, blood, saliva, skin, muscle, olfactory tissue, lacrimal fluid, synovial fluid, nail tissue, hair, feces, urine, a tissue or cell type, and combinations thereof, tissue or fine needle biopsy samples, and cells therefrom. Biological samples can also include sections of tissues, such as frozen sections or formalin fixed sections taken for histological purposes.

As used herein, term "comprising", which is synonymous with "including," "containing", or "characterized by", is inclusive or open-ended and does not exclude additional, unrecited elements and/or method steps. "Comprising" is a term of art used in claim language which means that the named elements are present, but other elements can be added and still form a composition or method within the scope of the presently disclosed subject matter. By way of example and not limitation, a pharmaceutical composition comprising human MSCs and/or progeny cells thereof and a pharmaceutically acceptable carrier can also contain other components including, but not limited to other cells and cell types, other carriers and excipients, and any other molecule that might be appropriate for inclusion in the pharmaceutical composition without any limitation.

As used herein, the phrase "consisting of" excludes any element, step, or ingredient that is not particularly recited in the claim. When the phrase "consists of" appears in a clause of the body of a claim, rather than immediately following the preamble, it limits only the element set forth in that clause; other elements are not excluded from the claim as a whole. By way of example and not limitation, a pharmaceutical composition consisting of human MSCs and/or progeny cells thereof and a pharmaceutically acceptable carrier contains no other components besides the human MSCs and/or progeny cells thereof and the pharmaceutically acceptable carrier. It is understood that any molecule that is below a reasonable level of detection is considered to be absent.

As used herein, the phrase "consisting essentially of" limits the scope of a claim to the specified materials or steps, plus those that do not materially affect the basic and novel characteristic(s) of the claimed subject matter. By way of example and not limitation, a pharmaceutical composition consisting essentially of human MSCs and/or progeny cells thereof and a pharmaceutically acceptable carrier contains the human MSCs and/or progeny cells thereof and the pharmaceutically acceptable carrier, but can also include any additional elements that might be present but that do not materially affect the biological functions of the composition in vitro or in vivo.

With respect to the terms "comprising", "consisting essentially of", and "consisting of", where one of these three terms is used herein, the presently disclosed and claimed subject matter encompasses the use of either of the other two terms. For example, "comprising" is a transitional term that is broader than both "consisting essentially of" and "consisting of", and thus the term "comprising" implicitly encompasses both "consisting essentially of" and "consisting of". Likewise, the transitional phrase "consisting essentially of" is broader than "consisting of", and thus the phrase "consisting essentially of" implicitly encompasses "consisting of".

As used herein, the term "isolated" when referring to cells or a cell population refers to cells or a cell population collected from a subject, in some embodiments a mammalian subject, and in some embodiments a human. Typically, collection of the desired cells or cell population is achieved based on detection of one or more cell markers, such as but not limited to antibody-based detection.

As used herein, a cell exists in a "purified form" when it has been isolated away from all other cells that exist in its native environment, but also when the proportion of that cell in a mixture of cells is greater than would be found in its native environment. Stated another way, a cell is considered to be in "purified form" when the population of cells in question represents an enriched population of the cell of interest, even if other cells and cell types are also present in the enriched population. A cell can be considered in purified form when it comprises in some embodiments at least about 10% of a mixed population of cells, in some embodiments at least about 20% of a mixed population of cells, in some embodiments at least about 25% of a mixed population of cells, in some embodiments at least about 30% of a mixed population of cells, in some embodiments at least about 40% of a mixed population of cells, in some embodiments at least about 50% of a mixed population of cells, in some embodiments at least about 60% of a mixed population of cells, in some embodiments at least about 70% of a mixed population of cells, in some embodiments at least about 75% of a mixed population of cells, in some embodiments at least about 80% of a mixed population of cells, in some embodiments at least about 90% of a mixed population of cells, in some embodiments at least about 95% of a mixed population of cells, and in some embodiments about 100% of a mixed population of cells, with the proviso that the cell comprises a greater percentage of the total cell population in the "purified" population that it did in the population prior to the purification. In this respect, the terms "purified" and "enriched" can be considered synonymous.

The term "subject" as used herein refers to a member of any invertebrate or vertebrate species. Accordingly, the term "subject" is intended to encompass any member of the Kingdom Animalia including, but not limited to the phylum Chordata (i.e., members of Classes Osteichythyes (bony fish), Amphibia (amphibians), Reptilia (reptiles), Aves (birds), and Mammalia (mammals)), and all Orders and Families encompassed therein.

Similarly, all genes, gene names, and gene products disclosed herein are intended to correspond to homologs from any species for which the compositions and methods disclosed herein are applicable. Thus, the terms include, but are not limited to genes and gene products from humans and mice. It is understood that when a gene or gene product from a particular species is disclosed, this disclosure is intended to be exemplary only, and is not to be interpreted as a limitation unless the context in which it appears clearly indicates. Thus, for example, for the genes listed in Table 1 above, which disclose Accession Nos. for various gene products disclosed in the GENBANK® biosequence database for the human gene products, are intended to encompass homologous genes and gene products from other animals including but not limited to other mammals, fish, amphibians, reptiles, and birds.

The methods of the presently disclosed subject matter are particularly useful for warm-blooded vertebrates. Thus, the presently disclosed subject matter concerns mammals and birds. More particularly contemplated is the isolation, manipulation, and use of stem cells from mammals such as humans and other primates, as well as those mammals of importance due to being endangered (such as Siberian tigers), of economic importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), rodents (such as mice, rats, and rabbits), marsupials, and horses. Also provided is the use of the disclosed methods and compositions on birds, including those kinds of birds that are endangered, kept in zoos, as well as fowl, and more particularly domesticated fowl, e.g., poultry, such as turkeys, chickens, ducks, geese, guinea fowl, and the like, as they are also of economic importance to humans. Thus, also contemplated is the isolation, manipulation, and use of stem cells from livestock, including but not limited to domesticated swine (pigs and hogs), ruminants, horses, poultry, and the like.

As used herein, the phrase "substantially" refers to a condition wherein in some embodiments no more than 50%, in some embodiments no more than 40%, in some embodiments no more than 30%, in some embodiments no more than 25%, in some embodiments no more than 20%, in some embodiments no more than 15%, in some embodiments no more than 10%, in some embodiments no more than 9%, in some embodiments no more than 8%, in some embodiments no more than 7%, in some embodiments no more than 6%, in some embodiments no more than 5%, in some embodiments no more than 4%, in some embodiments no more than 3%, in some embodiments no more than 2%, in some embodiments no more than 1%, and in some embodiments no more than 0% of the components of a collection of entities does not have a given characteristic.

As used herein, the phrase "cell surface marker" refers not only for a protein expressed on the surface of a cell but also any carbohydrate, lipid, or any other target that is detectable using specific antibodies or any other standard detection method. Typical cell surface markers that can be useful in the presently disclosed subject matter include, but are not limited to, the major histocompatibility complex (MHC); SSEA3; SSEA4; SSEA1; Tra-1-60; Tra-1-81; the clusters of differentiation (CD) antigens CD29, CD34, CD45, CD55, CD73, CD105, CD90, CD117 (c-kit), and CD133; and the receptors FSHR, LHCGR. PRLR, APPLICANTS RESPECTFULLY, ESR1/ESRα, ERβ, and PGR. However, other cellular markers described herein or known to the skilled person can also be employed.

The phrase "intracellular marker" as used herein refers to any gene or intracellular gene product that is detectable. Examples of intracellular markers include but are not limited to RNA, particularly mRNA derived from the Oct3 and/or Oct4, Nanog, Sox2, aldehyde dehydrogenase (ALDH), and any other loci. Intracellular markers can also include non-nucleic acid biomolecules including but not limited to being proteins, carbohydrates, and lipids.

The phrase "expression of [marker X]" as used herein when referring to a cell indicates that the cell expresses the marker at a level which is sufficient for detection using standard detection methods. Expression of a marker is also referred to as "positively expressing", "+", "positive", or "pos". The terms "not expressing [marker X]" as used herein when referring to a cell indicates that the cell does not express the marker at a level which is sufficient for detection, using standard detection methods. Absence of expression of a marker is also referred to as "negative expression", "−", "negative", and "neg".

For some markers, expression or absence of expression is often in fact based on comparison with other cells which also express the marker. For these markers determining positive or negative expression is based on a threshold. Methods for determining positive or negative expression based on thresholds are known to the person skilled in the art and typically involve calibrating based on a "negative control". Accordingly, it will be understood that for these markers, reference to positive expression in fact implies "elevated expression compared to negative controls" and "negative expression" in fact refers to "reduced expression compared to positive controls".

When referring to a cell population, reference is made to a population which "expresses [marker X]" where at least 10%, 20%, or 30% or 40%, 50%, or 60% or 70%, 80%, or 90% or 95%, 96%, 97%, 98%, 99%, or even 100% of the cells within the population express the cell markers of interest. By "substantially free" is intended less than about 25%, 20%, 15%, 10%, 9%, 8%, 7%, 6%, 5%, 4%, 3%, 2%, 1%, or even 0% of the cells in the population express the marker of interest.

II. Stem Cell Subpopulations and Methods for Isolating the Same

The presently disclosed subject matter provides methods for isolating subpopulations of stem cells from populations of cells suspected of comprising the stem cells. In some embodiments, the methods comprise providing a population of $CD34^+$ human cells or $Sca-1^+$ murine cells suspected of stem cells; and selecting from the population of cells a subset of cells that are positive for a gene product selected from the group consisting of follicle-stimulating hormone receptor (FSHR), luteinizing hormone/choriogonadotropin receptor (LHCGR), prolactin receptor (PRLR), androgen receptor (AR), estrogen receptor α (ESRα), estrogen receptor β (ESRβ), and progesterone receptor (PGR); and are negative for each of CD45R/B220, Gr-1, TCRαβ, TCRγδ, CD11b, and Ter-119. In some embodiments, the methods optionally comprise further fractioning the subset of cells into a $CD45^-$ fraction and a $CD45^+$ fraction.

Any methodology that can be used to separate cells that express a gene product of interest from those that do not can be employed in the methods of the presently disclosed subject matter. In some embodiments, the selecting step comprises contacting the population of cells with a series of antibodies, wherein the antibodies are detectably labeled (e.g., fluorescently labeled, labeled with biotin, etc.) and/or are immobilized on a solid support. In some embodiments, the separating step is performed by fluorescence-activated cell sorting (FACS).

By way of example and not limitation, a first antibody that can be used is one that is specific for CD34 in the case of human cells or Sca-1 in the case of murine cells. The CD34- or Sca-1-positive cell population can then be isolated and further fractionated with respect to any of FSHR, LHCGR/LHR, PRLR, AR, ESRα/ESR1, ESRβ/ESR2, and/or PGR, which are the receptors for FSH, LHCG/LH, PRL, androgen, estrogen, and progesterone, respectively (collectively referred to herein as "pituitary and gonadal sex hormones" or "SexHs") to identify the CD34$^+$/Sca-1$^+$ population that also expresses one to or more of these SexH receptors. Given that stem cells are typically also lineage-negative (lin$^-$), the lin$^-$ cells present in the CD34$^+$/Sca-1$^+$/SexH$^+$ subpopulation can be further fractionated by removing all cells that express one or more of CD45R/B220, Gr-1, TCRαβ, TCRγδ, CD11b, and Ter-119. Antibodies that target these markers can also be used simultaneously or serially to remove cells that express these markers.

And finally, the CD34$^+$/Sca-1$^+$/SexH$^+$/lin$^-$ subpopulation can be further fractionated into CD45$^+$ and CD45$^-$ subpopulations that contacting the CD34$^+$/Sca-1$^+$/SexH$^+$/lin$^-$ subpopulation with an antibody that is specific for CD45 and separating the CD45$^+$ and CD45$^-$ cells to establish a CD34$^+$/Sca-1$^+$, SexH$^+$, lin$^-$, and CD45$^+$ subpopulation enriched in hematopoietic stem/progenitor cells (HSPCs) and human mesenchymal stromal cells (MSCs) and a CD34$^+$/Sca-1$^+$, SexH$^+$, lin$^-$, and CD45$^-$ subpopulation enriched in very small embryonic-like stem cells (VSELs).

As used herein, the term "CD45" refers to a tyrosine phosphatase, also known as the leukocyte common antigen (LCA), and having the gene symbol PTPRC. This gene corresponds to GENBANK® Accession Nos. NP_002829 (human), NP_035340 (mouse), NP_612516 (rat), XP_002829 (dog), XP_599431 (cow) and AAR16420 (pig). The amino acid sequences of additional CD45 homologs are also present in the GENBANK® database, including those from several fish species and several non-human primates.

As used herein, the term "CD34" refers to a cell surface marker found on certain hematopoietic and non-hematopoietic stem cells, and having the gene symbol CD34. The GENBANK® database discloses amino acid and nucleic acid sequences of CD34 from humans (e.g., AAB25223), mice (NP_598415), rats (XP_223083), cats (NP_001009318), pigs (NP_999251), cows (NP_776434), and others. In mice, stem cells also express the stem cell antigen Sca-1 (GENBANK® Accession No. NP_034868), also referred to as Lymphocyte antigen Ly-6A.2.

As used herein, the term "FSHR" refers to the follicle stimulating hormone receptor locus, gene products derived from which are found on certain stem cells as disclosed herein. The GENBANK® biosequence database discloses amino acid sequences of FSHR from humans (e.g., NP_000136), mice (NP_038551), rats (NP_954707), cats (NP_001041479), pigs (NP_999551), cows (NP_776486), and others.

As used herein, the terms "LHCGR" and "LHR" refer to the lutropin-choriogonadotropic hormone receptor, also referred to as the luteinizing hormone receptor, gene products derived from which are found on certain stem cells as disclosed herein. The GENBANK® biosequence database discloses amino acid sequences of LHCGR from humans (e.g., NP_000224), mice (NP_038610), rats (NP_037110), cats (XP_011279385), pigs (NP_999314), cows (NP_776806), and others.

As used herein, the term "PRLR" refers to the prolactin receptor, gene products derived from which are found on certain stem cells as disclosed herein. The GENBANK® biosequence database discloses amino acid sequences of PRLR from humans (e.g., NP_000940), mice (NP_035299), rats (NP_001029283), cats (XP_003981512), pigs (NP_001001868), cows (NP_776580), and others.

As used herein, the term "AR" refers to the androgen receptor, gene products derived from which are found on certain stem cells as disclosed herein. The GENBANK® biosequence database discloses amino acid sequences of AR from humans (e.g., NP_000035), mice (NP_038504), rats (NP_036634), cats (XP_004000624), pigs (NP_999479), cows (NP_001231056), and others.

As used herein, the term "ESRα" refers to the estrogen receptor alpha (also called the estrogen receptor 1), gene products derived from which are found on certain stem cells as disclosed herein. The GENBANK® biosequence database discloses amino acid sequences of ESRα from humans (e.g., P03372), mice (BAJ65337), rats (BAI48013), cats (AAU11443), pigs (ABM88718), cows (AAS46251), and others.

As used herein, the term "ESRβ" refers to the estrogen receptor beta, gene products derived from which are found on certain stem cells as disclosed herein. The GENBANK® biosequence database discloses amino acid sequences of ESRβ from humans (e.g., NP_001035365), mice (NP_997590), rats (NP_036886), cats (XP_006932969), pigs (NP_001001533), cows (NP_776476), and others.

As used herein, the term "PGR" refers to the progesterone receptor, gene products derived from which are found on certain stem cells as disclosed herein. The GENBANK® biosequence database discloses amino acid sequences of PGR from humans (e.g., NP_001189403), mice (NP_032855), rats (NP_074038), cats (XP_011284806), pigs (NP_001159960), cows (NP_001192285), and others.

As used herein, lin$^-$ refers to a cell that does not express any of the following markers: CD45R/B220, Gr-1, TCRαβ, TCRγδ, CD11b, and Ter-119. These markers are found on cells of the B cell lineage from early Pro-B to mature B cells (CD45R/B220); cells of the myeloid lineage such as monocytes during development in the bone marrow, bone marrow granulocytes, and peripheral neutrophils (Gr-1); thymocytes, peripheral T cells, and intestinal intraepithelial lymphocytes (TCRαβ and TCRγδ); myeloid cells, NK cells, some activated lymphocytes, macrophages, granulocytes, B1 cells, and a subset of dendritic cells (CD11b); and mature erythrocytes and erythroid precursor cells (Ter-119).

The separation step can be performed in a stepwise manner as a series of steps or concurrently. For example, the presence or absence of each marker can be assessed individually, producing two subpopulations at each step based on whether the individual marker is present. Thereafter, the subpopulation of interest can be selected and further divided based on the presence or absence of the next marker.

Alternatively, the subpopulation can be generated by separating out only those cells that have a particular marker profile, wherein the phrase "marker profile" refers to a summary of the presence or absence of two or more markers. For example, a mixed population of cells can contain both CD34$^+$ and CD34$^-$ cells. Similarly, the same mixed population of cells can contain both CD45$^+$ and CD45$^-$ cells. Thus, certain of these cells will be CD34$^+$/CD45$^+$, others will be CD34$^+$/CD45$^-$, others will be CD34$^-$/CD45$^+$, and others will be CD34$^-$/CD45$^-$. Each of these individual combinations of markers represents a different marker profile. As additional markers are added, the profiles can become more complex and correspond to a smaller and smaller percentage of the original mixed population of cells.

In some embodiments, the cells of the presently disclosed subject matter have a marker profile of CD34$^+$/Sca-1$^+$, SexH$^+$, lin$^-$, and CD45$^+$, and in some embodiments, the cells of the presently disclosed subject matter have a marker profile of CD34$^+$/Sca-1$^+$, SexH$^+$, lin$^-$, and CD45$^-$.

In some embodiments of the presently disclosed subject matter, antibodies specific for markers expressed by a cell type of interest (e.g., polypeptides expressed on the surface of a CD34$^+$/Sca-1$^+$, SexH$^+$, lin$^-$, and CD45$^{+/-}$ cell) are employed for isolation and/or purification of subpopulations of BM cells and/or umbilical cord blood cells that have marker profiles of interest. It is understood that based on the marker profile of interest, the antibodies can be used to positively or negatively select fractions of a population, which in some embodiments are then further fractionated.

In some embodiments, a plurality of antibodies, antibody derivatives, and/or antibody fragments with different specificities is employed. In some embodiments, each antibody, or fragment or derivative thereof, is specific for a marker selected from the group consisting of Ly-6A/E (Sca-1), CD34, CD45, CD45R, B220, Gr-1, TCRαβ, TCRγδ, CD11b, Ter-119, FSHR, LHCGR, PRLR, AR, ESRα, ESRβ, and PGR.

In some embodiments, each antibody, or fragment or derivative thereof, comprises a detectable label. Different antibodies, or fragments or derivatives thereof, which bind to different markers can comprise different detectable labels or can employ the same detectable label.

A variety of detectable labels are known to the skilled artisan, as are methods for conjugating the detectable labels to biomolecules such as antibodies and fragments and/or derivatives thereof. As used herein, the phrase "detectable label" refers to any moiety that can be added to an antibody, or a fragment or derivative thereof that allows for the detection of the antibody. Representative detectable moieties include, but are not limited to, covalently attached chromophores, fluorescent moieties, enzymes, antigens, groups with specific reactivity, chemiluminescent moieties, and electrochemically detectable moieties, etc. In some embodiments, the antibodies are biotinylated. In some embodiments, the biotinylated antibodies are detected using a secondary antibody that comprises an avidin or streptavidin group and is also conjugated to a fluorescent label including but not limited to Cy3, Cy5, and Cy7. In some embodiments, the antibody, fragment, or derivative thereof is directly labeled with a fluorescent label such as Cy3, Cy5, or Cy7. In some embodiments, the antibodies comprise biotin-conjugated rat anti-mouse Ly-6A/E (Sca-1; clone E13-161.7), streptavidin-PE-Cy5 conjugate, anti-CD45-APCCy7 (clone 30-F11), anti-CD45R/B220-PE (clone RA3-6B2), anti-Gr-1-PE (clone RB6-8C5), anti-TCRαβ PE (clone H57-597), anti-TCRγδ PE (clone GL3), anti-CD11b PE (clone M1/70) and anti-Ter-119 PE (clone TER-119). In some embodiments, the antibody, fragment, or derivative thereof is directly labeled with a fluorescent label and cells that bind to the antibody are separated by fluorescence-activated cell sorting. Additional detection strategies are known to the skilled artisan.

While FACS scanning is a convenient method for purifying subpopulations of cells, it is understood that other methods can also be employed. An exemplary method that can be used is to employ antibodies that specifically bind to one or more of CD45, CD34, Sca-1, CD45R/B220, Gr-1, TCRαβ, TCRγδ, CD11b, Ter-119, FSHR, LHCGR, PRLR, AR, ESRα, ESRβ, and PGR, with the antibodies comprising a moiety (e.g., biotin) for which a high affinity binding reagent is available (e.g., avidin or streptavidin). For example, a biotin moiety could be attached to antibodies for each marker for which the presence on the cell surface is desirable (e.g., CD34, Sca-1, FSHR, LHCGR, PRLR, AR, ESRα, ESRβ, and PGR), and the cell population with bound antibodies could be contacted with an affinity reagent comprising an avidin or streptavidin moiety (e.g., a column comprising avidin or streptavidin). Those cells that bound to the column would be recovered and further fractionated as desired. Alternatively, the antibodies that bind to markers present on those cells in the population that are to be removed (e.g., CD45R/B220, Gr-1, TCRαβ, TCRγδ, CD11b, and Ter-119) can be labeled with biotin, and the cells that do not bind to the affinity reagent can be recovered and purified further.

It is also understood that different separation techniques (e.g., affinity purification and FACS) can be employed together at one or more steps of the purification process.

A population of cells containing the CD34$^+$/Sca-1$^+$, SexH$^+$, lin$^-$, and CD45$^{+/-}$ cells of the presently disclosed subject matter can be isolated from any subject or from any source within a subject that contains them. In some embodiments, the population of cells comprises a bone marrow sample, a cord blood sample, or a peripheral blood sample. In some embodiments, the population of cells is isolated from peripheral blood of a subject subsequent to treating the subject with an amount of a mobilizing agent sufficient to mobilize CD45$^-$ stem cells from bone marrow into the peripheral blood of the subject. As used herein, the phrase "mobilizing agent" refers to a compound (e.g., a peptide, polypeptide, small molecule, or other agent) that when administered to a subject results in the mobilization of a VSEL stem cell or a derivative thereof from the bone marrow of the subject to the peripheral blood. Stated another way, administration of a mobilizing agent to a subject results in the presence in the subject's peripheral blood of an increased number of VSEL stem cells and/or VSEL stem cell derivatives than were present therein immediately prior to the administration of the mobilizing agent. It is understood, however, that the effect of the mobilizing agent need not be instantaneous, and typically involves a lag time during which the mobilizing agent acts on a tissue or cell type in the subject in order to produce its effect. In some embodiments, the mobilizing agent comprises at least one of granulocyte-colony stimulating factor (G-CSF) and a CXCR4 antagonist (e.g., a T140 peptide; Tamamura et al, 1998).

In some embodiments, a stem cell or derivative thereof also expresses a marker selected from the group consisting of c-met, c-kit, LIF-R, and combinations thereof. In some embodiments, the disclosed isolation methods further comprise isolating those cells that are c-met$^+$, c-kit$^+$, and/or LIF-R$^+$.

In some embodiments, the stem cell or derivative thereof also expresses SSEA-1, Oct-4, Rev-1, and Nanog, and in some embodiments, the disclosed isolation methods further comprise isolating those cells that express these genes.

The presently disclosed subject matter also provides in some embodiments populations of SexH$^+$/CD45$^-$ stem cells and/or SexH$^+$/CD45$^+$ stem cells isolated by the presently disclosed methods.

III. Compositions of Stem Cells

III.A. Subjects

The presently disclosed subject matter also provides a method for treating subjects comprising administering to the subjects a pharmaceutical composition, wherein the pharmaceutical composition comprises a plurality of isolated stem cells in a pharmaceutically acceptable carrier, in an amount and via a route sufficient to allow at least a fraction of the population of stem cells to engraft a tissue and differentiate therein, whereby an injury in the subject including but not limited to injuries arising from expose to radiation is treated.

As used herein, the phrase "treating an injury to a tissue or organ in a subject" refers to both intervention designed to ameliorate the symptoms of causes of the injury in a subject (e.g., after initiation of a disease process) as well as to interventions that are designed to prevent the injury from occurring in the subject. Stated another way, the terms "treating" and grammatical variants thereof are intended to be interpreted broadly to encompass meanings that refer to reducing the severity of and/or to curing a disease or disorder, as well as meanings that refer to prophylaxis. In this latter respect, "treating" to refers to "preventing" or otherwise enhancing the ability of the subject to resist the effects of a disease process or injury such as, but not limited to an injury secondary to radiation exposure.

Given that the stem cell populations of the presently disclosed subject matter also can give rise to various cells of the hematopoietic lineage, in some embodiments the injury or the disease is an injury or a disease that results from abnormal hematopoiesis and/or from destruction of one or more cells of the hematopoietic lineage. An exemplary non-limiting hematopoietic disease is aplastic anemia, although any other hematopoietic disease is also within the scope of the presently disclosed compositions and methods.

III.B. Formulations

The compositions of the presently disclosed subject matter comprise in some embodiments a composition that includes a carrier, particularly a pharmaceutically acceptable carrier, such as but not limited to a carrier pharmaceutically acceptable in humans. Any suitable pharmaceutical formulation can be used to prepare the compositions for administration to a subject.

For example, suitable formulations can include aqueous and non-aqueous sterile injection solutions that can contain anti-oxidants, buffers, bacteriostatics, bactericidal antibiotics, and solutes that render the formulation isotonic with the bodily fluids of the intended recipient.

It should be understood that in addition to the ingredients particularly mentioned above the formulations of the presently disclosed subject matter can include other agents conventional in the art with regard to the type of formulation in question. For example, sterile pyrogen-free aqueous and non-aqueous solutions can be used.

The therapeutic regimens and compositions of the presently disclosed subject matter can be used with additional adjuvants or biological response modifiers including, but not limited to, cytokines and other immunomodulating compounds.

III.C. Administration

Suitable methods for administration the compositions comprising the stem cells of the presently disclosed subject matter include, but are not limited to intravenous administration and delivery directly to the target tissue or organ. In some embodiments, the method of administration encompasses features for regionalized delivery or accumulation of the cells at the site in need of treatment. In some embodiments, the cells are delivered directly into the tissue or organ to be treated. In some embodiments, selective delivery of the presently disclosed cells is accomplished by intravenous injection of cells, where they home to the target tissue or organ and engraft therein. In some embodiments, the presently disclosed cells home to the target tissue or organ as a result of the production of an SDF-1 gradient produced by the target tissue or organ, which acts as a chemotactic attractant to some embodiments of the stem cells disclosed herein.

III.D. Dose

An effective dose of a composition of the presently disclosed subject matter is administered to a subject in need thereof. A "treatment effective amount" or a "therapeutic amount" is an amount of a therapeutic composition sufficient to produce a measurable response (e.g., a biologically or clinically relevant response in a subject being treated). In some embodiments, an activity that inhibits amyloid aggregate formation is measured. Actual dosage levels of active ingredients in the compositions of the presently disclosed subject matter can be varied so as to administer an amount of the active compound(s) that is effective to achieve the desired therapeutic response for a particular subject. The selected dosage level will depend upon the activity of the therapeutic composition, the route of administration, combination with other drugs or treatments, the severity of the condition being treated, and the condition and prior medical history of the subject being treated. However, it is within the skill of the art to start doses of the compound at levels lower than required to achieve the desired therapeutic effect and to gradually increase the dosage until the desired effect is achieved. The potency of a composition can vary, and therefore a "Treatment effective amount" can vary. However, using the assay methods described herein, one skilled in the art can readily assess the potency and efficacy of a candidate compound of the presently disclosed subject matter and adjust the therapeutic regimen accordingly. After review of the disclosure of the presently disclosed subject matter presented herein, one of ordinary skill in the art can tailor the dosages to an individual subject, taking into account the particular formulation, method of administration to be used with the composition, and particular disease treated. Further calculations of dose can consider subject height and weight, severity and stage of symptoms, and the presence of additional deleterious physical conditions. Such adjustments or variations, as well as evaluation of when and how to make such adjustments or variations, are well known to those of ordinary skill in the art of medicine.

As such, in some embodiments the presently disclosed populations of stem cells are present in a pharmaceutically acceptable carrier, which in some embodiments can be a pharmaceutically acceptable for use in humans.

IV. Methods for Expanding and Stimulating Proliferation of Stem Cell Subpopulations The presently disclosed subject matter also provides in some embodiments methods for expanding stem cells. In some embodiments, the methods comprise providing a purified population of $CD45^-$ or $CD45^+$ stem cells, optionally a purified population of $CD45^-$ or $CD45^+$ stem cells isolated by a method as disclosed herein, and growing the purified population of $CD45^-$ or $CD45^+$ stem cells in culture in the presence of one or more pituitary or gonadal sex hormones (such as, but not limited to a pituitary or gonadal sex hormone that binds to a receptor selected from the group consisting of FSHR, LHCGR, PRLR, AR, ESRα, ESRβ, and PGR) and a suboptimal dose of hematopoietic cytokines and growth factors, wherein the growing is under conditions and for a time sufficient to expand the CD45$^-$ or CD45$^+$ stem cells. In some embodiments, the pituitary or gonadal sex hormone that binds to a receptor selected from the group consisting of FSH, LH, PRL, an androgen, an estrogen, and PG.

As used herein, the phrase "suboptimal dose of hematopoietic cytokines and growth factors" refers to a dose of hematopoietic cytokines and/or growth factors that is in some embodiments 5%, in some embodiments 10%, in some embodiments 15%, in some embodiments 20%, and in some embodiments greater than 20% but less than 100%, 95%, 90%, 85%, 80%, 75%, 70%, 65%, 60%, 55%, or 50% of that known to one of ordinary skill in the art to support expansion and/or proliferation (e.g., clonogenic growth) of burst-forming unit-erythroid (BFU-E) colonies, CFU-granulocyte/macrophage (CFU-GM) colonies, CFU-megakaryocytes (CFU-meg) colonies, and/or CFU-Mix colonies. In some embodiments, a "suboptimal dose of hematopoietic cytokines and growth factors" can include one-tenth of optimal doses of hematopoietic cytokines and growth factors typically used in clonogenic assays for these cell types.

By way of example and not limitation, clonogenic growth CFU-GM colonies can be stimulated by growing cells in a medium that contains 1 ng/mL recombinant human interleukin-3 (rhIL-3) and 0.5 ng/mL recombinant human granulocyte/macrophage colony-stimulating factor (rhGM-CSF); clonogenic growth of BFU-E colonies can be stimulated with 0.2 IU/mL of recombinant human erythropoietin (rhEPO) and 1 ng/mL of recombinant human stem cell factor (rhSCF); clonogenic growth of CFU-meg can be stimulated by growing cells in a medium that contains 5 ng/mL of recombinant human thrombopoietin (rhTPO) and 1 ng/mL of rhIL-3 and clonogenic growth of CFU-Mix colonies can be stimulated by 1 ng/mL of rhIL-3, 0.5 ng/mL of G-CSF, 1 ng/mL of SCF, 0.2 IU/mL of EPO, and 5 ng/mL of TPO.

The medium in which the stem cell populations of the presently disclosed subject matter are grown for expansion, proliferation, or clonogenic growth includes a suboptimal dose of hematopoietic cytokines and growth factors and also includes one or more pituitary or gonadal sex hormones, which in some embodiments are selected from the group consisting of FSHR, LHCGR, PRLR, AR, ESRα, ESRβ, and PGR.

In some embodiments of the presently disclosed methods, the purified population of CD45$^-$ or CD45$^+$ stem cells is a population of CD45$^+$ cells enriched for hematopoietic stem/progenitor cells (HSPCs), a population of CD45$^+$ mesenchymal stromal cells (MSCs), or is any combination thereof, and/or is a population of CD45 very small embryonic-like stem cells (VSELs). In some embodiments, the HSPCs, MSCs, and/or the VSELs are human HSPCs, MSCs, and/or VSELs.

In some embodiments, the presently disclosed subject matter also provides methods for stimulating proliferation of mesenchymal stromal cells (MSCs). In some embodiments, the methods comprise growing a population of MSCs in culture in the presence of one or more pituitary or gonadal sex hormones and suboptimal doses of hematopoietic cytokines and growth factors under conditions and for a time sufficient to stimulate proliferation of the MSCs. Here as well, the suboptimal dose of hematopoietic cytokines and growth factors can be a dose of hematopoietic cytokines and/or growth factors that is in some embodiments 5%, in some embodiments 10%, in some embodiments 15%, in some embodiments 20%, and in some embodiments greater than 20% but less than 100%, 95%, 90%, 85%, 780%, 75%, 70%, 65%, 60%, 55%, or 50% of that known to one of ordinary skill in the art to support expansion and/or proliferation (e.g., clonogenic growth) of burst-forming unit-erythroid (BFU-E) colonies, CFU-granulocyte/macrophage (CFU-GM) colonies, CFU-megakaryocytes (CFU-meg) colonies, and/or CFU-Mix colonies, which in some embodiments can include one-tenth of optimal doses of hematopoietic cytokines and growth factors typically used in clonogenic assays for these cell types. The MSCs are thus grown in a medium that contains the appropriate hematopoietic cytokines and growth factors as well as one or more pituitary or gonadal sex hormones selected from the group consisting of FSH, LH, PRL, androgen, estrogen, and PG.

V. Methods for Treating Hematopoietic Injuries and Radiation Sickness

The presently disclosed subject matter also provides in some embodiments methods for treating subjects suffering from hematological diseases or other disorder resulting primarily or secondarily to a deficit in normal hematopoiesis. Exemplary non-limiting such hematological diseases or disorders include, but are not limited to, aplastic anemia and any hematopoietic disease resulting from exposure to radiation. In some embodiments, the methods comprise administering to a subject in need thereof an amount of a population of the presently disclosed stem cells sufficient to ameliorate at least symptom or consequence of the disease or disorder.

Alternatively or in addition, a method for treating a subject suffering from a hematological disease or other disorder resulting primarily or secondarily from a deficit in normal hematopoiesis such as but not limited to radiation exposure can comprise administering to the subject an effective amount of FSH and/or LH, wherein the effective amount is sufficient to ameliorate at least symptom or consequence of the hematological disease or other disorder.

VI. Methods for In Vitro Gametogenesis

The presently disclosed subject matter also provides methods for producing gametes in vitro. Generalized methods for generating gametes from stem cells are described in West et al, 2013 and references cited therein.

Thus, in some embodiments the methods of the presently disclosed subject matter comprise providing a population of VSELs isolated from bone marrow; and contacting the VSELs in vitro with an amount of FSH and/or LH sufficient to induce differentiation of the VSELs and/or their progeny cells to gametes. In some embodiments, the exposure of the VSELs to FSH and/or LH is under conditions sufficient to modify somatic imprinting in the VSELs such as, but not limited to remethylation of erased differently methylated regulatory regions in paternally imprinted genes (see e.g., U.S. Patent Application Publication No. 2013/0323197 for a discussion of imprinting in VSELs).

An exemplary application of in vitro gametogenesis using VSELs as set forth herein could be to provide a source of gametes for patients that have suboptimal gametogenesis, for example subsequent to a disease, disorder, or condition, and/or a treatment for a disease, disorder, or condition. By way of example and not limitation, it is known that various anti-cancer treatments can irreversibly damage gametogenesis. VSELs, however, are relatively resistant to the toxic effects of radiotherapy and chemotherapy, and thus a subject's own VSELs could be employed using the methods set forth herein to provide in vitro-generated gametes that have the subject's own genome. Thus, in some embodiments the presently disclosed subject matter provides a method for treating infertility in a subject by generating gametes in vitro from VSELs isolated before, during, and/or after a treatment that is suspected of negatively impacting gametogenesis in situ in the subject.

Additionally, the presence of functional sex hormone receptors on bone marrow- or umbilical cord blood-isolated VSELs, as well expression of several markers for migrating primordial germ cells in this cell population, suggests that VSELs isolated from hematopoietic organs and tissues correspond to VSELs present in adult gonads (see e.g., Stimpfel et al., 2013; Bhartiya et al, 2014; Anand et al., 2015; Sriraman et al, 2015).

EXAMPLES

The presently disclosed subject matter will be now be described more fully hereinafter with reference to the accompanying EXAMPLES, in which representative embodiments of the presently disclosed subject matter are shown. The presently disclosed subject matter can, however, be embodied in different forms and should not be construed as limited to the embodiments set forth herein. Rather, these embodiments are provided so that this disclosure will be thorough and complete, and will fully convey the scope of the presently disclosed subject matter to those skilled in the art.

Materials and Methods Employed in Examples 1-3

Isolation of Human CD34$^+$ Population from Peripheral Blood

Low-density mobilized and immobilized peripheral blood mononuclear cells (mPB-MNCs and PB-MNCs, respectively) were harvested from consenting healthy donors. From these MNCs, cell populations enriched in CD34 markers were collected as described in Majka et al, 2000.

Isolation of CD34$^+$ Cells from Umbilical Cord Blood (UCB)

In some experiments, CD34$^+$ cells from human UCB were also separated by immune-mediated positive selection using anti-CD34$^+$ magnetic paramagnetic beads (Miltenyi Biotec Inc., San Diego, Calif., United States of America), according to the manufacturer's protocol. The purity of isolated CD34$^+$ cells was >95%, as determined by fluorescence-activated cell sorter (FACS; Beckman Coulter, Inc., Brea, Calif., United States of America) analysis.

Isolation of Human UCB-Derived HSPCs and VSELs

Clinical-grade umbilical cord blood (UCB) research units shipped from Cleveland Cord Blood Center (Cleveland, Ohio, United States of America) were employed for isolation of umbilical cord blood hematopoietic stem/progenitor cells (UCB-HSPCs) and umbilical cord blood very small embryonic like stem cells (UCB-VSELs). In brief, total nucleated cells (TNCs) were retrieved after lysing red blood cells (RBCs) twice, for 10 minutes each time, at room temperature using hypotonic lysing buffer (PHARMLYSE™, BD Bioscience, Pharmingen, San Diego, Calif., United States of America). Next, the TNCs were washed twice in RPMI-1640 medium (GE Healthcare Life Science, Logan, Utah, United States of America) supplemented with 2% inactivated fetal bovine serum (FBS; Seradigm, Radnor, Pa., United States of America). Using a cocktail of biotin-conjugated monoclonal antibodies and anti-biotin monoclonal antibodies conjugated to paramagnetic microbeads (Lineage Cell Depletion kit, Miltenyi Biotec Inc., San Diego, Calif., United States of America), magnetic labeling of TNCs was performed, and the lineage-negative (Lin$^-$) cells were isolated by depletion of mature hematopoietic cells expressing a panel of lineage antigens using an AUTOMACS® separator (Miltenyi Biotec GmbH, Bergisch Gladbach, Germany). Afterwards, lineage-negative populations were stained with the following antibodies: anti-CD45 (PE or V450, clone HI30; ThermoFischer Scientific Inc., Waltham, Mass., United States of America) and anti-CD34 (APC or PE, clone 581; STEMCELL™ Technologies Inc., Vancouver, British Columbia, Canada). After washing, the fluorochrome-labelled cells were resuspended and sorted using a multiparameter live-cell sorter (BD Bioscience, San Diego, Calif., United States of America) to obtain populations enriched in hematopoietic stem/progenitor cells (HSPCs, Lin$^-$/CD45$^+$/CD34$^+$) and VSELs (Lin$^-$/CD45$^-$/CD34$^+$).

Isolation and Cultivation of Human Mesenchymal Stromal Cells

Mesenchymal stromal cells from UCB (hUCB-MSCs) were obtained from the CD34$^-$ cell fraction after paramagnetic separation. Directly after the separation process, the cells were centrifuged, washed with PBS, and then cultivated in Dulbecco's modified Eagle's medium (DMEM; Mediatech, Inc. Manassas, Va., United States of America), supplemented with 20% FBS, 100 IU/mL penicillin, and 10 µg/mL streptomycin (Lonza America Inc., Allendale, N.J., United States of America) in a 5% $CO_2$ incubator at 37° C. After seven days of primary cultivation, fibroblast-like cells were obtained. The medium was immediately exchanged and then every three days thereafter. At approximately 80% confluence, the cells were passaged using 0.25% trypsin (Mediatech, Inc. Manassas, Va., United States of America).

Culture of Primary Human Umbilical Vein Endothelial Cells

Primary human umbilical vein endothelial cells (HUVECs) were purchased from American Type Culture Collection (ATCC; Manassas, Va., United States of America). HUVECs were cultured and grown in vascular cell basal medium (ATCC; PCS-100-030) supplemented with bovine brain extract (BBE; 0.2%), recombinant human (rh) EGF (5 ng/mL), L-glutamine (10 mM), heparin sulfate (0.75 IU/mL), hydrocortisone hemisuccinate (1 µg/mL), 2% FBS, and ascorbic acid (50 µg/mL). All supplements were purchased from to ATCC (#PCS-100-040). These cells were cultured at 37° C. in a $CO_2$ humidified atmosphere and detached from the growth plates using non-enzymatic cell dissociation solution (CELLSTRIPER®; Mediatech, Inc. Manassas, Va., United States of America).

Clonogenic Assays In Vitro

Isolated hUCB CD34$^+$ cells obtained from healthy donors were subjected to colony assays in response to different sex hormones (SexHs). In brief sorted CD34$^+$ cells (4×10$^5$ cells/mL) were resuspended in RPMI 1640 medium supplemented with 2% FBS (final concentration), and then mixed with methylcellulose base cultures (METHOCULT™ HCC-4230; Stem Cell Technologies Inc., Vancouver, British Columbia, Canada) supplemented with L-glutamine (Lonza America Inc., Allendale, N.J., United States of America) and antibiotics. In the colonogenic in vitro assays, one-tenth of optimal doses of hematopoietic cytokines and growth factors were employed. Growth of colony-forming unit-granulocyte/macrophage (CFU-GM) colonies was stimulated with recombinant human interleukin-3 (rhIL-3; 1 ng/mL) and recombinant human granulocyte/macrophage colony-stimulating factor (rhGM-CSF; 0.5 ng/mL). Growth of burst-forming unit-erythroid (BFU-E) colonies was stimulated with recombinant human erythropoietin (rhEPO; 0.2 IU/mL) and recombinant human stem cell factor (rhSCF; 1 ng/mL). To examine CFU-megakaryocytes (CFU-meg), recombinant human thrombopoietin (rhTPO, 5 ng/mL) and rhIL-3 (1 ng/mL) were added to the base medium. To growth CFU-Mix colonies cells were stimulated by IL-3 (1 ng/mL), G-CSF (0.5 ng/mL), SCF (1 ng/mL), FPO (0.2 IU/mL) and TPO (5 ng/mL). All cytokines and growth factors were purchased from R&D Systems (Minneapolis, Minn., United States of America). Cells in clonogenic assays were co-stimulated with SexHs (FSH at 5 IU/mL; LH at 5 IU/mL; prolactin at 1 μg/mL; estradiol at 0.1 μM; progesterone at 0.1 μM; or androgen (danazol) at 4 mg/mL). The pituitary hormones were purchased from ProSpec (East Brunswick, N.J., United States of America), while the gonadal hormones were purchased from Sigma-Aldrich (St. Louis, Mo., United States of America). The cells maintained without any hormonal treatment were served as a control. Cultures were then incubated at 37° C. in a fully humidified atmosphere supplemented with 5% $CO_2$. Two weeks later, the colonies formed were scored under an inverted microscope.

Preparation of Conditioned Media

UCB-MSCs were used to obtain conditioned media (CM). UCB-MSCs in passage 3 were seeded into 6-well plates at a density of 10,000 cells per well. The cells were nourished with 20% FBS DMEM until they reached approximately 85% confluence. At this time, the cells were washed twice with PBS, and then 0.5% bovine serum albumin (BSA; Sigma-Aldrich, St. Louis, Mo., United States of America) in DMEM was added to the cells, either alone (control) or with FSH (10 IU/mL), LH (10 IU/mL), or prolactin (2 μg/mL). At the same time, only media with sex hormones were also incubated. After 24 hours, all CM were separately harvested, centrifuged, filtered, and then stored at −80° C. until use.

Transwell Migration Assay

The Transwell migration assay was performed as follows. UCB-derived HSPCs were rendered quiescent by incubation in RPMI medium supplemented with 0.5% BSA for 5 hours at 37° C. and then seeded at a density of $10 \times 10^4$ cells/100 μL per insert into the upper chambers of Transwell polycarbonate membrane inserts with 8-μm pore size (COSTAR™ TRANSWELL™; Corning Costar, Corning, N.Y., United States of America). The lower modified Boyden's chambers contained different concentrations of FSH (2-20 IU/mL), LH (2-20 IU/mL), prolactin (0.5-5 μg/mL), estradiol (0.1-1 μM), or progesterone (0.1-1 μM). FBS (10%) and BSA (0.5%) in RPMI 1640 medium were used as positive and negative controls, respectively. After 3 hours of stimulation at 37° C., the migrated cells were collected from the lower chambers and then scored using fluorescence-activated cell sorting (FACS) analysis. For UCB-MSC chemotaxis, cells were detached with 0.25% trypsin, starved for 24 hours, and then seeded into the upper gelatin-coated (0.5%) inserts at a density of $7 \times 10^4$ cells/insert in 100 μL. Pre-warmed culture medium containing SexHs, (FSH at 10 IU/mL; LH at 10 IU/mL; prolactin at 2 μg/mL; or estradiol at 0.1 μM) was added to the lower chambers. After 48 hours, the inserts were collected from the Transwell supports. The cells that had migrated to the lower side of the membrane were fixed and stained with the FISHER HEALTHCARE™ PROTOCOL™ HEMA 3™ brand staining protocol (Fisher Scientific, Pittsburgh, Pa., United States of America) according to the manufacturer's instructions and then counted using an inverted microscope.

Adhesion of Hematopoietic Cells and MSCs to Fibronectin

UCB-derived HSPCs and MSCs were made quiescent for 5 hours and 8 hours, respectively, with 0.5% BSA in a humidified atmosphere of 5% $CO_2$ at 37° C. Next, cells were stimulated with FSH (10 IU/mL), LH (10 IU/mL), prolactin (2 μg/mL), estradiol (0.1 μM), or 0.5% BSA in RPMI 1640 medium for 5 minutes at 37° C. Cells were added directly onto the protein-coated wells ($3 \times 10^3$ cells/well) in 96-well plates for 5 minutes. The wells were coated with fibronectin (10 μg/mL; Sigma-Aldrich, St. Louis, Mo., United States of America) overnight at 4° C. and blocked with BSA for 2 hours before starting the experiment. Following stimulation, the plates were vigorously washed 3 times, and adherent cells were counted under an inverted microscope.

Signal Transduction Studies

Western blots were performed on extracts prepared from quiescent CD34+ HSPCs and MSCs ($2 \times 10^6$ cells). The cells were stimulated with either SexHs or BSA, as indicated, for 5 minutes at 37° C. and then lysed (for 20 minutes) on ice in RIPA lysis buffer containing protease and phosphatase inhibitors (Santa Cruz Biotechnology, Inc., Santa Cruz, Calif., United States of America). Next, the extracted proteins were separated on a 4-12% sodium dodecyl sulfate-polyacrylamide gel electrophoresis (SDS-PAGE) gel, and the fractionated proteins were then transferred to a PVDF membrane. Phosphorylation of the intracellular kinases p44/42 mitogen-activated protein kinase (phospho-p44/42 MAPK) and AKT were detected using anti-phospho-p44/42 MAPK (Thr202/Tyr204; clone no. 9101) and anti-phospho-AKT (Ser473; clone no. 9271) rabbit polyclonal antibodies, both from Cell Signaling Technology, Inc. (Danvers, Mass., United States of America) followed by horseradish peroxidase (HRP)-conjugated goat anti-rabbit IgG as a secondary antibody (Santa Cruz Biotechnology, Inc., Santa Cruz, Calif., United States of America). To ensure equal protein loading in all lanes, blots were subjected to stripping and reprobing with appropriate anti-p42/44 MAPK (clone no. 9102; Cell Signaling Technology, Inc., Danvers, Mass., United States of America) and anti-AKT monoclonal antibodies (clone no. 9272; Cell Signaling Technology, Inc., Danvers, Mass., United States of America). All membranes were treated with an enhanced chemiluminescence (ECL) reagent (Amersham Life Sciences, a division of GE Healthcare Life Sciences, Pittsburgh, Pa., United States of America), dried, and subsequently exposed to film (Hyperfilm; Amersham Life Sciences). Quantification of the densities of obtained blots was performed using ImageJ software (Abramoff et al., 2004).

RNA Isolation and Reverse Transcriptase-Polymerase Chain Reaction (RT-PCR)

Total RNA was extracted and purified from hUCB-derived CD34$^+$/Lin$^-$/CD45$^+$ HSPCs and MSCs using the RNEASY® Mini Kit (Qiagen Inc., Germantown, Md., United States of America) after treatment with DNase I (Qiagen Inc., Germantown, Md., United States of America). In the case of VSELs, the total RNA was extracted using Trizol® brand RNA Isolation Reagent (ThermoFischer Scientific Inc., Waltham, Mass., United States of America) as described in (Kucia et al., 2006). The mRNA (200 ng) was next reverse-transcribed into cDNA using TAQMAN® Reverse Transcription reagents (ThermoFischer Scientific Inc., Waltham, Mass., United States of America), according to the manufacturer's instructions. Amplification of synthesized cDNA fragments was carried out using AMPLITAQ GOLD® polymerase (ThermoFischer Scientific Inc., Waltham, Mass., United States of America) for 1 cycle of 8 minutes at 95° C., 2 cycles of 2 minutes at 95° C., 1 minute at 60° C., 1 minute at 72° C., and then for 40 cycles of 30 seconds at 95° C., 1 minute at 60° C., 1 minute at 72° C., and 1 cycle of 10 minutes at 72° C. The human sequence-specific primers are provided in SEQ ID NOs: 1-14. All primers were designed using the NCBI/Primer-Blast program (available through the web site of the United States National Institutes of Science), as at least one primer included an exon-intron boundary. At the end of the PCR reaction, the PCR products were analyzed by 2% agarose gel electrophoresis.

Real-Time Quantitative PCR (RQ-PCR)

To evaluate the role of FSH in the regulation of genes expressed actively in angiogenesis, MSCs were kept in culture, either unstimulated or stimulated with FSH, for 12 to 24 hours. At various time points, the cells were collected, and total RNA was extracted and purified using the RNeasy Mini kit (Qiagen Inc., Germantown, Md., United States of America) after treatment with DNase I (Qiagen Inc., Germantown, Md., United States of America). The mRNA was then reverse-transcribed into cDNA using TAQMAN® Reverse Transcription Reagents (ThermoFischer Scientific Inc., Waltham, Mass., United States of America), according to the manufacturer's instructions. Quantitative assessment of mRNA levels of target genes was performed by RQ-PCR using an APPLIED BIOSYSTEMS® PRISM® Fast 7500 sequence detection system (ThermoFischer Scientific Inc., Waltham, Mass., United States of America). The cDNA templates were amplified using SYBR® Green PCR master mix (ThermoFischer Scientific Inc., Waltham, Mass., United States of America), and specific primers (hVEGF2 R: forward, 5'-ggtctcgattggatggcagtag-3' (SEQ ID NO: 15), reverse, 5'-cacccatggcagaaggagga-3' (SEQ ID NO: 16); β2 microglobulin R: forward, 5'-aatgcggcatcttcaaacct-3' (SEQ ID NO: 17), reverse, 5' tgactttgtcacagcccaagata-3' (SEQ ID NO: 18)). These primers sequences were designed with PRIMER EXPRESS® software (ThermoFischer Scientific Inc., Waltham, Mass., United States of America). The threshold cycle (Ct), the cycle number at which the fluorescence of the amplified gene reached a fixed threshold, was subsequently determined, and the relative quantification of the expression level of target genes was performed with the 2-ΔΔCt method.

Immunostaining of the Isolated Cells

Human UCB-derived Lin$^-$/CD133$^+$/CD45$^-$ cells (VSELs), and corresponding Lin$^-$/CD133$^+$/CD45$^+$ cells (enriched for HSPCs), and MSCs were plated, fixed in 3.7% paraformaldehyde for 15 minutes at 4° C., and then permeabilized with 0.1% TRITON™ X-100 for 5 minutes. After blocking with 2.5% BSA, the cells were subjected to immunostaining with the following primary antibodies: follicle stimulating hormone receptor (FSHR, 1:200, rabbit polyclonal antibody; Santa Cruz Biotechnology, Inc., Santa Cruz, Calif., United States of America), luteinizing hormone/choriogonadotropin receptor (LHR, 1:200, rabbit polyclonal antibody; Santa Cruz Biotechnology, Inc., Santa Cruz, Calif., United States of America), androgen receptor (1:50, rabbit polyclonal antibody; NeoMarkers, Fremont, Calif., United States of America), and estrogen receptor alpha (1:500, mouse monoclonal IgG antibody; ThermoFischer Scientific Inc., Waltham, Mass., United States of America). These antibodies were diluted in 2.5% BSA and incubated with the cells for 75 minutes at 37° C. Appropriate ALEXA FLUOR® 594 Goat Anti-Rabbit IgG and ALEXA FLUOR® 488 Goat Anti-Mouse IgG were used as secondary antibodies (1:400; all from Invitrogen™, a division of ThermoFischer Scientific Inc., Waltham, Mass., United States of America), and incubated with the cells for staining for 75 minutes at 37° C. In control experiments, cells were stained with secondary antibodies only. In all experiments, the nuclei were labeled with DAPI, and the fluorescence images were collected with a FV100 confocal laser-scanning microscope (Olympus Scientific Solutions Americas Corp. Waltham, Mass., United States of America).

In Vitro CFU-Fibroblasts Assay

In order to evaluate the effect of SexHs on fibroblast colony formation, hUCB-MSCs were collected after trypsinization and then seeded onto 6-well plates at a low cell density (30,000 cells per well) in 20% FBS DMEM and incubated at 37° C. in a humidified atmosphere of 5% $CO_2$. After 2 hours, the cells were stimulated with SexHs at the dosages indicated. Fresh medium containing SexHs was added to the cells every 24 hours for 10 days, after which the medium was removed and the cells subjected to the FISHER HEALTHCARE™ PROTOCOL™ HEMA 3™ brand staining protocol, and the fibroblast colony formation in all cell groups was then evaluated and counted.

In Vitro Angiogenesis Assay

The tube-formation assay was performed on a synthetic BD MATRIGEL® brand basement membrane complex with reduced growth factors (BD MATRIGEL®; BD Bioscience, San Diego, Calif., United States of America). In brief, the BD MATRIGEL® brand basement membrane complex was thawed overnight at 4° C. Twenty-four-well plates were coated with matrix and then polymerized for 1 hour at 37° C. Afterwards, HUVECs (60,000 cells/well) were resuspended in either serum-reduced medium containing 0.5% BSA in DMEM medium (negative control), medium containing FGF2 (50 ng/mL; positive control), CM from unstimulated hUCB-MSCs, medium supplemented with FSH (10 IU/mL), or CM collected from stimulated MSCs with the same concentration of FSH. The cells were seeded on the polymerized BD MATRIGEL® brand basement membrane complex in duplicate and kept in a humidified environment of 5% $CO_2$ at 37° C. After 2 to 4 hours, the cultures were evaluated for capillary-like tube formation, the identical fields in each well were photographed, and the formed tubes in each group were then scored.

Statistical Analysis

All data obtained are presented as mean±SD. Statistical analysis of the data was done by one-way analysis of variance (ANOVA) with post hoc Tukey's test using Graph-Pad Prism 5.0 program (GraphPad Software, Inc., La Jolla, Calif., United States of America) with $p<0.05$ and $p<0.01$ considered significant.

Example 1

Human HSPCs Express Functional Gonadal and Pituitary Sex Hormone Receptors

It has been reported that murine HSPCs express several SexH receptors (Mierzejewska et al, 2015). FIG. 1A shows that two FACS-sorted populations, human $CD34^+/Lin^-/CD45^+$ cells, which are highly enriched for HSCs, and small $CD34^+/Lin^-/CD45^-$ cells, which are highly enriched for VSELs, expressed mRNA for all pituitary and gonadal sex hormone receptors. Similar mRNA expression was obtained for human $CD34^+$ HSPCs isolated from normal and mobilized PB (see FIG. 2). Expression of SexH receptors at the protein level on human HSPCs was subsequently confirmed in human UCB-purified $CD34^+$ cells by immunostaining (FIG. 1B).

Next, whether human $CD34^+$ cells sorted from UCB responded to stimulation by SexHs by phosphorylation of MAPKp42/44 and AKT was tested. FIG. 1C shows that human $CD34^+$ cells responded to stimulation by both pituitary and gonadal SexHs, and these results are quantified in FIG. 1D.

Example 2

SexHs Stimulate In Vitro Growth of Human Clonogenic Progenitors

Figure 3A:
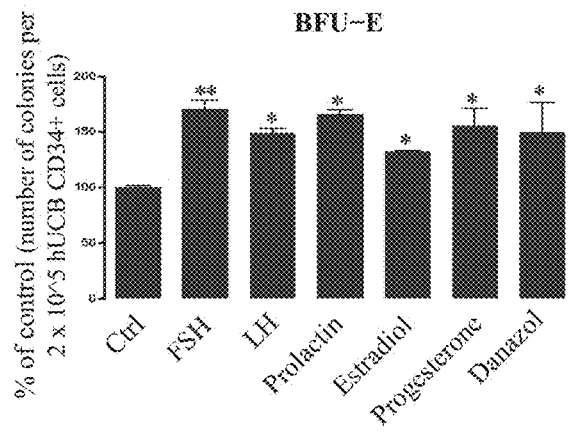
FIGS. 3A-3D are a series of bar graphs showing that the number of clonogenic CFU-GM (FIG. 3A), BFU-E (FIG. 3B), CFU-Meg (FIG. 3C), and CFU-Mix (FIG. 3D) progenitors increased in vitro after co-stimulation of human UCB CD34$^+$ progenitors with SexHs. SexHs co-stimulate in vitro proliferation of human UCB CD34$^+$ cells in methylcellulose-based cultures containing suboptimal doses (1/10 of optimal doses) of growth factors/cytokines and the indicated doses of pituitary and gonadal SexHs. The number of colonies formed in the absence of SexHs was considered to be 100%. Data are combined from four independent experiments and means±SD are shown. *p<0.05 and **p<0.01 are considered significant compared with the control group. Abbreviations: BFU-E, erythrocyte burst-forming units; CFU-GM, granulocyte/macrophage colony-forming units; CFU-Meg, megakaryocytic colony-forming units.
Figure 3B:
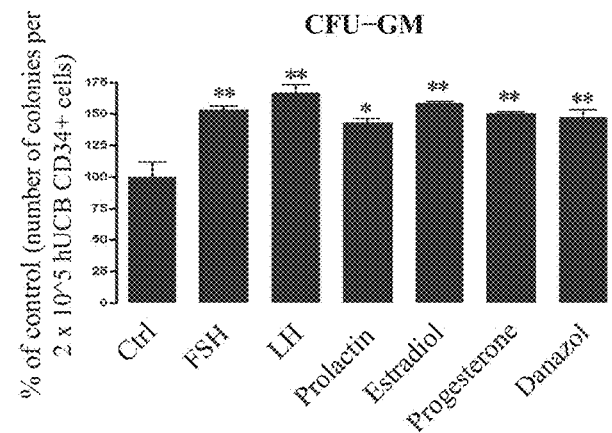
Figure 3C:
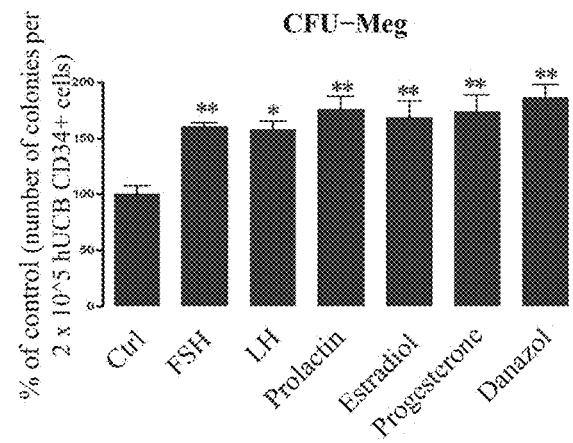
Figure 3D:
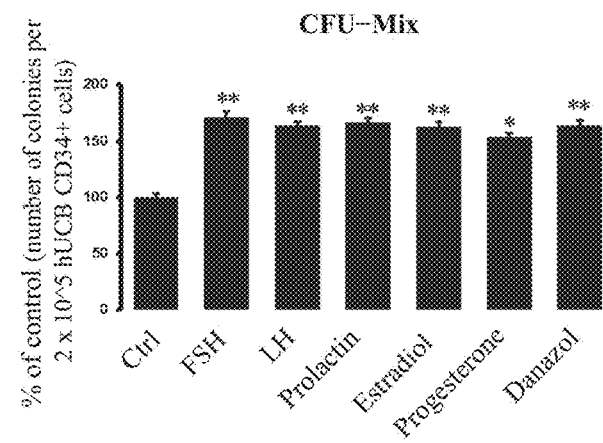

Next, whether human clonogenic progenitors responded to stimulation by SexHs as previously observed for murine cells (Mierzejewska et al, 2015) was tested. To address this question, in vitro assays were performed in which sorted $CD34^+$ cells isolated from UCB were stimulated with suboptimal doses (one-tenth of the optimal dose) of growth factors and cytokines in the presence or absence of pituitary or gonadal SexHs (see FIG. 3). It was determined that all SexHs increased clonogenic growth of human BFU-E (FIG. 3A), CFU-GM (FIG. 3B), CFU-Meg (FIG. 3C), and more primitive CFU-Mix (FIG. 3D) progenitors ($p<0.05$).

At the same time, while $CD34^+$ cells responded to SexH stimulation by phosphorylation of MAPKp42/44 and AKT (FIGS. 1C and 1D), surprisingly no effect of SexHs on migration or adhesion of clonogenic $CD34^+$ cells were observed.

Example 3

Human Mesenchymal Stromal Cells Express Several Functional SexH Receptors

Figures 4A, 4B, 4C:
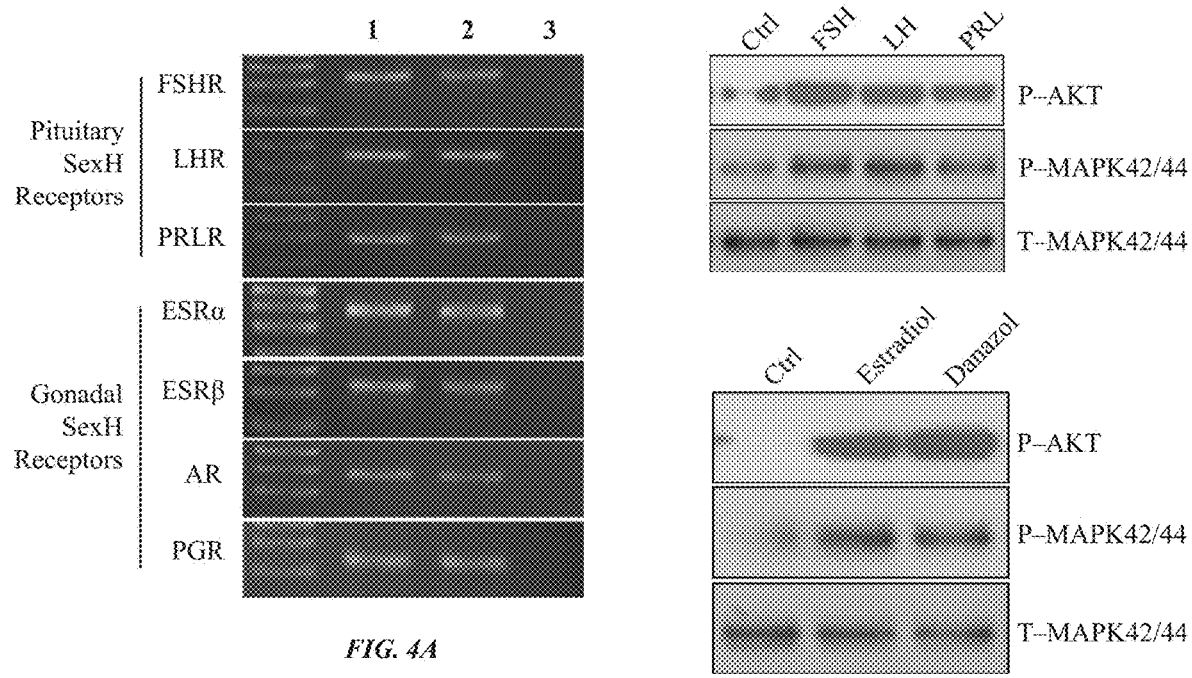
FIGS. 4A-4C show that human mesenchymal stromal cells (hMSCs) purified from umbilical blood (UCB) expressed functional SexH receptors.
Figure 5A:
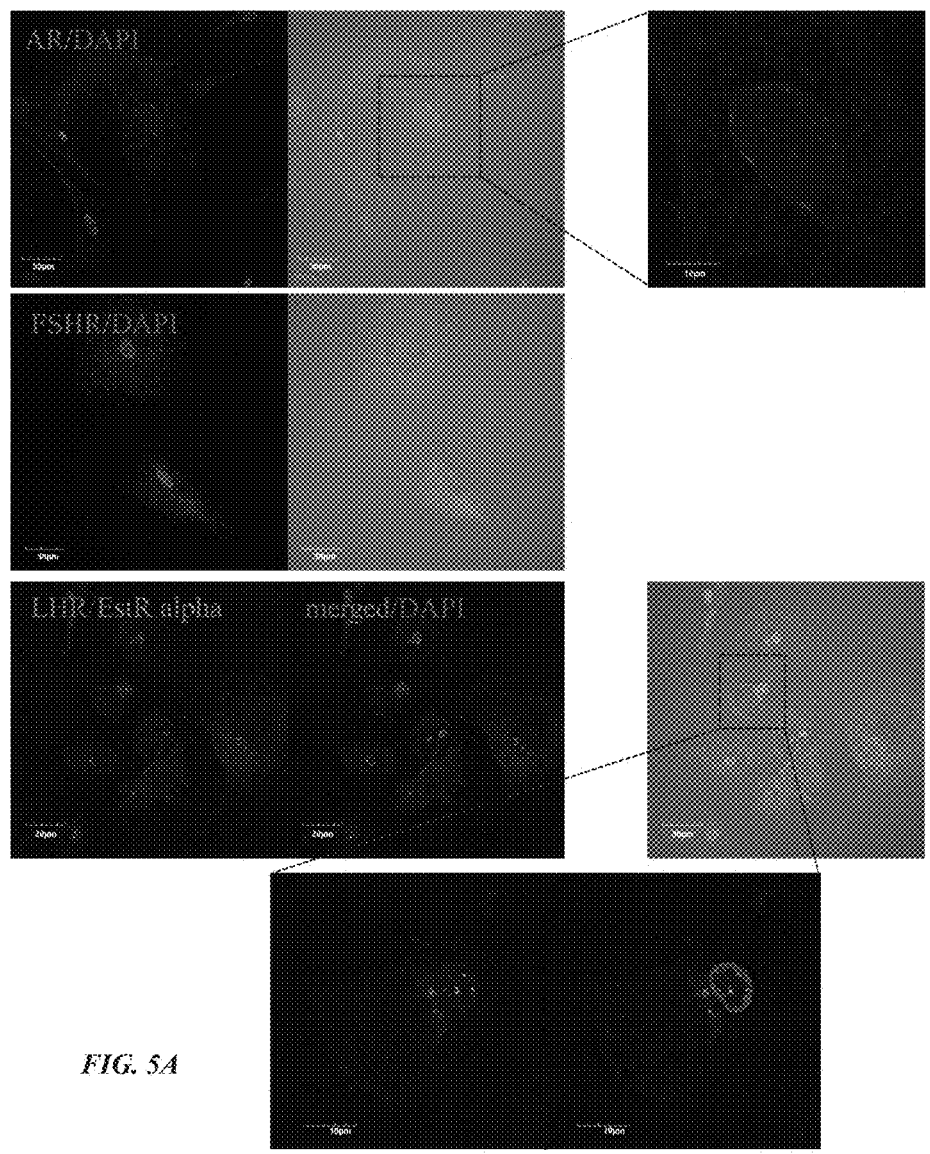
FIGS. 5A and 5B show that expression of two pituitary SexH receptors, FSHR and LHR, and two gonadal SexH receptors, AR and EstR, was detected on human MSCs by immunofluorescence staining (FIG. 5A) (n=2). An example of control staining showing that a secondary antibody conjugated with Alexa 488 or Alexa 594 did not bind to cells if the primary antibody was not employed (FIG. 5B).
Figure 5B:
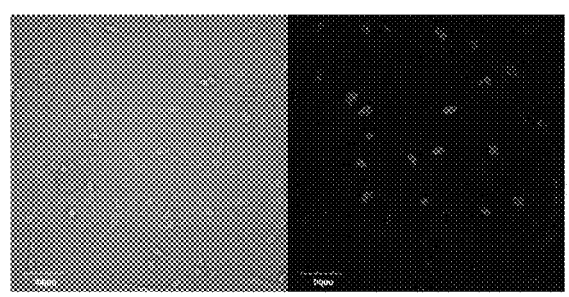

Since mesenchymal stromal cells (MSCs) play an important role in hematopoiesis, the roles of SexHs in these cells was investigated. First, the expression of SexH receptors on human umbilical cord blood-derived MSCs at the mRNA level was determined. FIG. 4A shows that all pituitary and gonadal SexH receptors evaluated as set forth herein were expressed by human MSCs, which was subsequently confirmed at the protein level (see FIGS. 5A and 5B). Moreover, signal transduction experiments revealed that these receptors were functional, as UCB-derived MSCs responded to SexH stimulation by MAPKp42/44 and AKT phosphorylation (FIGS. 4B and 4C).

Figure 6A:
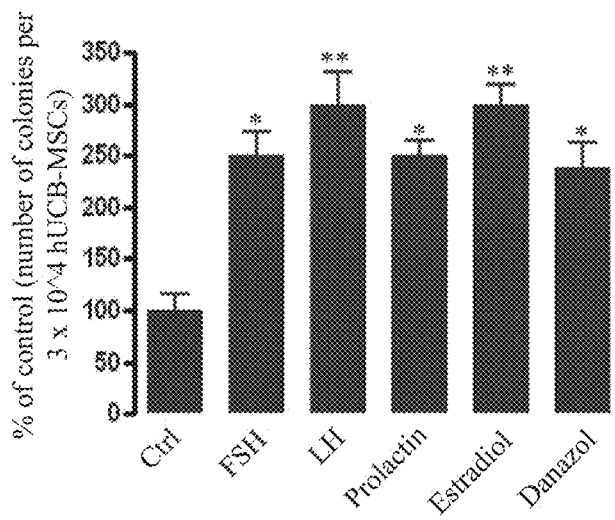
FIGS. 6A-6D show that human MSCs proliferated in vitro after stimulation with SexHs.
Figure 6B:
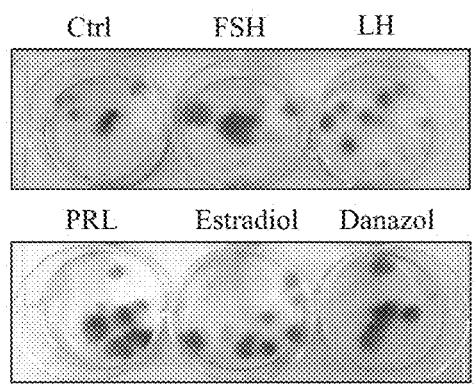

Since SexHs activated human MSC phosphorylation of MAPKp42/44 and AKT, whether they stimulated proliferation of these cells was also investigated. As demonstrated in FIGS. 6A and 6B, SexHs stimulated proliferation of MSC-derived CFU-F colonies.

Figure 6C:
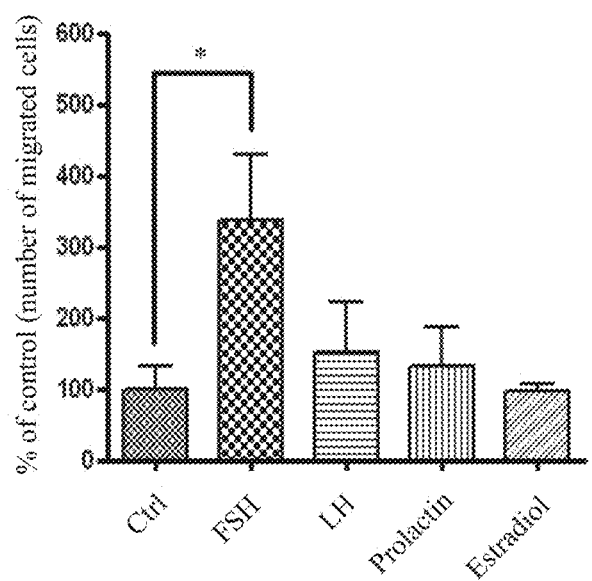
Figure 6D:
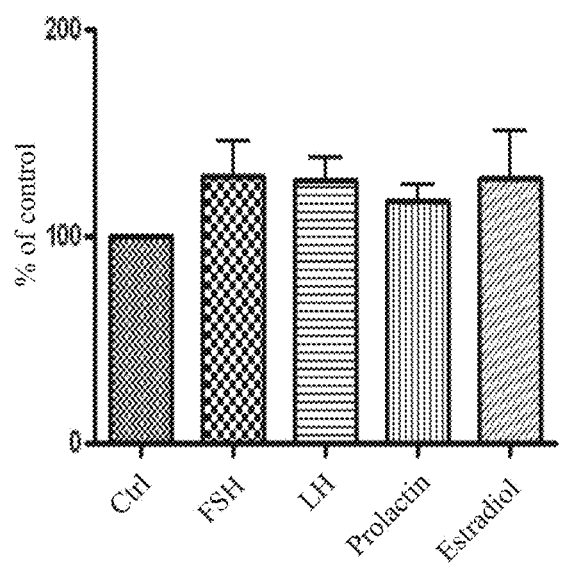

Next, Transwell chemotactic cell migration assays were performed and it was found that, of all the SexHs tested, only FSH strongly chemoattracted UCB-derived MSCs (FIG. 6C). Furthermore, FSH, like other SexHs, slightly enhanced adhesion of MSCs (FIG. 6D).

Figure 7A:
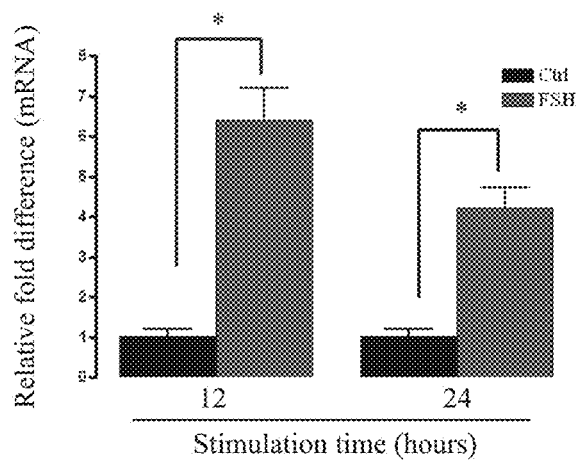
FIGS. 7A-7C show that MSCs stimulated by FSH promote angiogenesis.
Figure 7B:
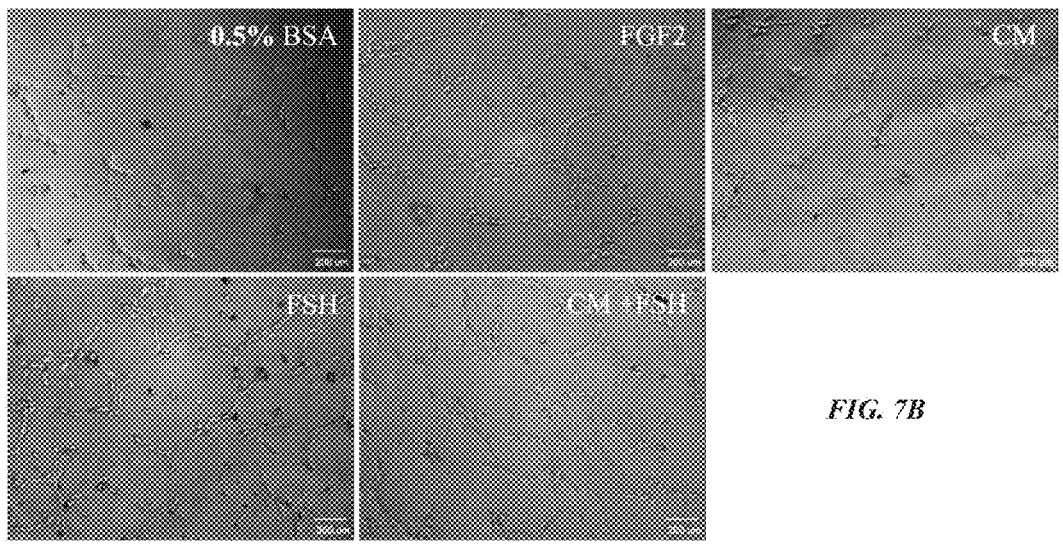
Figure 7C:
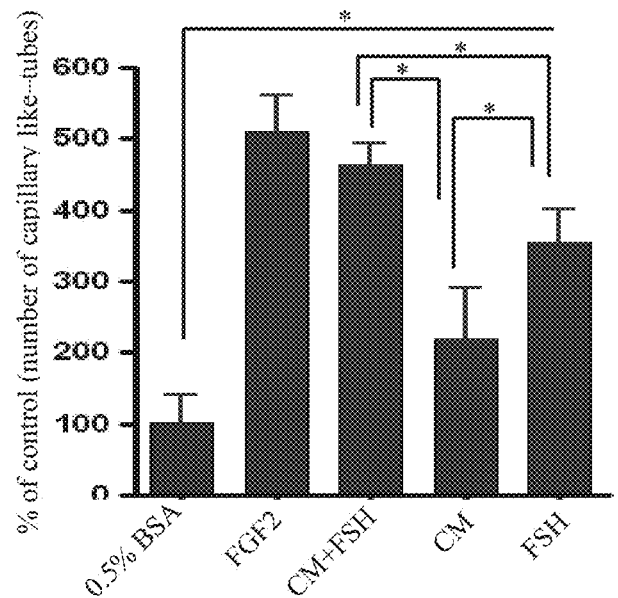

Finally, the effect of SexHs on expression of selected growth factors and chemokines involved in angiogenesis in UCB-derived MSCs was evaluated. The RQ-PCR results disclosed herein revealed that FSH strongly upregulated expression of VEGF (FIG. 7A). Therefore, to address the potential effect of FSH-stimulated MSCs on endothelium, a tube-formation assay employing HUVECs was performed. FIGS. 7B and 7C demonstrates that tube formation by HUVECs was significantly enhanced in the presence of CM isolated from cells stimulated by FSH as well as by FSH alone.

Discussion of Examples 1-3

As disclosed herein, functional pituitary and gonadal sex hormones were expressed by human HSPCs, and SexHs directly enhanced clonogenic growth of human CFU-GM, BFU-E, and CFU-Meg progenitors. Moreover, the presently disclosed subject matter demonstrated for the first time that human VSELs, like their murine counterparts (Mierzejewska et al, 2015), also expressed several SexH receptors at both the mRNA and protein levels.

These results are relevant for a few reasons. First, they suggested a developmental connection between the germline, particularly migrating primordial germ cells (PGCs), and hematopoiesis (Rich, 1995; Ohtaka et al, 1999; Kritzenberger & Wrobel, 2004; Yoshimoto et al., 2009; Shin et al., 2010; Ratajczak et al, 2014; Suszynska et al, 2014b). In support of this intriguing possibility, specification of the first primitive HSPCs in the yolk sac blood islands as well as the origin of definitive HSPCs in the aorta-gonado-mesonephros (AGM) region are chronologically and anatomically correlated with the developmental migration of PGCs in extra- and intra-embryonic tissues (Kritzenberger & Wrobel, 2004; Shin et al, 2010; Ratajczak et al., 2014; Suszynska et al., 2014b; Ratajczak, 2015). Based on these observations, it has been postulated that a subpopulation of cells derived from PGCs could contribute during the earliest stages of embryogenesis to the population of hemangioblasts in the yolk sac and, later on before entering the genital ridges, could contribute to the population of HSPCs in the hemangiopoietic endothelium of aorta (Jordan, 1917; Lux et al., 2008; Palis, 2014). Nevertheless, it has been demonstrated that murine PGCs are able to give rise to HSPCs in vitro (Rich, 1995; Ohtaka et al., 1999) and in vivo (Jordan, 1917).

Similarly, hematopoietic development was observed in murine (Miwa et al, 1991; Ohtaka et al., 1999; Yoshimoto et al, 2009) and human (Nichols et al., 1985; Chaganti et al., 1989) teratocarcinoma cell lines. Furthermore, several papers have described the sharing of chromosomal aberrations between germline tumors and leukemias or lymphomas (Nichols et al, 1985; Chaganti et al, 1989; Woodruff et al, 1995; De Miguel et al., 2009). Moreover, murine and human germline cells share with HSPCs a functional erythropoietin receptor (EpoR; see Suszynska et al., 2014a). Accordingly, human and murine germline-derived teratocarcinoma cell lines as well as ovarian cancer cell lines likely respond to erythropoietin by chemotaxis, increased adhesion, and phosphorylation of MAPKp42/44 and AKT (Suszynska et al., 2014a). Finally, the transcription factor Sall4 has been reported to play an important role in both hematopoiesis and germline development (Milanovich et al., 2015).

The data presented herein also raises another intriguing question. Since it has been demonstrated that murine (Ratajczak et al., 2011a) and human (Ratajczak et al, 2011b) VSELs become specified into HSPCs in appropriate co-culture conditions, it is possible that VSELs are precursors for the hematopoietic lineage (Zuba-Surma & Ratajczak, 2010; Ratajczak et al., 2011a; Ratajczak et al., 2011b; Grymula et al., 2014), as it has been already demonstrated by others that they are precursors of MSCs in bone marrow (Havens et al., 2013). The presence of primitive hematopoietic precursors in adult BM that do not meet the phenotypic criteria of "classical" long-term repopulating hematopoietic cells (LT-HSCs) has been proposed, and such cells have been given different operational names (Suszynska et al., 2014b). Some of them have been reported to be CD45$^-$, as have VSELs (Mierzejewska et al., 2015).

Taking into consideration that VSELs also express several genes characteristic of endothelial cells (e.g., Flk-1), a relationship between VSELs and hemangioblasts, which populate the fetal liver during embryogenesis and adult BM later (Zuba-Surma et al, 2009; Mierzejewska et al, 2015; Ratajczak, 2015), is possible. Interestingly, it has recently been reported that human VSELs isolated from peripheral blood from patients with critical limb ischemia are endowed with remarkable in vivo angiopoietic potential (Guerin et al, 2015). It is also tempting to conjecture that VSELs are the missing connection between PGCs and LT-HSCs, and, in fact, it has been reported that VSELs express several genes and markers characteristic of migrating PGCs, including murine vasa homolog (Mvh; see Shin et al, 2010).

Finally, the data presented herein support a functional link between hematopoiesis, MSCs, and angiogenesis in the responsiveness of BM cells to SexHs. First, for the first time the effect of pituitary SexHs, such as FSH and LH, on human hematopoiesis has been demonstrated. These observations complete an old study showing that hypophysiotropic hormones, such as FSH-releasing protein (known as activing and FSH-release inhibiting protein [inhibin]), regulate the in vitro development of erythroid colonies (Yu et al, 1987). In addition it is possible that FSH and LH, like other SexHs (Selleri et al, 1991), could be employed to treat aplastic anemias or to accelerate hematopoietic recovery, for example, in irradiated victims. Moreover, since FSH is upregulated in older patients as a result of age-dependent gonadal dysfunction (Wang et al., 1991; Klein et al, 1996), it might have a role in co-facilitating development of myeloid leukemia.

Also disclosed herein is that normal human MSCs expressed several functional SexH receptors and responded by proliferation to SexH simulation. The observed pro-angiopoietic effect of conditioned media from FSH-stimulated MSCs and upregulation of VEGF in these cells sheds additional light on SexH-mediated interactions between MSCs and endothelium. FSH has already been reported to stimulate murine endothelial cells (Stilley et al, 2014), and the results set forth herein support that such an effect occurs also in human cells. Moreover, recent Gene Array data on MSCs stimulated by FSH revealed upregulation of several genes involved in angiogenesis and pro-angiopoietic factors signaling.

In conclusion, disclosed herein for the first time is that both human HSPCs and VSELs, like their murine counterparts, were expressed the entire panel of pituitary and gonadal SexH receptors. Most importantly, however, SexHs alone did not stimulate in vitro proliferation of HSPCs. Rather, they co-stimulated clonogenic growth of human HSPCs if added to suboptimal doses of hematopoietic cytokines and growth factors. SexHs also stimulated proliferation of MSCs and increased their pro-angiopoietic potential. Finally, the results presented herein also lend support to studying the effects of SexHs in malignant hematopoiesis.

Materials and Methods Employed in Examples 4-6

Mice

Pathogen-free, 4-6 week-old C57BL/6 mice were obtained from The Jackson Laboratory (Bar Harbor, Me.). In some of the experiments, ovariectomized C57BL/6 mice were purchased from the National Cancer Institute (Bethesda, Md.). Animal procedures were approved by the Local Ethics Committee and performed in accordance with guidelines for laboratory animal care. All efforts were made to minimize animal suffering and the number of animals used.

Isolation of Murine HSPCs and VSELs

Murine HSPCs and VSELs were isolated by flushing bones, bone marrow (BM) cell suspensions were lysed in BD lysing buffer (BD Biosciences, San Jose, Calif.) for 15 minutes at room temperature, and washed twice in phosphate-buffered saline (PBS). VSELs (Sca-1$^+$/Lin$^-$/CD45$^-$) and HSPCs (Sca-1$^+$/Lin$^-$/CD45$^+$) were isolated by multiparameter, live-cell sorting (Influx, Becton, Dickinson and Company, Franklin Lakes, N.J.) and analyzed by flow cytometry (Navios, Beckman Coulter, Inc., Indianapolis, Ind.), as described previously (see Suszynska et al., 2014b; Zuba-Surma & Ratajczak, 2010).

Isolation of Sca-1$^+$ Cells from BM

BM cells were obtained from the femurs and tibias of C57BL/6 mice, and mononuclear cells were separated by FICOLL-PAQUE™ density gradient (FICOLL-PAQUE™ PLUS; GE Healthcare Bio-Sciences, Pittsburgh, Pa.). To obtain Sca-1-positive cells, magnetic-activated cell sorting of Sca-1-stained cells was performed according to the manufacturer's protocol (Miltenyi Biotec, Inc., San Diego, Calif.). In some of the experiments, murine Sca-1$^+$/Kit$^+$/Lin$^-$ (SKL) cells were isolated by MOFLO™ XDP (Beckman Coulter, Inc., Brea, Calif.) as described in Ratajczak et al., 2011b.

Hormone Treatment of Mice In Vivo

Normal 2-month-old C57BL/6 mice were exposed to daily injections of FSH (5 IU/mice/day), LH (5 IU/mice/day), PRL (1 mg/mice/1 day), danazol (4 mg/kg/day), and estrogen (20 mg/mouse/day). Hormone treatment was performed for 10 days.

FACS Analysis

The following mAbs were employed to stain Lin⁻/Sca-1⁺/CD45⁻ and Lin⁻/Sca-1⁺/CD45⁺ cells: biotin-conjugated rat anti-mouse Ly-6A/E (Sca-1, clone E13-161.7), streptavidin-PE-Cy5 conjugate, anti-CD45-APC-Cy7 (clone 30-F11), anti-CD45R/B220-PE (clone RA3-6B2), anti-Gr-1-PE (clone RB6-8C5), anti-TCRαβ-PE (clone H57-597), anti-TCRγζ-PE (clone GL3), anti-CD11b-PE (clone M1/70), and anti-Ter-119-PE (clone TER-119). All mAbs were added at saturating concentrations, and the cells were incubated for 30 minutes on ice, washed twice, and then resuspended for sorting in cell-sorting medium containing 1× Hank's Balanced Salt Solution without phenol red (GIBCO™, a division of Thermo Fisher Scientific Inc., Waltham, Mass.), 2% heat-inactivated fetal calf serum (GIBCO™), 10 mM HEPES buffer (GIBCO™), and 30 U/mL gentamicin (GIBCO™) at a concentration of 5×10⁶ cells/mL. Sca-1⁺/Lin⁻/CD45⁻ cells (VSELs) and Sca-1⁺/Lin⁻/CD45⁺ cells (HSCs) were isolated according to the gating and sorting strategy described in Zuba-Surma & Ratajczak, 2010 and Suszynska et al, 2014b. Proliferation events in BM-derived VSEL and HSC populations were examined by BrdU incorporation followed by flow cytometry.

In Vivo BrdU Treatment

Adult C57BL/6 mice (4-8 weeks old; Jackson Laboratory) were intraperitoneally (i.p.) were injected daily with 1 mg of BrdU solution to evaluate whether SexHs affect proliferation of stem cells, and the final injection of BrdU was performed 1 hour before sacrificing the animals (see Grymula et al, 2014). MNCs were subsequently isolated from BM after lysis of erythrocytes and to immunostained for expression of Sca-1, CD45, and Lin markers as described in Zuba-Surma & Ratajczak, 2010, as well as for the presence of BrdU (FITC BrdU Flow Kit; BD PHARMINGEN™, Becton, Dickinson and Company, Franklin Lakes, N.J.). Samples were analyzed with a Navios flow cytometer (Beckman Coulter).

Clonogenic Assays In Vivo

BM-derived (2×10⁵) or PB-derived (4×10⁵) cells or FACS-sorted SKL (2×10³) cells were resuspended in 0.4 mL of RPMI-1640 medium and mixed with 1.8 mL of METHOCULT™ HCC-4230 methylcellulose medium (STEMCELL™ Technologies Inc., Vancouver, British Columbia, Canada), supplemented with L-glutamine and antibiotics. Specific murine recombinant growth factors (all purchased from R&D Systems, Inc., Minneapolis, Minn.) were added at suboptimal doses. Specifically, to stimulate granulocyte-macrophage colony-forming units (CFU-GM), IL-3 (10 ng/mL) and granulocyte-macrophage colony stimulating factor (GM-CSF; 25 ng/mL) were used, while erythropoietin (EPO; 5 U/mL) was used to stimulate erythrocyte burst-forming units (BFU-E), and megakaryocyte colony-forming unites (CFU-Megs) were stimulated by thrombopoietin (50 ng/mL).

The colonies were counted under an inverted microscope after 7-10 days of culture. Each clonogenic assay was performed in quadruplicate.

Signal Transduction Studies

Cells were kept in RPMI medium containing 0.5% BSA overnight in an incubator to achieve quiescence; then stimulated with FSH (5 IU), LH (5 IU), danazol (4 mg/mL), PRL (1 mg/mL), estradiol (0.1 mM), progesterone (0.1 mM), or vehicle only (0.9% sodium chloride diluted in medium with 0.5% BSA) for 5 or 10 minutes at 37° C.; and finally lysed for 20 min on ice with RIPA Lysis Buffer System (Santa Cruz Biotechnology, Inc., Santa Cruz, Calif.) containing protease and phosphatase inhibitors (Santa Cruz Biotechnology). The concentrations of extracted proteins were measured with the BCA Protein Assay Kit, according to the manufacturer's instructions (Thermo Fisher Scientific), and equal amounts of protein were separated and analyzed for phosphorylation of MAPKp44/42 and AKT (Ser473). Loading of the lanes was evaluated by stripping the blots and reprobing with antibodies against MAPKp44/42 and AKT. All phosphospecific antibodies were purchased from Cell Signaling Technology, Inc. (Danvers, Mass.) The membranes were developed with an AMERSHAM™ ECL™ Western Blotting Detection Reagents kit and exposed to AMERSHAM™ HYPERFILM™ (GE Healthcare Life Sciences, Little Chalfont, Buckinghamshire, United Kingdom).

Real-Time Polymerase Chain Reaction for SexH Receptor Expression

For analysis of SexH receptor expression at the mRNA level, total mRNA was isolated from cells with the RNEASY® Mini Kit (Qiagen, Inc., Valencia, Calif.), and mRNA was reverse transcribed with TAQMAN® Reverse Transcription Reagents (Thermo Fisher Scientific). Detection of target genes and β2-microglobulin mRNA levels was performed by real time polymerase chain reaction (RT-PCR) using an ABI PRISM® 7500 Sequence Detection System (APPLIED BIOSYSTEMS™, a division of Thermo Fisher Scientific). A 25-mL reaction mixture contained 12.5 mL SYBR Green PCR Master Mix, 10 ng of cDNA template, and forward and reverse primers. Primers were designed with PRIMER EXPRESS® software (APPLIED BIOSYSTEMS™; see Table 2). The threshold cycle (Ct), that is, the cycle number at which the amount of amplified gene of interest reached a fixed threshold, was subsequently determined. The relative quantitation of target gene mRNA expression was calculated with the comparative Ct method. The relative quantitative value of the target, normalized to an endogenous β2-microglobulin gene control and relative to a calibrator, is expressed as 2-DDCt (fold difference), whereas DCt=Ct of target genes—Ct of an endogenous control gene (β2-microglobulin), and DCt=DCt of samples measuring the target gene—DCt of samples measuring the calibrator for the target gene. To avoid the possibility of amplifying contaminating DNA (i) all of the primers for real-time RT-PCR were designed to contain a DNA intron sequence for specific cDNA amplification, (ii) reactions were performed with appropriate negative controls (template-free controls), (iii) uniform amplification of the products was rechecked by analyzing the melting curves of the amplified products (dissociation graphs), (iv) the melting temperature (Tm) was in the range 57° C.-60° C., with the product Tm at least 10° C. higher than the primer Tm, and v) gel electrophoresis was performed to confirm the correct size of the amplified products and the absence of nonspecific bands.

Fluorescent Staining of the Sorted Cells

BM-derived Lin⁻/Sca-1⁺/CD45⁻ (VSELs) and Lin⁻/Sca-1⁺/CD45⁺ (HSPCs) cells were fixed in 3.5% paraformaldehyde for 20 minutes, permeabilized with 0.1% Triton™

X-100 for 5 minutes, washed in PBS, pre-blocked with 2.5% BSA, and subsequently stained with antibodies to follicle-stimulating hormone receptor (FSH-R, 1:200, rabbit polyclonal antibody; Santa Cruz), luteinizing hormone/choriogonadotropin receptor (LH-R, 1:200, rabbit polyclonal antibody; Santa Cruz), androgen receptor (1:200, rabbit polyclonal antibody; Thermo Scientific), and estrogen receptor (1:200, mouse monoclonal IgG antibody; Thermo Scientific). Staining was performed for 75 minutes at 37° C. Antibodies were diluted in 2.5% BSA in PBS. Appropriate secondary antibodies labeled with TEXAS RED® brand red fluorescent dye (1:400; Vector Laboratories Inc., Burlingame, Calif.) were used (TEXAS RED® brand red fluorescent dye-labeled Goat Anti-Rabbit IgG and TEXAS RED® brand red fluorescent dye-labeled Horse Anti-Mouse IgG) for staining for 75 minutes at 37° C. In control experiments, cells were stained with secondary antibodies only. The nuclei were labeled with DAPI. The fluorescence images were collected with a confocal laser scanning microscope, FLUOVIEW™ FV1000 (Olympus Corporation of the Americas, Waltham, Mass.).

PB Counts

Fifty microliters of PB was taken from the retro-orbital plexus of the mice and collected into microvette EDTA-coated tubes (Sarstedt AG & Co., Nümbrecht, Germany). Samples were run within 2 hours of collection on a HEMAVET® 950 hematology analyzer (Drew Scientific Inc., Oxford, Conn.) as described in Borkowska et al., 2014.

White Blood Cell, Platelet, and Hematocrit Recovery

Mice were irradiated with a sublethal dose of 650 cGy and then injected for 10 days with vehicle control (Thermo Fisher Scientific), FSH (5 IU/day), LH (5 IU/day), PRL (1 mg per mouse per day), or danazol (4 mg/kg/day; Sigma Aldrich). Blood was collected on days 0, 3, 7, 14, 21, and 28, and white blood cell (WBC), platelet, red blood cells (RBC), and hematocrit were measured on a HEMAVET® instrument (HV950FS; Drew Scientific Inc.) as described in Borkowska et al, 2014. Experiments were performed twice (each time, n=5).

Statistical Analysis

The data were analyzed using Student's t-test or one-way analysis of variance (ANOVA) with the Bonferroni post-hoc test. The GraphPad Prism 6.0 program (GraphPad Software, Inc., La Jolla, Calif.) was employed, and p values <0.05 were considered to indicate statistically significant differences. Data from murine HSPCs and VSELs proliferation both in vivo and in vitro after stimulation by SexHs were expressed as mean±SEM. Differences were analyzed using ANOVA (one way or multiple comparisons) as appropriate. Post hoc multiple-comparison procedures were performed using two-sided Dunnett or Dunn tests as appropriate with control samples as the control category. The significance level throughout the analyses was chosen to be 0.05. All statistical analyses were performed using the GraphPad Prism 6.0 statistical software.

Example 4

Figure 8A:
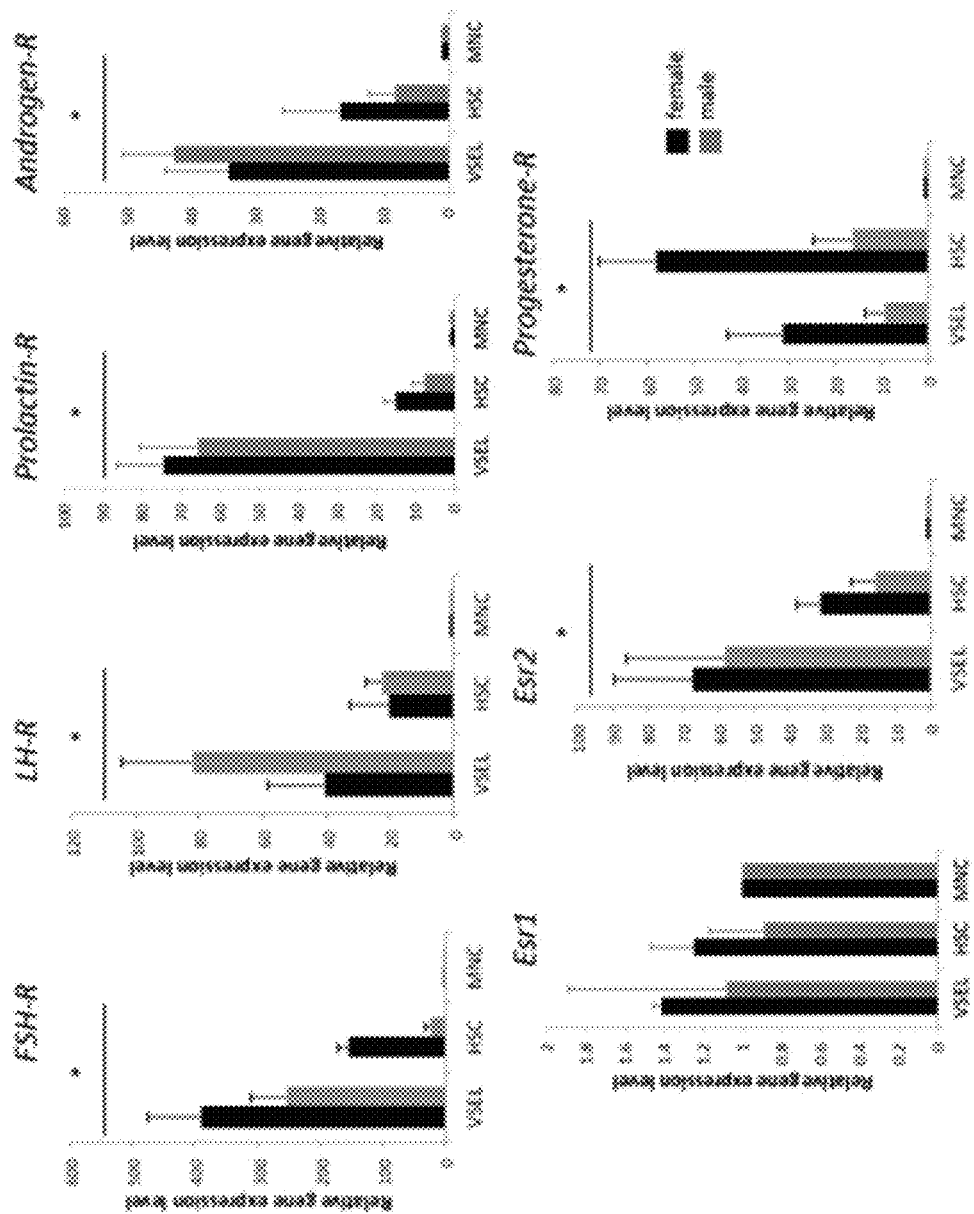
FIGS. 8A-8D depict the results of experiments demonstrating that murine HSPCs and VSELs express functional SexHs receptors.

Murine BM-purified HSPCs and VSELs Express mRNA for Several Pituitary and Gonadal SexHs To shed more light on the role of SexHs in hematopoiesis and to address a potential developmental link between hematopoiesis and the germline, the expression of receptors for pituitary (FSH, LH, PRL) and gonadal (androgen, estrogen, and progesterone) SexHs in Sca-1$^+$/Lin$^-$/CD45$^+$ cells (HSPCs) as well as small Sca-1$^+$/Lin$^-$/CD45$^-$ cells (VSELs) purified from BM was analyzed and compared with expression in normal BM MNCs (FIG. 8A). It was observed that, except for estrogen receptor 1 alpha (Esr1), all receptors were expressed by both HSPCs and VSELs. However, there were some differences in expression between female and male mice; in particular, the progesterone receptor was expressed at much higher levels in VSELs and HSPCs of females than of males, in contrast to LHR, which was expressed at higher levels in male VSELs. Overall, VSELs tended to express mRNA for SexHs at higher levels than HSPCs, with the exception of the progesterone receptor, which was highly expressed in female HSPCs.

Figure 8B:
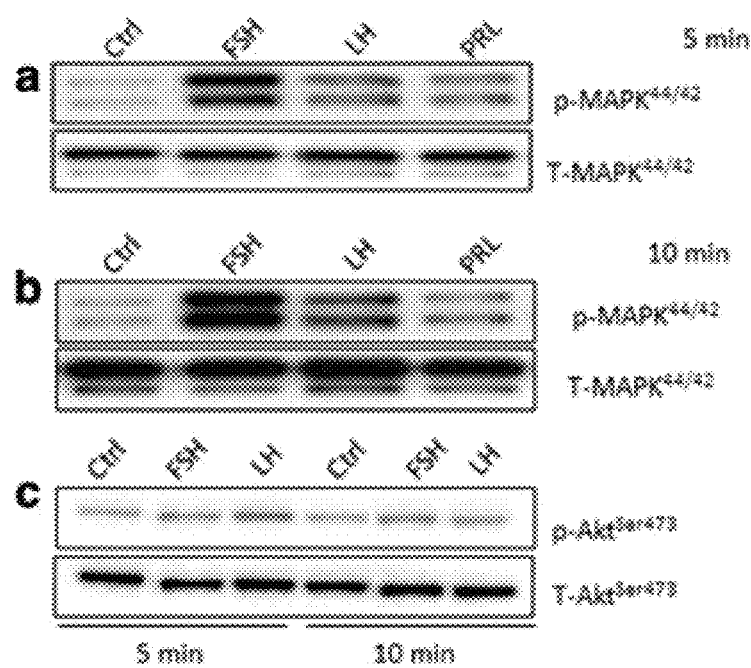

Subsequently, to test whether these receptors were functional, Sca-1$^+$ BMMNCs were sorted using immunomagnetic beads and their responsiveness to SexH stimulation was evaluated by western blot analysis of MAPKp42/44 and AKT phosphorylation (FIG. 8B). It was found that all pituitary SexHs tested in these studies stimulated MAPKp42/44 phosphorylation in purified Sca-1$^+$ BMMNCs. The strongest stimulation of MAPKp42/44 after 5 and 10 minutes was observed after administration of FSH, followed by LH and PRL. The activation of MAPKp42/44 was similar in male and female mice.

Figure 8C:
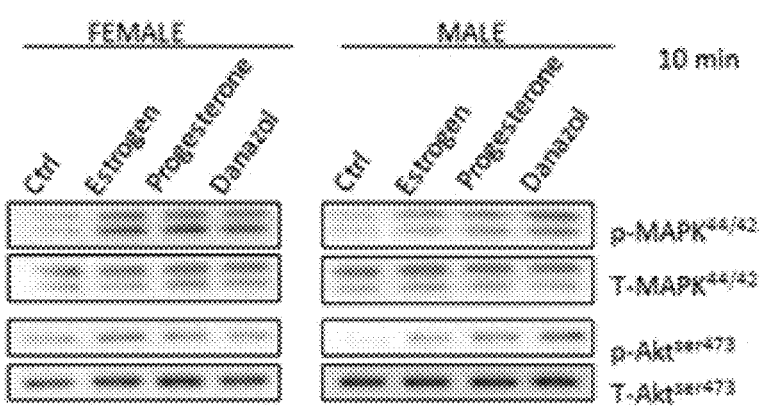

The responsiveness of sorted Sca-1$^+$ BMMNCs was also determined using immunomagnetic beads to gonadal SexHs (FIG. 8C). Because of the short 4-day estrus cycle in mice and rapid fluctuation in the level of estrogens circulating in the blood, ovariectomized females were employed in this experiment. As shown, gonadal SexHs stimulated MAPKp42/44 both in female and in male mouse-derived Sca-1$^+$ BMMNCs. Male mice also responded to gonadal SexH stimulation by phosphorylation of AKT.

Figure 8D:
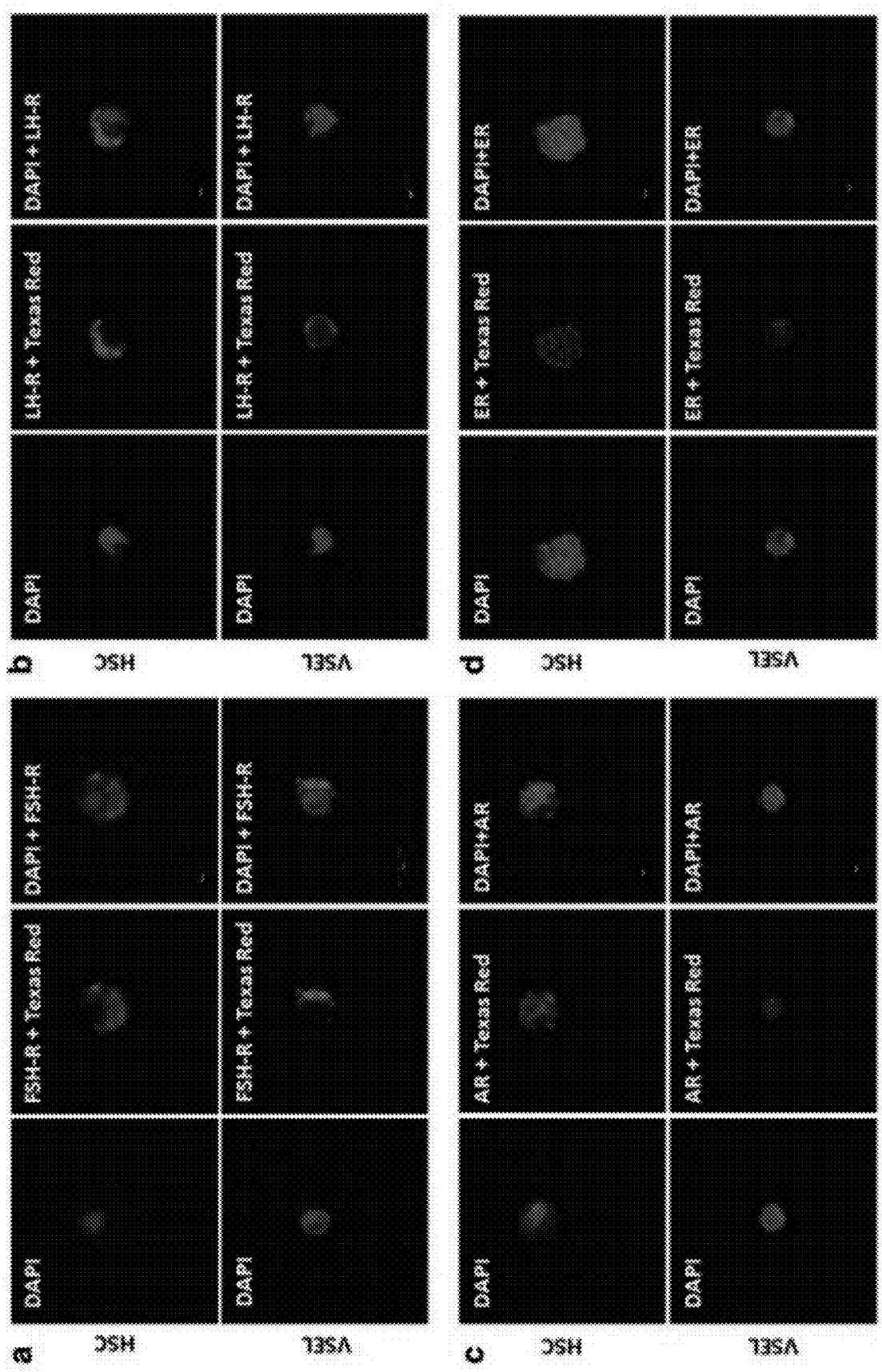

Final evidence for the expression of SexHs receptors by murine BM-derived HSCPs and VSELs was performed by immunofluorescence staining. As shown in FIG. 8D, both FACS sorted from BM murine HSPCs and VSELs expressed pituitary SexHs receptors (FSH-R and LH-R) as well as receptors for intracellular gonadal SexHs (Androgen-R and Estrogen-R).

Example 5

Effect of In Vivo Administration of SexHs on Proliferation of Murine BM-residing HSPCs and VSELs Since HSPCs and VSELs expressed SexHs receptors (FIG. 8A), whether they also responded to these hormones in vivo was tested. This is an especially important question for BM-residing VSELs, which are reportedly a highly quiescent population of stem cells (see Shin et al., 2009) but under appropriate macroenvironmental conditions can give rise to HSPCs (see e.g., Ratajczak et al., 2011a; Ratajczak et al, 2011b).

To address this issue, female and male mice were exposed to daily s.c. injection for 10 days of pituitary (FSH, LH, PRL) and gonadal (androgen, estrogen, and danazol) SexHs. In parallel with hormone therapy, mice were administered BrdU i.p. Control mice received vehicle instead of SexHs but were also administered BrdU.

Figure 9A:
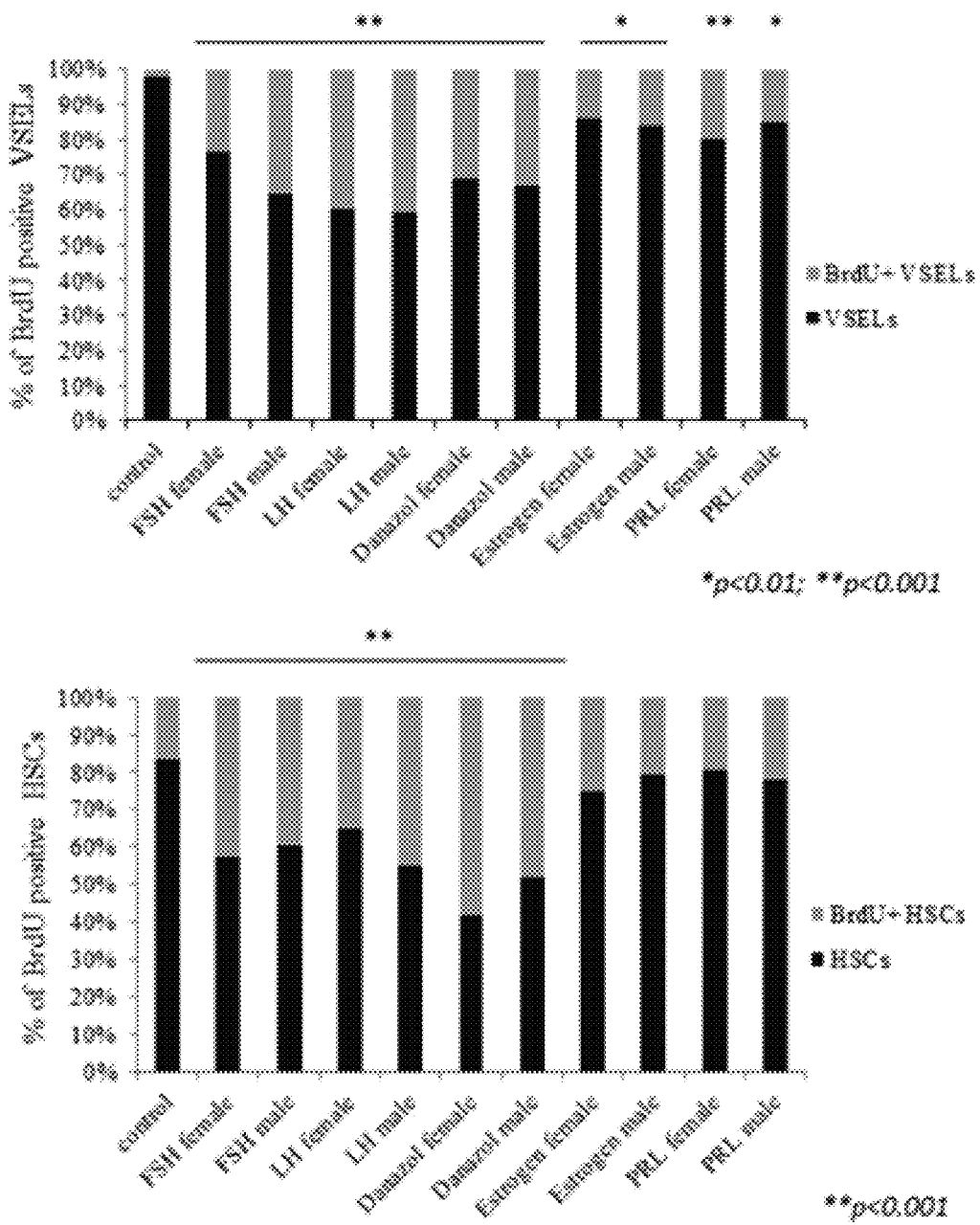
FIGS. 9A-9C are a series of bar graphs showing that murine HSPCs and VSELs proliferated both in vivo and in vitro after stimulation by SexHs.

It was determined that 10-day administration of each of the SexHs evaluated in this experiment directly stimulated proliferation of VSELs and HSPCs in vivo, as evaluated by the percentage of cells that incorporated BrdU. Specifically, the percentage of quiescent BrdU$^+$ Sca-1$^+$/Lin$^-$/CD45$^-$ cells increased from about 2% to about 15-40% (FIG. 9A). The highest response was observed for LH, FSH, and danazol for both female and male cells and for PRL for female cells. An increase in the percentage of BrdU$^+$ Sca-1$^+$/Lin$^-$/CD45$^+$ cells from about 20% to 25-60% was also observed, with the highest increases after injections of danazol, LH, and FSH (FIG. 9A).

Figure 9B:
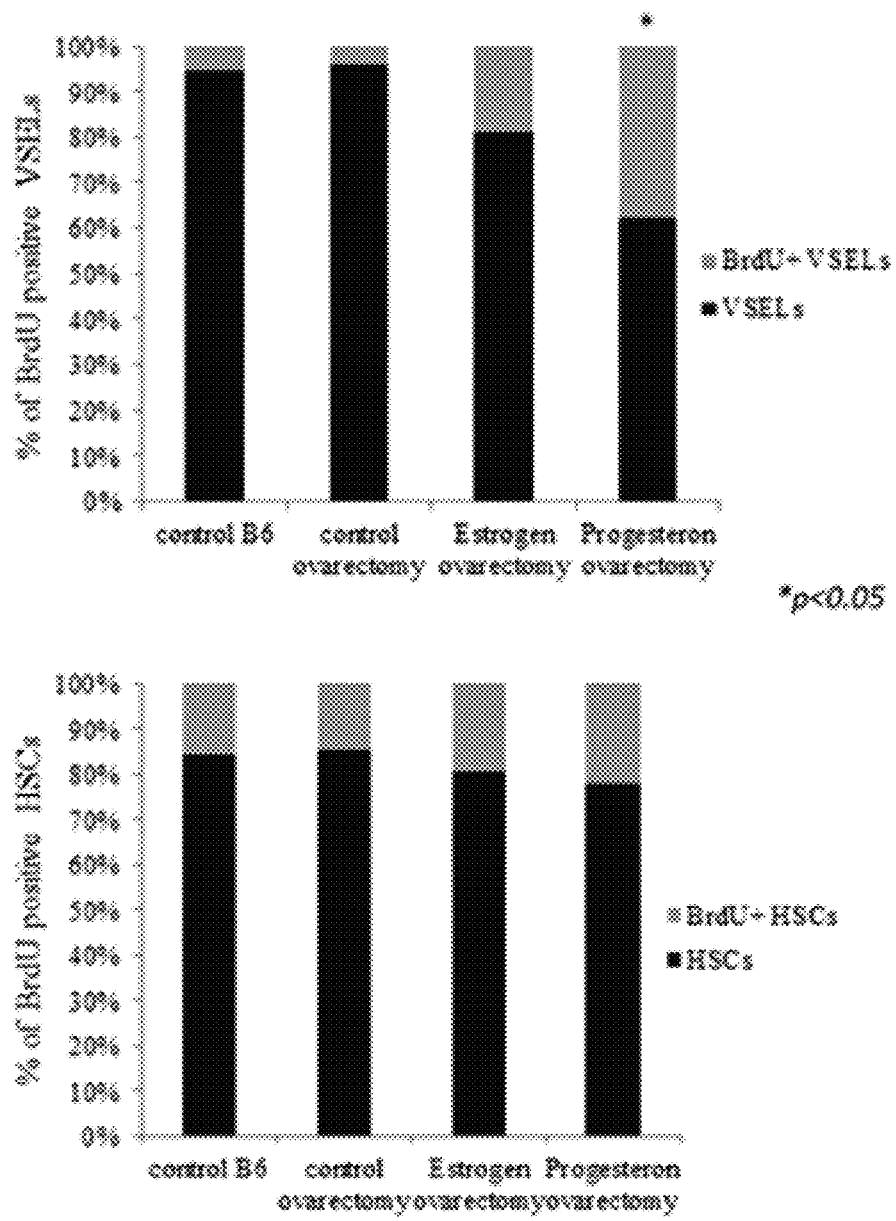

Because of the short estrus cycle, the effect of estradiol and progesterone on BrdU accumulation by BM-residing VSELs and HSPCs was evaluated in ovariectomized female mice. FIG. 9B shows that progesterone enhanced BrdU incorporation, particularly in small Sca-1$^+$/Lin$^-$/CD45$^-$ VSELs. However, a small increase in BrdU incorporation into the population of Sca1$^+$/Lin$^-$/CD45$^+$ HSPCs was simultaneously observed.

Figure 9C:
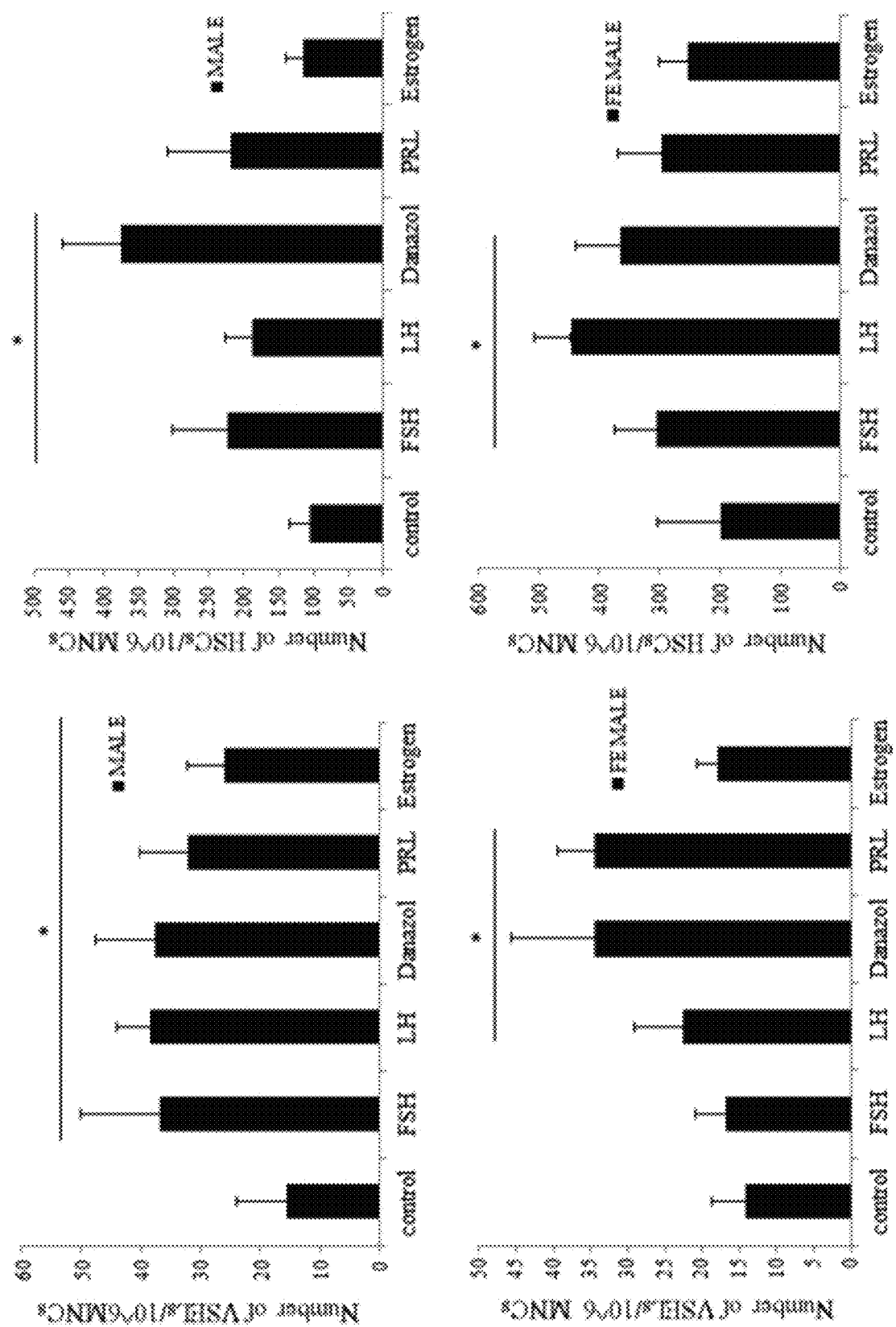

Whether SexHs increased the total number of both VSELs and HSPCs in BM as measured by FACS was also evaluated. See FIG. 9C. The total number of VSELs/10$^6$ BMMNCs increased in male BM by about 2.5-fold after 10-day administration of FSH, LH, PRL, danazol, and estrogen. In female mice, the most effective SexHs were PRL, danazol, and LH. Simultaneously, an increase in BM HSPCs/10$^6$ BMMNCs was observed, with the highest stimulatory effect for danazol, LH, and FSH in both male and female mice.

The observed differences between the number of cells accumulating BrdU (FIG. 9B) and the increase in the total number of cells (FIG. 9C) could have depended on differences in proliferation kinetics between the tested cells.

Example 6

Figure 10:
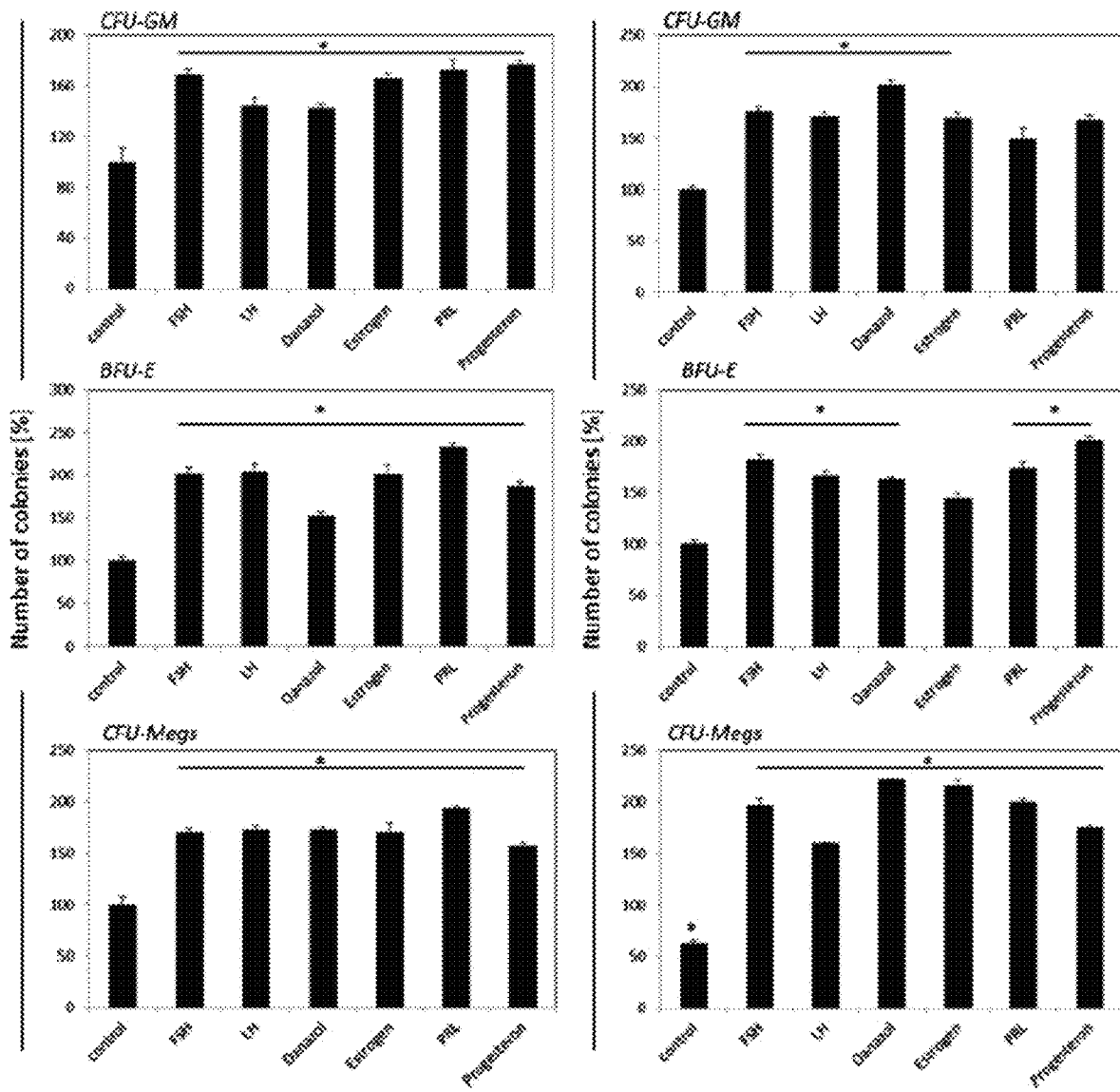
FIG. 10 is a series of bar graphs showing that SexHs co-stimulated in vitro proliferation of murine Sca-1$^+$/Kit$^+$/Lin$^-$ (SKL) cells if added with suboptimal (1/10) concentrations of colony-stimulating cytokines and growth factors. Left panels: female Sca-1$^+$ cell-derived CFU-GM, BFU-E, and CFU-Meg colonies; right panels: male Sca-1$^+$ cells-derived CFU-GM, BFU-E, and CFU-Meg colonies. The number of colonies formed in absence of SexH was assumed to be 100%. Data are combined from four independent experiments. *p<0.05 compared with control group. BFU-E, erythrocyte burst-forming units; CFU-GM, granulocyte-macrophage colony-forming units.

In Vitro and In Vivo Effects of SexHs on Clonogenicity of Murine CFU-GM, BFU-E, and CFU-Megs To assess the effect of SexHs on clonogenic growth of murine HSPCs, in vitro clonogenic assays were performed on Sca-1$^+$/Kit$^+$/Lin$^-$(SKL) BMMNCs stimulated to grow CFU-GM, BFU-E, and CFU-Meg colonies in the presence or absence of SexHs. To better assess the effect of SexHs on clonogenic growth of hematopoietic progenitors, the appropriate growth factors and cytokines were employed at a suboptimal dose (i.e., one-tenth of their optimal dose). See FIG. 10.

Figure 11:
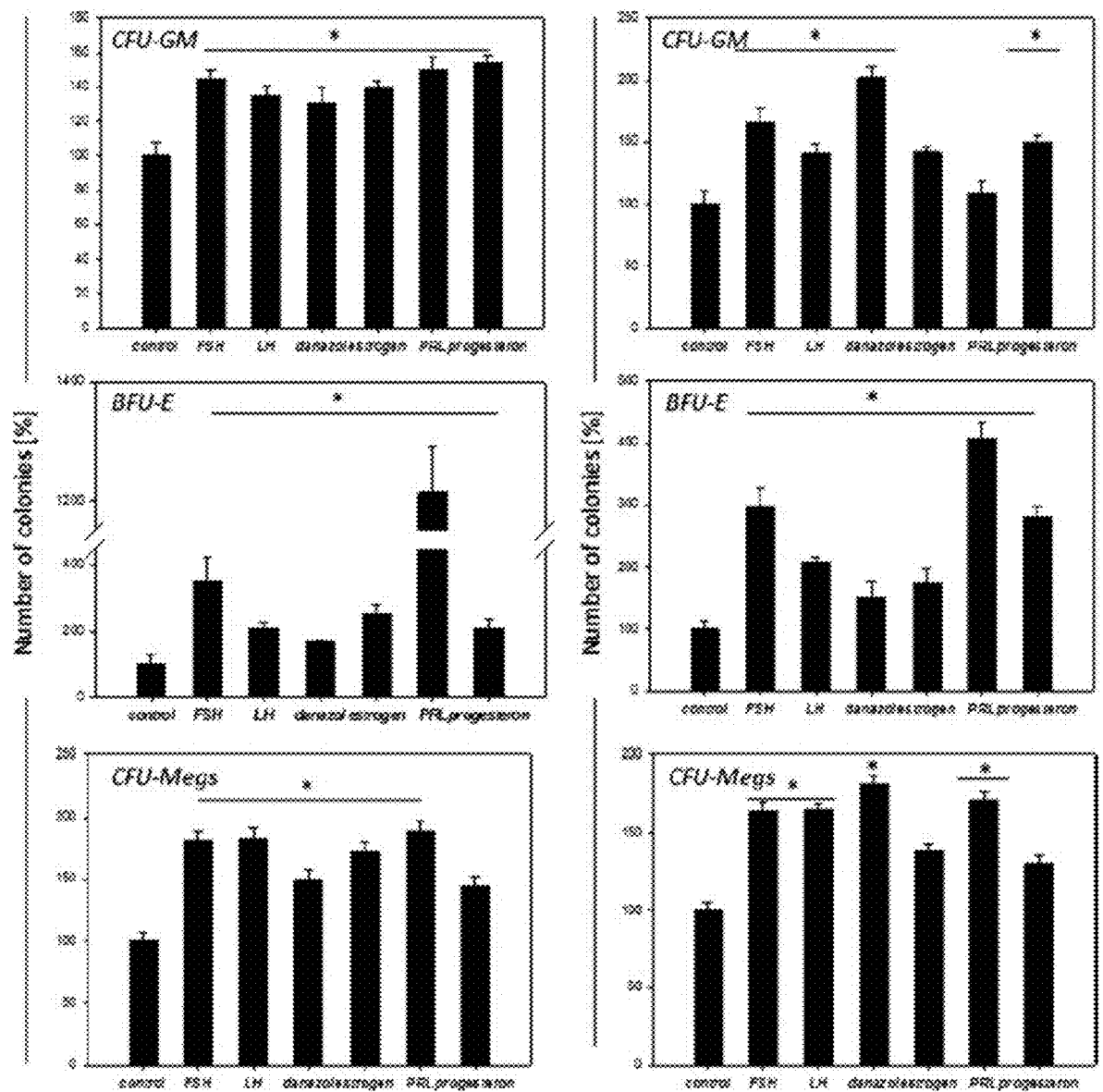
FIG. 11 is a series of bar graphs showing that SexHs co-stimulated in vitro proliferation of murine Sca-1$_+$/Kit$^+$/Lin$^-$ (SKL) cells if added with suboptimal (1/10) concentrations of colony-stimulating cytokines and growth factors. Left panels: female Sca-1$^+$ cell-derived CFU-GM, BFU-E, and CFU-Meg colonies; right panels: male Sca-1$^+$ cells-derived CFU-GM, BFU-E, and CFU-Meg colonies. The number of colonies formed in absence of SexH was assumed to be 100%. Data are combined from four independent experiments. *p<0.05 compared with control group. BFU-E, erythrocyte burst-forming units; CFU-GM, granulocyte-macrophage colony-forming units.

It was observed that SexHs enhanced clonogenic growth of CFU-GM, BFU-E, and CFU-Meg colonies, for female- as well as for male-derived cells. Similar data were obtained for less purified Sca-1$^+$ cells (see FIG. 11).

Figure 12:
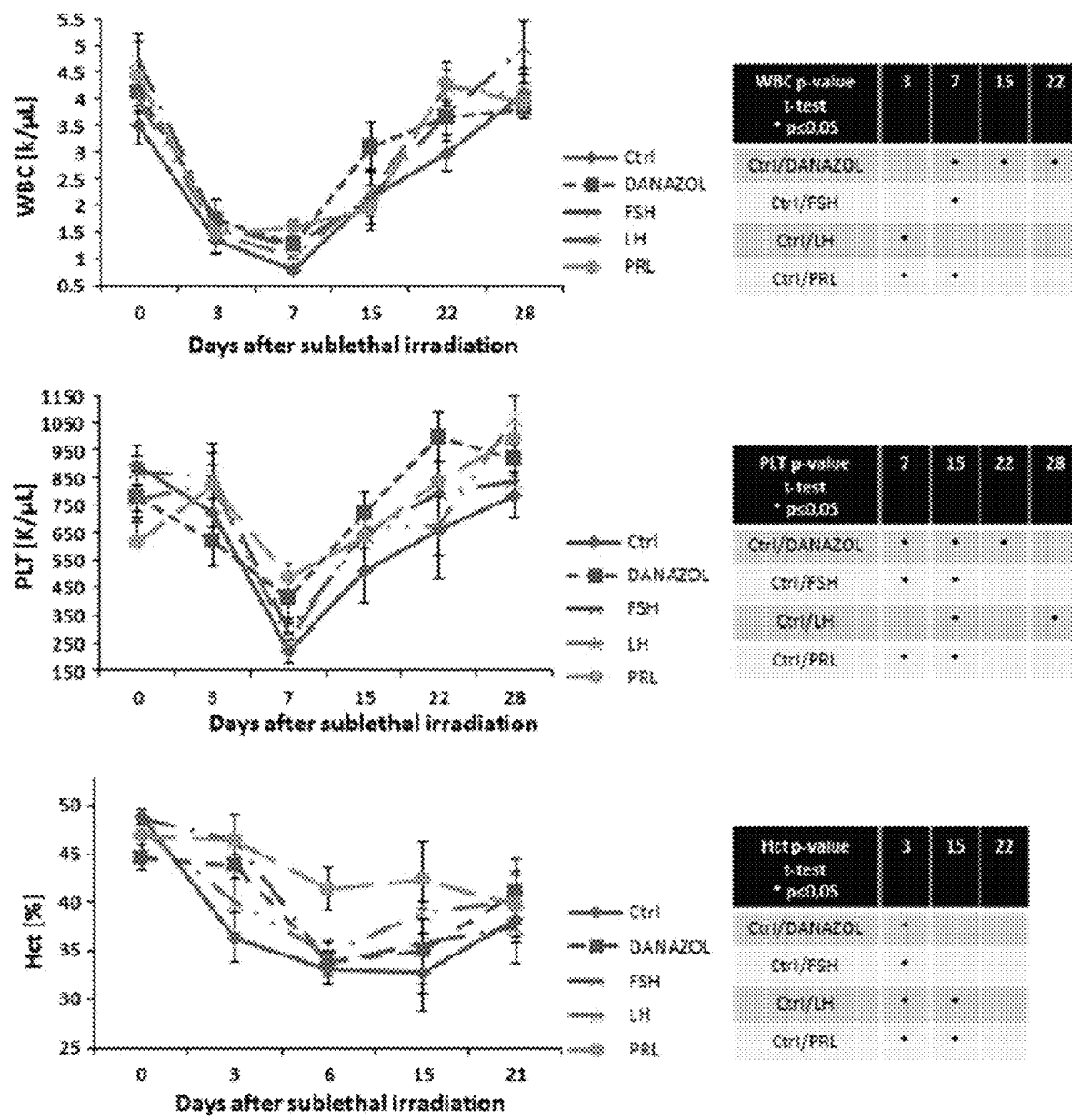
FIG. 12 depicts the results of experiments showing that SexHs accelerated hematopoietic recovery in sublethally irradiated mice. Mice were irradiated with a sublethal dose of gamma irradiation (650 cGy) and subsequently injected for 10 days with: control vehicle, FSH (5 IU), LH (5 IU), PRL (1 mg), or danazol (4 mg/kg per day). White blood cells (WBC) and platelets were counted at intervals (0, 3, 7, 15, 22, and 28 days after irradiation). Hematocrit (Hct) was measured at 0, 3, 6, 15, and 21 days after irradiation. Results are combined from two independent experiments (5 mice per group, n=10). *p<0.05—results of statistical analyses are shown in right panel tables. PRL, prolactin. Blue diamonds: control; red squares: Danazol; purple carets: FSH; aquamarine asterisks: LH; and orange circles: PRL.
Figure 13:
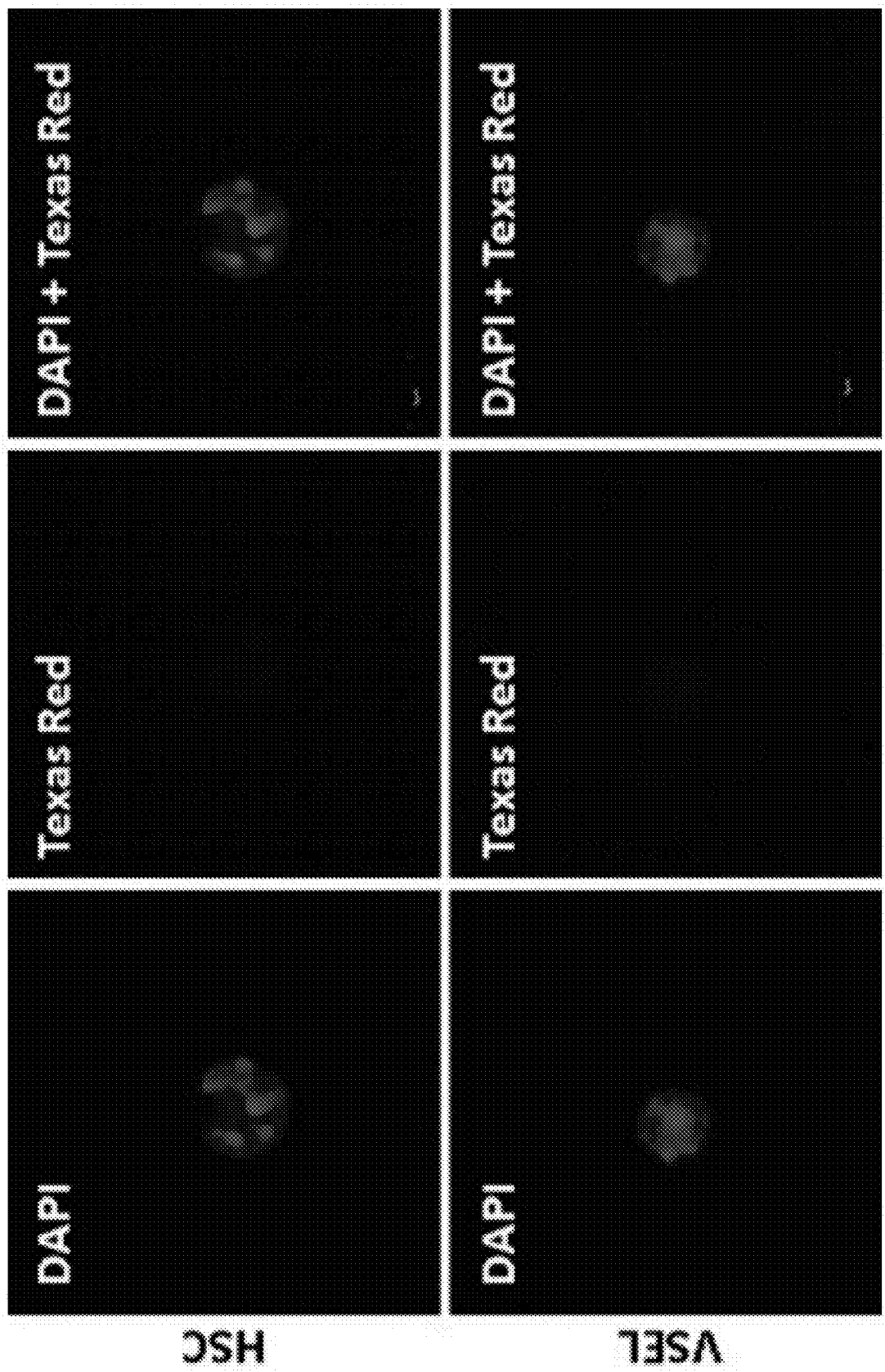
FIG. 13 is a series of fluorescent images of an example of control staining showing that secondary antibody conjugated with TexR did not bind to cells if primary antibody was not employed.

The recovery of PB counts in mice that were sublethally irradiated and subjected to injections of SexHs was evaluated (FIG. 12). A particularly statistically significant increase in leucocyte counts after administration of danazol and PRL and platelets counts on day 15 after administration of all tested SexHs was observed.

Discussion of Examples 4-6

Disclosed herein is discovery that HSPCs expressed functional receptors not only for gonadal SexHs, as reported in Carreras et al., 2008; Maggio et al., 2013; and Nakada et al., 2014; but also, as disclosed herein, for pituitary FSH and LH. Also disclosed is the discovery that also some BM-residing cells enriched for VSELs also expressed functional SexHs receptors. The expression of pituitary and gonadal SexHs receptors by these cells has been demonstrated at both mRNA and protein levels. This intriguing observation supported a potential developmental link between germ line, some VSELs, and HSPCs.

The development of HSPCs is still an intriguing phenomenon, because the first primitive primitive RBC appear to enter the circulation as nucleated erythrocytes (Palis, 2014). The question of what happens with hemangioblasts after the early stages of embryogenesis is still open. Do they contribute to the wave of definitive hematopoiesis, or are they eliminated at the time when definitive hematopoiesis emerges? Interestingly, it has been reported that hemangioblasts can still be recovered from adult BM (Guthrie et al., 2005).

In contrast to primitive hematopoiesis, definitive hematopoiesis is initiated a few days later at the 11th d.p.c. in the hemogenic endothelium of the dorsal aorta in the so-called aorta-gonad-mesonephros (AGM) region. The origin of HSPCs in this region (Ivanovs et al., 2011) as well as the role of the initiation of circulation in the embryo (Lux et al., 2008), the influence of shear forces (Adamo et al., 2009) in the appearance of the first definitive HSPCs in the AGM, and the role of other locations of putative hemogenic endothelium, for example, the placenta vasculature (Lee et al., 2010), are still under debate.

Moreover, recent reports on the existence of developmentally early stem cells with broader specification potential in BM (Shin et al., 2010; Suszynska et al., 2014b) pose two of the most important questions in developmental biology: what is the hierarchy within the stem cell compartment in murine BM, and are there remnants of embryonic development found in adult BM (Jiang et al., 2002; D'Ippolito et al., 2004; McGuckin et al., 2005; Nayernia et al., 2006; Bhartiya et al., 2012; Havens et al., 2013; Kassmer et al., 2013; Havens et al., 2014; Suszynska et al., 2014b)?

While it has been proposed that primitive and definitive hematopoiesis are independent events in embryonic development and that a primary source of HSPCs is hemogenic endothelium in the dorsal aorta (see e.g., Lux et al., 2008), parallel evidence has accumulated that HSPCs can become specified from a population of migrating PGCs during embryogenesis (Rich, 1995; Suszynska et al., 2014b). PGCs are the first stem cells to be specified as a separate population in the proximal part of the embryo proper at about 7 d.p.c., and right after specification these cells leave the embryo proper. Accordingly, shortly before the beginning of gastrulation, they migrate into the extraembryonic endoderm close to the yolk sac at the bottom of the allantois, where the first hemangioblasts and hematopoietic islands emerge, and subsequently return to the embryo proper and migrate into the genital ridges through the primitive streak, crossing the AGM region at around 11 d.p.c. (Leitch et al., 2013). During migration, PGCs amplify in number and change expression of some genes, so that, based on their molecular signature, early-migrating, migrating, and post-migrating PGCs can be distinguished. These latter cells are the precursors of gametes. This migratory route of PGCs and the appearance of primitive and definitive hematopoiesis raise the possibility that HSPCs could be derived from early PGCs (hemangioblasts in the yolk sac) or late-migratory PGCs (in hemogenic endothelium in the AGM region). In fact, it has been demonstrated in some species that migrating PGCs may go astray during their migration to the developing gonads and settle in other tissues (Jordan, 1917).

In support of the intriguing concept of a developmental link between PGCs and HSPCs, it has been demonstrated that murine PGCs isolated from embryos (Rich, 1995), stem cells isolated from murine testes (Yoshimoto et al., 2009), and teratocarcinoma cell lines (Miwa et al., 1991) can be specified into HSPCs. Functional EpoR is also expressed on murine and human teratocarcinoma and gonadal tumor cell lines (Suszynski et al., 2014a).

VSELs are small, quiescent, Sca-1+Lin−/CD45− stem cells identified in adult murine BM and as CD133+/Lin−/CD45− cells in human BM and umbilical cord blood (Kucia et al., 2006; Kucia et al., 2007). These cells sorted based on surface markers and small size seem to be still somehow heterogeneous as revealed by gene expression analysis performed on single sorted murine VSELs (Sin et al, 2012). However, what is to important, they show multilineage differentiation potential into all three germ layers (Kucia et al., 2006; Havens et al., 2013; Kassmer et al, 2013; Havens et al., 2014) and, under appropriate co-culture conditions with OP-9 stromal cells, some of them can be specified into HSPCs (Ratajczak et al., 2011a; Ratajczak et al., 2011b). They express embryonic stem cell markers such as Oct-4 and Nanog in their nuclei, and some murine VSELs express several markers, including Stella, Prdm14, Fragilis, Blimp1, Nanos3, and Dnd1, which are shared with migratory PGCs (Shin et al, 2010). As mentioned earlier, cDNA studies performed on single sorted VSELs (Shin et al., 2012) revealed differences in Stella expression among these cells, and further studies are needed to better address the developmental origin of these cells. Populations sorted from murine BM VSELs also reportedly express EpoR (Suszynska et al., 2014a) and highly express the hemangioblast marker, Flk-1 receptor. As such, there appears to be a potential developmental link between PGCs, hemangioblasts, VSELs, and HSPCs (Shin et al, 2010).

The data presented herein support the concept that at least some VSELs and HSPCs can be specified during development from epiblast/migrating PGCs, and that VSELs are the most primitive precursors of HSPCs in BM. Moreover, in spite of the expression of pluripotent stem cell markers, changes in the epigenetic signature of imprinted genes (e.g., by erasure of imprinting at the Igf-2-H19 locus) in VSELs are involved in the resistance of these cells to Igf-1/Igf-2 signaling, which keeps these cells quiescent in adult tissues and prevents teratoma formation (Shin et al., 2009). In fact, VSELs might correspond to long-term repopulating hematopoietic stem cells (LT-HSCs), which, similar to PGCs, express a maternal type of imprinting (erasure) at the Igf-2/H19 locus (Ratajczak et al., 2013), and such epigenetic changes in LT-HSCs were recently confirmed (Venkatraman et al, 2013).

While there have been a few reports indicating a responsiveness of HSPCs to gonadal SexHs and PRL (Selleri et al., 1991; Carreras et al., 2008; Maggio et al., 2013; Nakada et al., 2014), disclosed herein is the discovery that HSPCs responded in a manner similar to that of VSELs to pituitary-secreted FSH and LH. This is an interesting observation, taking into consideration that the serum level of FSH increases with age at a time when the function of the gonads decreases.

In conclusion, the data presented herein supported the concept of a potential developmental link between the germline and hematopoiesis, and the presence of VSELs in adult BM and the responsiveness of HSPCs to SexHs lend support to this hypothesis. Moreover, another silent observation is the positive effect of SexHs in sublethally irradiated mice demonstrated herein, which opens up the HSPCs emerge at the 7th day post coitus (d.p.c.) in extraembryonic tissues in the yolk sac blood islands (Palis, 2014). Cells that initiate primitive hematopoiesis in this location are called hemangioblasts and give rise to endothelial cells and new possibility that, besides androgens, some other SexHs could be employed in certain situations to stimulate hematopoietic recovery in the clinic.

REFERENCES

All references listed in the instant disclosure, including but not limited to all patents, patent applications and publications thereof, scientific journal articles, and database entries (including but not limited to GENBANK® biosequence database entries and all citation and annotations presented therein) are incorporated herein by reference in their entireties to the extent that they supplement, explain, provide a background for, and/or teach methodology, techniques, and/or compositions employed herein.

Abramoff et al. (2004) Image Processing with ImageJ. *Biophotonics Int* 11:36-42.

Adamo et al. (2009) Biomechanical forces promote embryonic haematopoiesis. *Nature* 459:1131-1135.

Anand et al. (2015) Chemoablated mouse seminiferous tubular cells enriched for very small embryonic-like stem cells undergo spontaneous spermatogenesis in vitro. *Reprod Biol Endocrinol* 13:33.

Bhartiya et al. (2012) Very small embryonic-like stem cells with maximum regenerative potential get discarded during cord blood banking and bone marrow processing for autologous stem cell therapy. *Stem Cells Dev* 21:1-6.

Bhartiya et al. (2014) Making gametes from pluripotent stem cells—a promising role for very small embryonic-like stem cells. *Reprod Biol Endocrinol* 12:114.

Borkowska et al. (2014) Novel evidence that crosstalk between the complement, coagulation and fibrinolysis proteolytic cascades is involved in mobilization of hematopoietic stem/progenitor cells (HSPCs). *Leukemia* 28:2148-2154.

Caplan et al. (2001) Mesenchymal stem cells: building blocks for molecular medicine in the 21st century. *Trends Mol Med* 7:259-264.

Carreno et al. (2005) Prolactin affects both survival and differentiation of T-cell progenitors. *J Neuroimmunol* 160:135-145.

Carreras et al. (2008) Estradiol acts directly on bone marrow myeloid progenitors to differentially regulate GM-CSF or Flt3 ligand-mediated dendritic cell differentiation. *J Immunol* 180:727-738.

Chaganti et al. (1989) Leukemic differentiation of a mediastinal germ cell tumor. *Genes Chromosomes Cancer* 1:83-87.

D'Ippolito et al. (2004) Marrow-isolated adult multilineage inducible (MIAMI) cells, a unique population of postnatal young and old human cells with extensive expansion and differentiation potential. *J Cell Sci* 117:2971-2981.

De Feo et al. (1991) Effect of estrogens and progesterone on human peripheral erythroid burst-forming unit (BFU-E) growth. *Am J Hematol* 38:81-85.

De Miguel et al. (2009) Epiblast-derived stem cells in embryonic and adult tissues. *Int J Dev Biol* 53:1529-1540.

Dugan et al. (2002) Effects of prolactin deficiency on myelopoiesis and splenic T lymphocyte proliferation in thermally injured mice. *Endocrinology* 143:4147-4151.

Geiger et al. (2002) Analysis of the hematopoietic potential of muscle-derived cells in mice. *Blood* 100:721-723.

Grymula et al. (2014) Evidence that the population of quiescent bone marrow-residing very small embryonic/epiblast-like stem cells (VSELs) expands in response to neurotoxic treatment. *J Cell Mol Med* 18:1797-1806.

Guerin et al. (2015) Bone-marrow-derived very small embryonic-like stem cells in patients with critical leg ischaemia: evidence of vasculogenic potential. *Thromb Haemost* 113:1084-1094.

Guthrie et al. (2005) The nitric oxide pathway modulates hemangioblast activity of adult hematopoietic stem cells. *Blood* 105:1916-1922

Havens et al. (2013) Human very small embryonic-like cells generate skeletal structures, in vivo. *Stem Cells Dev* 22:622-630.

Havens et al. (2014) Human and murine very small embryonic-like cells represent multipotent tissue progenitors, in vitro and in vivo. *Stem Cells Dev* 23:689-701.

Haynesworth et al. (1992) Characterization of cells with osteogenic potential from human marrow. *Bone* 13:81-88.

Ivanovs et al. (2011) Highly potent human hematopoietic stem cells first emerge in the intraembryonic aortagonad-mesonephros region. *J Exp Med* 208:2417-2427.

Jepson & Lowenstein (1964) Effect of Prolactin on Erythropoiesis in the Mouse. *Blood* 24:726-738.

Jiang et al. (2002) Multipotent progenitor cells can be isolated from postnatal murine bone marrow, muscle and brain. *Exp Hematol* 30:896-904.

Jordan (1917) The History of the Primordial Germ Cells in the Loggerhead Turtle Embryo. *Proc Natl Acad Sci USA* 3:271-275.

Kassmer et al. (2013) Very small embryonic-like stem cells from the murine bone marrow differentiate into epithelial cells of the lung. *Stem Cells* 31:2759-2766.

Kawada & Ogawa (2001) Bone marrow origin of hematopoietic progenitors and stem cells in murine muscle. *Blood* 98:2008-2013

Klein et al. (1996) Decreased inhibin B secretion is associated with the monotropic FSH rise in older, ovulatory women: a study of serum and follicular fluid levels of dimeric inhibin A and B in spontaneous menstrual cycles. *J Clin Endocrinol Metab* 81:2742-2745.

Kritzenberger & Wrobel (2004) Histochemical in situ identification of bovine embryonic blood cells reveals differences to the adult haematopoietic system and suggests a close relationship between haematopoietic stem cells and primordial germ cells. *Histochem Cell Biol* 121:273-289.

Kucia et al. (2006) A population of very small embryonic-like (VSEL) CXCR4(+)SSEA-1(+)Oct-4+ stem cells identified in adult bone marrow. *Leukemia* 20:857-869.

Kucia et al. (2007) Morphological and molecular characterization of novel population of CXCR4+ SSEA-4+ Oct-4+ very small embryonic-like cells purified from human cord blood: preliminary report. *Leukemia* 21:297-303.

Lee et al. (2010) Placenta as a newly identified source of hematopoietic stem cells. *Curr Opin Hematol* 17:313-318.

Lee et al. (2011) Progesterone promotes differentiation of human cord blood fetal T cells into T regulatory cells but suppresses their differentiation into Th17 cells. *J Immunol* 187:1778-1787.

Leitch et al. (2013) Primordial germ-cell development and epigenetic reprogramming in mammals. *Curr Top Dev Biol* 104:149-187.

Lux et al. (2008) All primitive and definitive hematopoietic progenitor cells emerging before E10 in the mouse embryo are products of the yolk sac. *Blood* 111:3435-3438.

Mackay et al. (1998) Chondrogenic differentiation of cultured human mesenchymal stem cells from marrow. *Tissue Eng* 4:415-428.

Maggio et al. (2013) Is the haematopoietic effect of testosterone mediated by erythropoietin? The results of a clinical trial in older men. *Andrology*. 1:24-28.

Majka et al. (2000) Stromal-derived factor 1 and thrombopoietin regulate distinct aspects of human megakaryopoiesis. *Blood* 96:4142-4151.

Majka et al. (2001) Numerous growth factors, cytokines, and chemokines are secreted by human CD34(+) cells, myeloblasts, erythroblasts, and megakaryoblasts and regulate normal hematopoiesis in an autocrine/paracrine manner. *Blood* 97:3075-3085.

Matsumura & Sasaki (1986) [Classifications of megakaryopoietic cells on plastic semithin sections: effects of pregnancy and estrogen administration on megakaryopoiesis]. *Kaibogaku Zasshi* 61:600-608.

McGuckin et al. (2005) Production of stem cells with embryonic characteristics from human umbilical cord blood. *Cell Prolif* 38:245-255.

McKinney-Freeman et al. (2002) Muscle-derived hematopoietic stem cells are hematopoietic in origin. *Proc Natl Acad Sci USA* 99:1341-1346.

Mierzejewska et al. (2015) Hematopoietic stem/progenitor cells express several functional sex hormone receptors-novel evidence for a potential developmental link between hematopoiesis and primordial germ cells. *Stem Cells Dev* 24:927-937.

Milanovich et al. (2015) Sall4 overexpression blocks murine hematopoiesis in a dose-dependent manner. *Exp Hematol* 43:53-64 e1-8.

Miwa et al. (1991) Primitive erythropoiesis of mouse teratocarcinoma stem cells PCC3/A/1 in serum-free medium. *Development* 111:543-549.

Nagata et al. (2003) Proplatelet formation of megakaryocytes is triggered by autocrine-synthesized estradiol. *Genes Dev* 17:2864-2869.

Nakada et al. (2014) Oestrogen increases haematopoietic stem-cell self-renewal in females and during pregnancy. *Nature*. 505:555-558.

Nayernia et al. (2006) Derivation of male germ cells from bone marrow stem cells. *Lab Invest* 86:654-663.

Nichols et al. (1985) Hematologic malignancies associated with primary mediastinal germ-cell tumors. *Ann Intern Med* 102:603-609.

Ohtaka et al. (1999) Hematopoietic development of primordial germ cell-derived mouse embryonic germ cells in culture. *Biochem Biophys Res Commun* 260:475-482.

Olsen & Kovacs (2001) Effects of androgens on T and B lymphocyte development. *Immunol Res* 23:281-288.

Palis (2014) Primitive and definitive erythropoiesis in mammals. *Front Physiol* 5:3.

PCT International Patent Application Publication No. WO 2007/067280.

Pittenger et al. (2000) Human mesenchymal stem cells: progenitor cells for cartilage, bone, fat and stroma. *Curr Top Microbiol Immunol* 251:3-11.

Ratajczak (2015) A novel view of the adult bone marrow stem cell hierarchy and stem cell trafficking. *Leukemia* 29:776-782.

Ratajczak et al. (1994) A reappraisal of the role of insulin-like growth factor I in the regulation of human hematopoiesis. *J Clin Invest* 94:320-327.

Ratajczak et al. (2011a) Adult murine bone marrow-derived very small embryonic-like stem cells differentiate into the hematopoietic lineage after coculture over OP9 stromal cells. *Exp Hematol* 39:225-237.

Ratajczak et al. (2011b) Hematopoietic differentiation of umbilical cord blood-derived very small embryonic/epiblast-like stem cells. *Leukemia* 25:1278-1285.

Ratajczak et al. (2012a) A novel perspective on stem cell homing and mobilization: review on bioactive lipids as potent chemoattractants and cationic peptides as under-appreciated modulators of responsiveness to SDF-1 gradients. *Leukemia* 26:63-72.

Ratajczak et al. (2012b) Very small embryonic/epiblast-like stem cells (VSELs) and their potential role in aging and organ rejuvenation—an update and comparison to other primitive small stem cells isolated from adult tissues. *Aging* (Albany N.Y.) 4:235-246.

Ratajczak et al. (2013) Parental imprinting regulates insulin-like growth factor signaling: a Rosetta Stone for understanding the biology of pluripotent stem cells, aging and cancerogenesis. *Leukemia* 27:773-779.

Ratajczak et al. (2014) Very small embryonic-like stem cells (VSELs) represent a real challenge in stem cell biology: recent pros and cons in the midst of a lively debate. *Leukemia* 28:473-484.

Rich (1995) Primordial germ cells are capable of producing cells of the hematopoietic system in vitro. *Blood* 86:463-472.

Richards & Murphy (2000) Use of human prolactin as a therapeutic protein to potentiate immunohematopoietic function. *J Neuroimmunol* 109:56-62.

Saitoh et al. (1999) Comparison of erythropoietic response to androgen in young and old senescence accelerated mice. *Mech Ageing Dev* 109:125-139.

Sanchez-Aguilera et al. (2014) Estrogen signaling selectively induces apoptosis of hematopoietic progenitors and myeloid neoplasms without harming steady-state hematopoiesis. *Cell Stem Cell* 15:791-804.

Selleri et al. (1991) Danazol: in vitro effects on human hemopoiesis and in vivo activity in hypoplastic and myelodysplastic disorders. *Eur J Haematol* 47:197-203.

Shin et al. (2009) Novel epigenetic mechanisms that control pluripotency and quiescence of adult bone marrow-derived Oct4(+) very small embryonic-like stem cells. *Leukemia* 23:2042-2051.

Shin et al. (2010) Molecular signature of adult bone marrow-purified very small embryonic-like stem cells supports their developmental epiblast/germ line origin. *Leukemia* 24:1450-1461.

Shin et al. (2012) Global gene expression analysis of very small embryonic-like stem cells reveals that the Ezh2-dependent bivalent domain mechanism contributes to their pluripotent state. *Stem Cells Dev* 21:1639-1652.

Sriraman et al. (2015) Mouse Ovarian Very Small Embryonic-Like Stem Cells Resist Chemotherapy and Retain Ability to Initiate Oocyte-Specific Differentiation. *Reprod Sci* 22:884-903.

Stilley et al. (2014) Signaling through FSH receptors on human umbilical vein endothelial cells promotes angiogenesis. *J Clin Endocrinol Metab* 99: E813-20.

Stimpfel et al. (2013) Isolation, characterization and differentiation of cells expressing pluripotent/multipotent markers from adult human ovaries. *Cell Tissue Res* 354: 593-607.

Suszynska et al. (2014a) Expression of the erythropoietin receptor by germline-derived cells—further support for a potential developmental link between the germline and hematopoiesis. *J Ovarian Res* 7:66.

Suszynska et al. (2014b) The proper criteria for identification and sorting of very small embryonic-like stem cells, and some nomenclature issues. *Stem Cells Dev* 23:702-713.

Tamamura et al. (1998) A low-molecular-weight inhibitor against the chemokine receptor CXCR4: a strong anti-HIV peptide T140. *Biochem Biophys Res Comm* 253:877-882.

Thangamani et al. (2015) Cutting edge: progesterone directly upregulates vitamin d receptor gene expression for efficient regulation of T cells by calcitriol. *J Immunol* 194:883-886.

U.S. Patent Application Publication Nos. 2009/0220466; 2013/0323197.

U.S. Pat. No. 8,859,282.

Venkatraman et al. (2013) Maternal imprinting at the H19-Igf2 locus maintains adult haematopoietic stem cell quiescence. *Nature* 500:345-349.

Wang et al. (1991) Gonadal dysfunction and changes in sex hormones in postnecrotic cirrhotic men: a matched study with alcoholic cirrhotic men. *Hepatogastroenterology* 38:531-534.

West et al. (2013) In vitro-derived gametes from stem cells. *Sem Reprod Med* 31:33-38.

Woodruff et al. (1995) The clonal nature of mediastinal germ cell tumors and acute myelogenous leukemia. A case report and review of the literature. *Cancer Genet Cytogenet* 79:25-31.

Wu et al. (2012) The bone marrow-expressed antimicrobial cationic peptide LL-37 enhances the responsiveness of hematopoietic stem progenitor cells to an SDF-1 gradient and accelerates their engraftment after transplantation. *Leukemia* 26:736-745.

Yoo et al. (1998) The chondrogenic potential of human bone-marrow-derived mesenchymal progenitor cells. *J Bone Joint Surg Am* 80:1745-1757.

Yoshimoto et al. (2009) Bone marrow engraftment but limited expansion of hematopoietic cells from multipotent germline stem cells derived from neonatal mouse testis. *Exp Hematol* 37:1400-1410.

Young et al. (1998) Use of mesenchymal stem cells in a collagen matrix for Achilles tendon repair. J Orthop Res 16:406-413.

Yu et al. (1987) Importance of FSH-releasing protein and inhibin in erythrodifferentiation. *Nature* 330:765-767.

Zuba-Surma & Ratajczak (2010) Overview of very small embryonic-like stem cells (VSELs) and methodology of their identification and isolation by flow cytometric methods. *Curr Protoc Cytom* Chapter 9: Unit 9.29.

Zuba-Surma et al. (2009) Fetal liver very small embryonic/epiblast like stem cells follow developmental migratory pathway of hematopoietic stem cells. *Ann NY Acad Sci* 1176:205-218.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for expanding stem cells, the method comprising:
   (a) providing a purified population of CD45⁻ or CD45⁺ stem cells, wherein the purified population of CD45⁻ or CD45⁺ stem cells are CD34⁺ human cells or Sca-1⁺ murine cells that are positive for at least one gene product selected from the group consisting of follicle-stimulating hormone receptor (FSHR), luteinizing hormone/choriogonadotropin receptor (LHCGR), prolactin receptor (PRLR), androgen receptor (AR), estrogen receptor α (ESRα), estrogen receptor β (ESRβ), and progesterone receptor (PGR), and further wherein the purified population of CD45⁻ or CD45⁺ stem cells are negative for each of CD45R/B220, Gr-1, TCRαβ, TCRγδ, CD11b, and Ter-119; and
   (b) growing the purified population of CD45⁻ or CD45⁺ stem cells in culture in the presence of (i) one or more pituitary or gonadal sex hormones; and (ii) suboptimal doses of hematopoietic cytokines and growth factors under conditions and for a time sufficient to expand the CD45⁻ or CD45⁺ stem cells, wherein the suboptimal doses of hematopoietic cytokines and growth factors are selected from the group consisting of 0.8-1.2 ng/mL recombinant human interleukin-3 (rhIL-3) and 0.4-0.6 ng/mL recombinant human granulocyte/macrophage colony-stimulating factor (rhGM-CSF); 0.16-2.4 IU/mL of recombinant human erythropoietin (rhEPO) and 0.8-1.2 ng/mL of recombinant human stem cell factor (rhSCF); 4-6 ng/mL of recombinant human thrombopoietin (rhTPO) and 0.8-1.2 ng/mL of rhIL-3; and 0.8-1.2 ng/mL of rhIL-3, 0.4-0.6 ng/mL of G-CSF, 0.8-1.2 ng/mL of rhSCF, 0.16-2.4 IU/mL of rhEPO, and 4-6 ng/mL of rhTPO; and further wherein the purified population of CD45⁻ or CD45⁺ stem cells is a population of stem cells selected from the group consisting of CD45⁺ hematopoietic stem/progenitor cells (HSPCs), CD45⁺ mesenchymal stromal cells (MSCs), CD45⁻ very small embryonic-like stem cells (VSELs), and combinations thereof, and further wherein one or more of the HSPCs, the MSCs, and the VSELs are human HSPCs, human MSCs or human VSELs.

2. The method of claim 1, wherein the one or more pituitary or gonadal sex hormones are selected from the group consisting of follicle-stimulating hormone (FSH), luteinizing hormone (LH), prolactin hormone (PRL), an androgen, an estrogen, and progesterone (PG).

3. The method of claim 1, wherein the conditions and the time sufficient to expand the CD45⁻ or CD45⁺ stem cells are sufficient to induce at least a 25% increase in number of burst-forming unit-erythroid (BFU-E) colonies, CFU-granulocyte/macrophage (CFU-GM) colonies, CFU-megakaryocytes (CFU-meg) colonies, or CFU-Mix colonies.

* * * * *